(12) United States Patent
Champion et al.

(10) Patent No.: US 12,071,638 B2
(45) Date of Patent: *Aug. 27, 2024

(54) VARIANTS OF TERMINAL DEOXYNUCLEOTIDYL TRANSFERASE AND USES THEREOF

(71) Applicants: DNA Script, Paris (FR); Institut Pasteur, Paris (FR); Centre National de la Recherche Scientifique, Paris (FR)

(72) Inventors: Elise Champion, Paris (FR); Mikhael Soskine, Franconville (FR); Thomas Ybert, Paris (FR); Marc Delarue, Versailles (FR)

(73) Assignees: DNA Script, Le Kremlin-Bicêtre (FR); Institut Pasteur, Le Kremlin-Bicêtre (FR); Centre National de la Recherche Scientifique, Paris (FR)

( * ) Notice: Subject to any disclaimer, the term of this patent is extended or adjusted under 35 U.S.C. 154(b) by 118 days.

This patent is subject to a terminal disclaimer.

(21) Appl. No.: 17/544,647

(22) Filed: Dec. 7, 2021

(65) Prior Publication Data

US 2022/0403354 A1 Dec. 22, 2022

Related U.S. Application Data

(63) Continuation of application No. 16/925,785, filed on Jul. 10, 2020, now Pat. No. 11,208,637, which is a continuation of application No. 16/423,972, filed on May 28, 2019, now Pat. No. 10,752,887, which is a continuation-in-part of application No. 16/242,904, filed on Jan. 8, 2019, now Pat. No. 10,435,676.

(30) Foreign Application Priority Data

Jan. 8, 2018 (EP) .................................... 18305006

(51) Int. Cl.
*C12N 15/70* (2006.01)
*C12N 9/12* (2006.01)

(52) U.S. Cl.
CPC ........... *C12N 9/1264* (2013.01); *C12N 15/70* (2013.01); *C12Y 207/07031* (2013.01)

(58) Field of Classification Search
CPC ........... C12N 9/12; C12N 19/34; C12N 11/00
See application file for complete search history.

(56) References Cited

U.S. PATENT DOCUMENTS

| 4,448,883 | A | 5/1984 | Case |
|---|---|---|---|
| 4,772,691 | A | 9/1988 | Herman |
| 5,436,143 | A | 7/1995 | Hyman |
| 5,516,664 | A | 5/1996 | Hyman |
| 5,602,000 | A | 2/1997 | Hyman |
| 5,656,745 | A | 8/1997 | Bischofberger |
| 5,744,595 | A | 4/1998 | Srivastava |
| 5,763,594 | A | 6/1998 | Hiatt |
| 5,808,045 | A | 9/1998 | Hiatt |
| 5,872,244 | A | 2/1999 | Hiatt |
| 5,917,031 | A | 6/1999 | Miura |
| 5,935,527 | A | 8/1999 | Andrus |
| 5,990,300 | A | 11/1999 | Hiatt |
| 6,214,987 | B1 | 4/2001 | Hiatt |
| 6,232,465 | B1 | 5/2001 | Hiatt |
| 6,623,929 | B1 | 9/2003 | Densham |
| 6,777,189 | B2 | 8/2004 | Wei |
| 7,057,026 | B2 | 1/2006 | Barnes |
| 7,078,499 | B2 | 7/2006 | Odedra |
| 7,125,671 | B2 | 10/2006 | Sood |
| 7,270,951 | B1 | 9/2007 | Stemple |
| 7,407,757 | B2 | 8/2008 | Brenner |
| 7,494,797 | B2 | 2/2009 | Mueller |
| 7,544,794 | B1 | 6/2009 | Benner |
| 7,939,259 | B2 | 5/2011 | Kokoris |
| 8,034,923 | B1 | 10/2011 | Benner |
| 8,212,020 | B2 | 7/2012 | Benner |
| 8,263,335 | B2 | 9/2012 | Carr |
| 8,674,086 | B2 | 3/2014 | Liu |
| 8,808,988 | B2 | 8/2014 | Zhao |
| 8,808,989 | B1 | 8/2014 | Efcavitch |
| 9,896,709 | B2 | 2/2018 | Makarov |
| 10,059,929 | B2 | 8/2018 | Efcavitch |
| 10,435,676 | B2 | 10/2019 | Champion et al. |
| 10,752,887 | B2 * | 8/2020 | Champion ............. C12N 15/70 |
| 11,208,637 | B2 | 12/2021 | Champion |

(Continued)

FOREIGN PATENT DOCUMENTS

| WO | 2016064880 | 4/2016 |
|---|---|---|
| WO | 2016128731 | 8/2016 |

(Continued)

OTHER PUBLICATIONS

Accession No. A4PCE2, (2007).
Aoufouchi et al. (2000) "Two novel human and mouse DNA polymerases of the polX family," Nucleic Acids Research, 28(18): 3684-3693.
Arana et al. (2008) "Low-fidelity DNA synthesis by human DNA polymerase theta" Nucleic Acids Research 36(11): 3847-3856.
Beabealashvilli et al. (1986) "Nucleoside 5'-triphosphates modified at sugar residues as substrates for calf thymus terminal deoxynucleotidyl transferase and for AMV reverse transcriptase," Biochim. Biophys. Acta., 868(2-3): 136-144.

(Continued)

*Primary Examiner* — Tekchand Saidha

(74) *Attorney, Agent, or Firm* — MORRISON & FOERSTER LLP

(57) ABSTRACT

The present invention relates to variants of Terminal deoxynucleotidyl Transferase (TdT), each of which (i) has an amino acid sequence similarity to SEQ ID NO: 2, 11, 13, 15, 17, 19, 21, 23, 25, 27, 29, 31, 33 or 35 with corresponding amino acid substitutions, (ii) is capable of synthesizing a nucleic acid fragment without a template and (iii) is capable of incorporating a modified nucleotide into the nucleic acid fragment.

22 Claims, 2 Drawing Sheets

Specification includes a Sequence Listing.

(56) References Cited

U.S. PATENT DOCUMENTS

| | | |
|---|---|---|
| 2006/0240439 A1 | 10/2006 | Smith et al. |
| 2014/0363851 A1 | 12/2014 | Efcavitch |
| 2014/0363852 A1 | 12/2014 | Efcavitch |
| 2016/0108382 A1 | 4/2016 | Efcavitch et al. |
| 2018/0016609 A1 | 1/2018 | Chen et al. |
| 2018/0023108 A1 | 1/2018 | Chen |
| 2018/0274001 A1 | 9/2018 | Efcavitch et al. |
| 2018/0312820 A1 | 11/2018 | Pomerantz et al. |
| 2019/0211315 A1 | 7/2019 | Champion |
| 2019/0390178 A1 | 12/2019 | Champion |
| 2020/0002690 A1 | 1/2020 | Ybert et al. |
| 2021/0009970 A1 | 1/2021 | Champion |

FOREIGN PATENT DOCUMENTS

| | | |
|---|---|---|
| WO | 2017075421 | 5/2017 |
| WO | 2017216472 | 12/2017 |
| WO | 2018102818 A1 | 6/2018 |
| WO | 2018215803 | 11/2018 |

OTHER PUBLICATIONS

Bentoila et al. (1995) "The two isoforms of mouse terminal deoxynucleotidyl transferase differ in both the ability to add N regions and subcellular localization," The EMBO Journal, 14(17): 4221-4229.

Boule et al. (1998) "High-level expression of murine terminal deoxynucleotidyl transferase in *Escherichia coli* grown at low temperature and overexpressing argU IRNA," Molecular Biotechnology, 10: 199-208.

Database EPO Proteins, (2016) "Sequence 8 from Patent WO2016128731", XP002779827.

Database Refseq (2016) Predicted: DNA polymerase theta isoform X1 [Rhinolophus sinicus], XP-002776331, 2 pages.

Database UniProt, (2017) SubName: Full=DNA nucleotidylexotransferase isoform X1{EC0:0000313:RefSeq: XP_008057295.1}, XP002779838.

Delarue et al. (2002) "Crystal structures of a template-independent DNA polymerase: murine terminal deoxynucleotidyltransferase," The EMBO Journal, 21(3): 427-439.

Dominguez et al. (2000) "DNA polymerase mu (Pol □), homologous to TdT, could act as a DNA mutator in eukaryotic cells," The EMBO Journal, 19(17): 1731-1742.

Flickinger et al. (1992) "Differential incorporation of biotinylated nucleotides by terminal deoxynucleotidyl transferase," Nucleic Acids Research, 20(9): 2382.

Gouge et al. (2013) "Structures of intermediates along the catalytic cycle of terminal deoxynucleotidyltransferase: dynamical aspects of the two-metal ion mechanism," J. Mol. Biol., 425: 4334-4352.

Hogg et al. (2012) "Promiscuous DNA synthesis by human DNA polymerase 8" Nucleic Acids Research 40(6): 2611-2622.

International Search Report from PCT International Application No. PCT/EP2018/071217 dated Feb. 14, 2019.

International Search Report from PCT International Application No. PCT/EP2019/050334 dated Feb. 22, 2019.

International Search Report from PCT International Application No. PCT/FR2017/051519 dated Jan. 18, 2018.

Koiwai et al. (1986) "Isolation and characterization of bovine and mouse terminal deoxynucleotidyltransferase cDNAS expressible in mammalian cells," Nucleic Acids Research, 14(14): 5777-5792.

Li et al. (1998) "Crystal structures of open and closed forms of binary and ternary complexes of the large fragment of Thermus aquaticus DNA polymerase I: structural basis for nucleotide incorporation" EMBO J. 17(24): 7514-7525.

Michelson et al. (1982) "Characterization of the homopolymer tailing reaction catalyzed by terminal deoxynucleotidyl transferase," J. Biol. Chem., 257(24): 14773-14782.

Motea et al. (2010) "Terminal deoxynucleotidyl transferase: The story of a misguided DNA polymerase," Biochim Biophys Acta, 1804(5): 1151-1166.

Patel et al. (2000) "DNA polymerase active site is highly mutable: Evolutionary consequences" Proc. Natl. Acad. Sci. USA 97(10): 5095-5100.

PIR Accession No. WXHU, published Dec. 4, 1986 (Year: 1986).

PIR Accession No. A23595, published Sep. 10, 1999 (Year: 1999).

PIR Accession No. S55786, published Oct. 27, 1995 (Year: 1995).

PIR Accession No. 151658, published Sep. 13, 1996 (Year: 1996).

Romain et al. (2009) "Conferring a template-dependent polymerase activity to terminal deoxynucleotidyltransferase by mutations in the Loop1 region," Nucleic Acids Research, 37(14): 4642-4656.

Schmitz et al. (1999) "Solid-phase enzymatic synthesis of oligonucleotides," Organic Lett., 1(11): 1729-1731.

Schott et al. (1984) "Single-step elongation of oligodeoxynucleotides using terminal deoxynucleotidyl transferase," Eur. J. Biochem., 143: 613-620.

Schultz et al. (2015) "Taq DNA Polymerase Mutants and 2'-Modified Sugar Recognition" Biochemistry 54: 5999-6008.

Shima et al. (2003) "Phenotype-Based Identification of Mouse Chromosome Instability Mutants" Genetics 163: 1031-1040.

Singapore Patent Office, Written Opinion in Singapore Patent Application No. 11201809961T (dated Apr. 24, 2020).

Song et al. (2021) "Large-Scale de novo Oligonucleotide Synthesis for Whole-Genome Synthesis and data Storage", Frontiers Bioeng. Biotechnol. 9, 2021, 689797.

Troshchynsky et al. (2015) "Functional analyses of polymorphic variants of human terminal deoxynucleotidyl transferase," Genes and Immunity, 16: 388-398.

UD-Dean, (2008) "A theoretical model for template-free synthesis of long DNA sequence," Syst. Synth. Biol., 2: 67-73.

Uniprot, Accession No. 075417 (2016) www.uniprot.org. 8 pages.

Written Opinion from PCT International Application No. PCT/EP2018/071217 dated Feb. 14, 2019.

Written Opinion from PCT International Application No. PCT/FR2017/051519 dated Jan. 18, 2018.

Yamtich et al. (2010) "DNA polymerase family X: function, structure, and cellular roles," Biochim. Biophys. Acta., 1804(5): 1136-1150.

Yang et al. (1994) "Mutational analysis of residues in the nucleotide binding domain of human terminal deoxynucleotidyl transferase," Journal of Biological Chemistry, 269(16): 11859-11868.

Yang et al. (1995) "T-cell specific avian TdT: characterization of the cDNA and recombinant ezyme," Nucleic Acids Research, 23(11): 2041-2048.

Yousefzadeh et al. (2014) "Mechanism of Suppression of Chromosomal Instability by DNA Polymerase POLQ" PLOS Genetics 10(10): e1004654, 15 pages.

Zahn et al. (2015) "Human DNA polymerase θ grasps the primer terminus to mediate DNA repair" Nat Struc Mol Biol 22(4): 304-3011.

* cited by examiner

VARIANTS OF TERMINAL DEOXYNUCLEOTIDYL TRANSFERASE AND USES THEREOF

CROSS-REFERENCE TO RELATED APPLICATIONS

This application is a continuation of U.S. patent application Ser. No. 16/925,785, filed Jul. 10, 2020, issued as U.S. Pat. No. 11,208,637, which application is a continuation of U.S. patent application Ser. No. 16/423,972, filed May 28, 2019, issued as U.S. Pat. No. 10,752,887, which application is a continuation-in-part of U.S. patent application Ser. No. 16/242,904, filed Jan. 8, 2019, issued as U.S. Pat. No. 10,435,676, which application claims priority to European Patent Application Serial No. 18305006.1, filed Jan. 8, 2018, which applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 283182001002SUBSEQLIST.txt, date recorded: Jan. 22, 2024, size: 121,152 bytes).

FIELD OF THE INVENTION

The invention relates to variants of Terminal deoxynucleotidyl Transferase (TdT) and uses thereof for the enzymatic synthesis of nucleic acid sequences without template. More particularly, the present invention relates to such variants suitable to incorporate modified nucleotides, for the synthesis of nucleic acid molecules with determined or controlled sequences.

BACKGROUND

Methods for de novo chemical synthesis of nucleic acids based on solid-phase phosphoramidite chemistry have been largely used and refined over the past 40 years. The technique consists of a four-step chain elongation cycle that adds one base per cycle onto a growing oligonucleotide chain attached to a solid support matrix. Although it has been the method of choice to synthesize nucleic acids during the past decades, this technology has some notable limitations: It requires the use of multiple solvents and reagents, and due to limitations in chemical reaction efficiency, the length of synthetic oligonucleotides typically do not exceed 150-200 bases. Moreover, these short fragments need to be further assembled to provide the desired DNA sequence.

One alternative to chemical synthesis consists in using template independent DNA polymerases that will add reversible terminator modified nucleotides to a growing single stranded chain of nucleic acids. This allows the addition of one type of nucleotide per cycle in a controlled fashion.

Some native enzymes are able to act on natural nucleotides in the absence of template and so can catalyze the synthesis of nucleic acids in an uncontrolled fashion. However, they are particularly inefficient to incorporate modified nucleotides and more particularly reversible terminator modified nucleotides. Efforts have been made to develop new DNA polymerases able to act on modified nucleotides but the resulting enzymes are not fully satisfactory in terms of performances for the synthesis of any type of nucleic acids.

So far, only few DNA polymerases that can act efficiently on single strand DNA (without the use of template) have been identified. The most characterized polymerase having such template-independent activity is the Terminal deoxynucleotidyl Transferase (TdT). TdT enzymes have been extensively used to modify single stranded DNA for various types of applications including biotechnology, biomedical research and synthetic biology. However, native TdT is poorly able to use modified nucleotides.

Several attempts to develop modified TdT with acceptable performance for the incorporation of modified nucleotides have been carried over. However, the performances of the incorporation of such modified nucleotides is still a limiting factor. Incorporation efficiency is the key parameter driving the overall purity and yield of synthesis. These two characteristics of the synthesis process have a significant impact of quality, turnaround time and cost of nucleic acid products.

There is therefore a need to develop improved TdT capable to use modified nucleotides in the absence of template, for developing efficient and cost-effective methods for the nucleic acid synthesis.

SUMMARY OF THE INVENTION

By working on TdT for de novo synthesis of polynucleotides with controlled sequence and without the use of a template, the inventors have discovered that some targeted amino acid residues of the catalytic domain of the TdT may be specifically modified to improve the ability of such modified TdT for synthesizing polynucleotides. More particularly, the inventors have developed modified TdTs with targeted amino acid substitution(s) that lead to improve the enzymatic synthesis of polynucleotides and to reduce the overall cost of synthesizing polynucleotides. In some embodiments, each of the modified TdTs presents one or more targeted amino acids substitution as compared to wild-type TdTs (such as SEQ ID NOs:1, 10, 12, 14, 16, 18, 20, 22, 24, 26, 28, 30, 32 or 34) and N-terminal truncated versions thereof that comprise a TdT catalytic domain. In some embodiments, each of the modified TdTs of the invention possesses an amino acid sequence having a specified percent sequence identity with a catalytic domain of aTdT (such as SEQ ID NOs:2, 11, 13, 15, 17, 19, 21, 23, 25, 27, 29, 31, 33 or 35) and having one or more specified amino acid substitution(s). The template-independent polymerases of the invention allow the enzymatic synthesis of polynucleotides at a faster rate, with less expense and higher quality.

It is therefore an object of the invention to provide variants of Terminal deoxynucleotidyl Transferase (TdT) which (i) comprise an amino acid sequence of a TdT catalytic domain or of a percent sequence identity of a TdT catalytic domain, such as set forth in SEQ ID NOs 2, 11, 13, 15, 17, 19, 21, 23, 25, 27, 29, 31, 33 or 35, with at least an amino acid substitution at position corresponding to residue C302 (with respect to the amino acid numbering of SEQ ID NO: 1), or functionally equivalent residue, (ii) is capable of synthesizing a nucleic acid fragment without template and (iii) is capable of incorporating a modified nucleotide, such as a 3'-O— modified nucleotide onto a free 3'-hydroxyl of a nucleic fragment.

More particularly, it is an object of the present invention to provide terminal deoxynucleotidyl transferase (TdT) variants comprising an amino acid sequence at least 90% identical to SEQ ID NO: 2, 11, 13, 15, 17, 19, 21, 23, 25, 27, 29, 31, 33 or 35 with a substitution at position corresponding to residue C173 with respect to SEQ ID NOs 2, 11, 13, 17, 19, 21, 29 or 31, or at position corresponding to residue C172 with respect to SEQ ID NO: 15, or at position corresponding to residue C178 with respect to SEQ ID NO: 23, or at position corresponding to residue C174 with respect to SEQ ID NO: 25, or at position corresponding to residue C171 with respect to SEQ ID NO: 27, or at position corresponding to residue C182 with respect to SEQ ID NO: 33, or at position corresponding to residue C176 with respect to SEQ ID NO: 35, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity.

Advantageously, in regard to (iii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In a particular embodiment, the substitution is selected from:
C302G/R/P/A/V/S/N/Q/D with respect to SEQ ID NO:1; or C173G/R/P/A/V/S/N/Q/D with respect to SEQ ID NO:2; or
C313G/R/P/A/V/S/N/Q/D with respect to SEQ ID NO: 10; or C173G/R/P/A/V/S/N/Q/D with respect to SEQ ID NO:11; or C302G/R/P/A/V/S/N/Q/D with respect to SEQ ID NO:12; or
C173G/R/P/A/V/S/N/Q/D with respect to SEQ ID NO: 13; or C302G/R/P/A/V/S/N/Q/D with respect to SEQ ID NO:14; or C172G/R/P/A/V/S/N/Q/D with respect to SEQ ID NO:15; or
C304G/R/P/A/V/S/N/Q/D with respect to SEQ ID NO:16; or C173G/R/P/A/V/S/N/Q/D with respect to SEQ ID NO:17; or C304G/R/P/A/V/S/N/Q/D with respect to SEQ ID NO:18; or
C173G/R/P/A/V/S/N/Q/D with respect to SEQ ID NO:19; or C293G/R/P/A/V/S/N/Q/D with respect to SEQ ID NO:20; or C174G/R/P/A/V/S/N/Q/D with respect to SEQ ID NO:21; or
C282G/R/P/A/V/S/N/Q/D with respect to SEQ ID NO:22; or C173G/R/P/A/V/S/N/Q/D with respect to SEQ ID NO:23; or C304G/R/P/A/V/S/N/Q/D with respect to SEQ ID NO:24; or
C174G/R/P/A/V/S/N/Q/D with respect to SEQ ID NO:25; or C300G/R/P/A/V/S/N/Q/D with respect to SEQ ID NO:26; or C171G/R/P/A/V/S/N/Q/D with respect to SEQ ID NO:27; or
C305G/R/P/A/V/S/N/Q/D with respect to SEQ ID NO:28; or C173G/R/P/A/V/S/N/Q/D with respect to SEQ ID NO:29; or C302G/R/P/A/V/S/N/Q/D with respect to SEQ ID NO:30; or
C173G/R/P/A/V/S/N/Q/D with respect to SEQ ID NO:31; or C313G/R/P/A/V/S/N/Q/D with respect to SEQ ID NO:32; or C182G/R/P/A/V/S/N/Q/D with respect to SEQ ID NO:33; or
C271G/R/P/A/V/S/N/Q/D with respect to SEQ ID NO:34; or C176G/R/P/A/V/S/N/Q/D with respect to SEQ ID NO:35.

In a further embodiment, the substitution is selected from:
C302G/R with respect to SEQ ID NO:1; or C302G/R with respect to SEQ ID NO:1; or C173G/R with respect to SEQ ID NO:2; or C302G/R with respect to SEQ ID NO:4; or C302G/R with respect to SEQ ID NO:9; or C313G/R with respect to SEQ ID NO:10; or C173G/R with respect to SEQ ID NO:11; or C302G/R with respect to SEQ ID NO:12; or C173G/R with respect to SEQ ID NO:13; or C302G/R with respect to SEQ ID NO:14; or C172G/R with respect to SEQ ID NO:15; or C304G/R with respect to SEQ ID NO:16; or C173G/R with respect to SEQ ID NO:17; or C304G/R with respect to SEQ ID NO:18; or C173G/R with respect to SEQ ID NO:19; or C293G/R with respect to SEQ ID NO:20; or C173G/R with respect to SEQ ID NO:21; or C282G/R with respect to SEQ ID NO:22; or C173G/R with respect to SEQ ID NO:23; or C304G/R with respect to SEQ ID NO:24; or C174G/R with respect to SEQ ID NO:25; or C300G/R with respect to SEQ ID NO:26; or C171G/R with respect to SEQ ID NO:27; or C305G/R with respect to SEQ ID NO:28; or C173G/R with respect to SEQ ID NO:29; or C302G/R with respect to SEQ ID NO:30; or C173G/R with respect to SEQ ID NO:31; or C313G/R with respect to SEQ ID NO:32; or C182G/R with respect to SEQ ID NO:33; or C271G/R with respect to SEQ ID NO:34; or C176G/R with respect to SEQ ID NO:35.

In some embodiments, the invention is directed to compositions comprising TdT variants comprising amino acid sequence having at least 90 percent identity, or in some embodiments, at least 95 percent identity, or in some embodiments, at least 97 percent identity, or in some embodiments, at least 98 percent identity, with a reference or wild type TdT sequence selected from the group consisting of SEQ ID NOs: 2, 11, 13, 15, 17, 19, 21, 23, 25, 27, 29, 31, 33 and 35, wherein (i) such TdT variants have a mutation selected from C173G/R/P/A/V/S/N/Q/D, such as C173G/R (wherein the amino acid residue number is with respect to SEQ ID NO: 2, or an equivalent residue number of SEQ ID NOs 11, 13, 15, 17, 19, 21, 23, 25, 27, 29, 31, 33 or 35) and (ii) such TdT variants incorporate a modified nucleotide, such as a 3'-O-modified nucleoside triphosphates, with greater efficiency, or at a higher rate, than the reference or wild type TdT.

In some embodiments, it is also an object of the invention to provide truncated variants of Terminal deoxynucleotidyl Transferase (TdT) each of which (i) comprises an amino acid sequence with at least 95 percent identity to any of SEQ ID NOs:11, 13, 15, 17, 19, 21, 23, 25, 27, 29, 31, 33 or 35 with at least two amino acid substitutions, such as at least three amino acid substitutions, selected from M192R/Q, L260P, C302G/R, R336L/N, D379V, R454P/N and E457N/L/T/S, (wherein residue numbers are with respect to SEQ ID NO:1 or with respect to their functionally equivalent residues numbers in SEQ ID NOs 11, 13, 15, 17, 19, 21, 23, 25, 27, 29, 31, 33 or 35), (ii) is able to synthesize a nucleic acid fragment without a template and (iii) is able to incorporate a modified nucleotide into the nucleic acid fragment, for example, a 3'-O-reversibly blocked deoxynucleoside triphosphate onto a free 3'-hydroxyl of a nucleic acid fragment. In further embodiments, the above percent sequence identity value is at least 98 percent identity with the specified sequences.

It is another object of the invention to provide a nucleic acid molecule encoding a variant of a TdT as defined above and/or an expression vector comprising such nucleic acid molecule, and/or a host cell comprising such nucleic acid molecule or expression vector.

It is a further object of the invention to provide a process for producing a variant of TdT according to the invention, wherein a host cell as defined above is cultivated under culture conditions allowing the expression of the nucleic acid encoding said variant, and wherein the variant is optionally retrieved.

The invention further relates to the use of a variant of TdT, for synthesizing a nucleic acid molecule without template, by the successive addition of one or more 3'O-modified nucleotides to a nucleic acid fragment. In some embodiments, such methods comprise the steps of (a) providing an initiator comprising an oligonucleotide having a free 3'-hydroxyl; (b) reacting under enzymatic extension conditions a TdT variant of the invention with the initiator or an extended initiator in the presence of a 3'-O-reversibly blocked nucleoside. In some embodiments, such method further includes steps of (c) deblocking the extended initiators to form extended initiators with free 3'-hydroxyls and (d) repeating steps (b) and (c) until a nucleic acid molecule of a predetermined sequence is synthesized.

It is also an object of the invention to provide a process for synthesizing a nucleic acid molecule without template, comprising a step of contacting a nucleic acid primer with both at least one nucleotide, such as at least one modified nucleotides, such as a 3'O-modified nucleotide, and a variant of TdT according to the invention.

The present invention further provides a kit for performing a nucleotide incorporation reaction comprising a variant of TdT according to the invention, and one or more nucleotides, such as one or more modified nucleotides, such as a 3'O-modified nucleotides, and optionally at least one nucleic acid primer.

DESCRIPTION OF THE INVENTION

Figure 1:
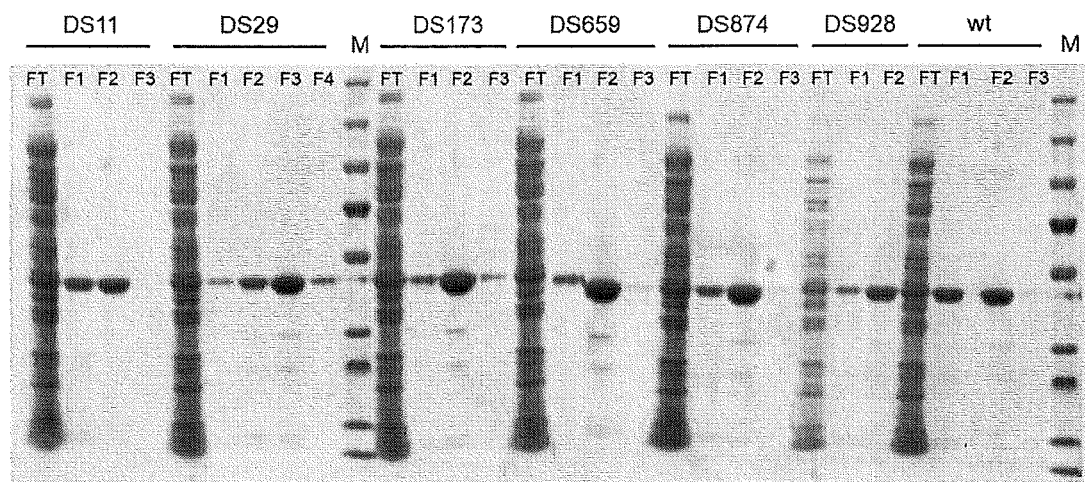
FIG. 1: Purification assay of wild type (wt) TdT and different TdT variants of the invention. Protein samples were loaded on SDS-PAGE analysis gel and migrated through electrophoresis.

The DNA polymerase families are divided into seven families based on their sequence homology and crystal structure. Among them, the polymerases of PolX family represent a wide variety of polymerases from replicative polymerases to terminal transferase enzymes. Polymerases from PolX family are present across a very wide range of eukaryotic organisms. Polymerases from the PolX family are implicated in a vast variety of biological processes and in particular in DNA damage repair mechanisms or error correction mechanisms. The PolX family regroups polymerase β (Pol β), μ (Pol μ), λ (Pol λ), IV from yeast (Pol IV) and the Terminal deoxynucleotidyl Transferase (TdT). TdT is naturally implicated in DNA repair and maintenance mechanisms. In particular, TdT has the unique ability to conserve a nucleotide polymerization activity even in absence of template strand. In specific conditions and with natural nucleotides, TdT is able to elongate DNA fragments with several hundred nucleotides, in absence of any complementary strand. However, wild type TdT is totally unable to efficiently incorporate sugar-modified nucleotides.

It is thus the purpose of the present invention to provide variants of TdT with targeted mutation(s) that allow them to incorporate modified nucleotides into a nucleic fragment during synthesize of said nucleotide fragment. More particularly, the inventors have identified specific amino acid residues that may be advantageously substituted, alone or in combination, to improve the ability of the enzyme to synthesize nucleic acid fragments of various length and with pre-determined sequence, including by using modified nucleotides.

DEFINITIONS

As used therein, the terms "mutant" and "variant" may be used interchangeably to refer to polypeptides related to or derived from SEQ ID NOs:2, 11, 12, 13, 14, 15, 16, 17, 18, 19, 20, 21, 22, 23, 24, 25, 26 27, 28, 29, 30, 31, 32, 33, 34 or 35 and comprising a modification or an alteration, i.e., a substitution, insertion, and/or deletion, at one or more (e.g., several) positions and having both a polymerase activity without template and ability to incorporate 3'-O-modified nucleoside triphosphates into a nucleic acid chain. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction. Mutagenesis activities consist in deleting, inserting or substituting one or several amino-acids in the sequence of a protein or in the case of the invention of a polymerase. Targeted amino-acids could be concomitant or distributed along the whole sequence of the polymerase. Specific motifs or structural features could be targeted for example.

The terms "modification" or "alteration" as used herein in relation to a position or amino acid mean that the amino acid in the specific position has been modified compared to the amino acid of the wild-type protein.

A "substitution" means that an amino acid residue is replaced by another amino acid residue. For example, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methyllysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). For example, the term "substitution" refers to the replacement of an amino acid residue by another selected from the naturally-occurring standard 20 amino acid residues. The sign "+" indicates a combination of substitutions.

The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N:

asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

As used herein, the terms "sequence identity" or "identity" refer to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are aligned using a global alignment algorithm (e.g. Needleman and Wunsch algorithm; Needleman and Wunsch, 1970) which aligns the sequences optimally over the entire length, while sequences of substantially different lengths are aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/or http://www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

Herein, the terms "peptide", "polypeptide", "protein", "enzyme", refer to a chain of amino acids linked by peptide bonds, regardless of the number of amino acids forming said chain.

Unless otherwise specified, the positions disclosed in the present application are numbered by reference to the amino acid sequence set forth in a specified SEQ ID NO.

Variants of TdT

The present invention provides variants of TdT enzyme that can be used for synthesizing polynucleotides of predetermined sequences, such as DNA or RNA, without the use of template strand. The TdT variants of the invention allow modified nucleotides, and more particularly 3'O-modified nucleotides, to be used in an enzyme-mediated method of polynucleotide synthesis, such as described by Hiatt et al, U.S. Pat. No. 5,763,594.

In some embodiments of the invention, "modified Terminal desoxyribonucleotidyl Transferase", "modified TdT", "variants of Terminal desoxyribonucleotidyl Transferase" and "variants of TdT" refer to enzymes that comprise an amino acid segment that shares at least 80% identity with an amino acid sequence of one of the amino acid sequences set forth in SEQ ID NOs:2, 11, 13, 15, 17, 19, 21, 23, 25, 27, 29, 31, 33 or 35, excepting at least one amino acid residue substitution. In some embodiments, the variant of TdT comprises an amino acid sequence that shares at least 90% identity with SEQ ID NOs:2, 11, 13, 15, 17, 19, 21, 23, 25, 27, 29, 31, 33, 35, and having at least one amino acid residue substitution. In still other embodiments, the variant of TdT comprises an amino acid sequence that shares at least 95% identity with SEQ ID NOs:2, 11, 13, 15, 17, 19, 21, 23, 25, 27, 29, 31, 33, 35, and having at least one amino acid residue substitution. In still other embodiments, the variant of TdT comprises an amino acid sequence that shares at least 98% identity with SEQ ID NOs:2, 11, 13, 15, 17, 19, 21, 23, 25, 27, 29, 31, 33, 35, and having at least one amino acid residue substitution.

In some cases, variants of the present invention may be described according to their mutations on specific residues, whose positions are determined by alignment with or reference to the enzymatic sequence SEQ ID NO:1 or SEQ ID NO:2, which corresponds to the amino acid sequences of murine TdT and truncated murine TdT respectively. The variants of the invention may also be described directly with reference to SEQ ID numbers of corresponding reference sequences.

By "functionally equivalent residue" is meant a residue in a sequence of a TdT of sequence homologous to SEQ ID NO:1 or to SEQ ID NO:2 and having an identical functional role. Functionally equivalent residues are identified by using sequence alignments, for example, using the Mutalin line alignment software (http://multalin.toulouse.inra.fr/multalin/multalin.html; 1988, Nucl. Acids Res., 16 (22), 10881-10890). After alignment, the functionally equivalent residues are at homologous positions on the different sequences considered. Sequence alignments and identification of functionally equivalent residues may be between any TdT and their natural variants, including inter-species.

TdT can be found in many organisms or microorganisms. All those TdT are good candidates for performing the present invention. In particular, modifications to alter a particular TdT sequence to give said polymerase an increased ability to incorporate modified nucleotides, can target any other TdT sequence. Accordingly, mutations or combinations described herein by reference to SEQ ID NO:1, and more particularly to SEQ ID NO:2 that corresponds to amino acid residues 130 to 510 of SEQ ID NO:1, can be transposed to any other TdT sequence.

In some embodiments, the invention comprises a variant of Terminal deoxynucleotidyl Transferase (TdT) that (i) comprises an amino acid sequence having at least 80%, such as at least 85%, 90%, 95% or 99% identity with an amino acid sequence selected from SEQ ID NO: 2, 11, 13, 15, 17, 19, 21, 23, 25, 27, 29, 31, 33 or 35, with at least an amino acid substitution at position corresponding to a functionally equivalent residue of residue C173 with respect to SEQ ID NO:11, (ii) is able to synthesize a nucleic acid fragment without template and (iii) is able to incorporate a modified nucleoside triphosphate, such as a 3'-O-blocked nucleoside triphosphate, into the nucleic fragment.

Indeed, the inventors have discovered that such substitution has a great impact on both surface and interaction properties of the enzyme with nucleotides, which may allow incorporation of 3'O-modified nucleotides in a nucleic acid sequence.

Further embodiments of TdT variants of the invention are listed as entries in Tables 1A through 1C (single substitutions), Tables 2A through 2C (two substitutions), Tables 3A through 3C (three substitutions), and Tables 4A through 4F (four substitutions), wherein each such variant TdT is defined by the indicated SEQ ID NO in the righthand column modified by the substitution(s) listed in the lefthand column of the same row as the SEQ ID NO. A "non-wild type" substitution means that the substitution may be any amino acid except for the amino acid at the indicated position in the wild type sequence, or equivalently, the sequence of the indicated SEQ ID NO.

TABLE 1A

TdT variants at position C173 (SEQ ID NO: 2) or functionally equivalent positions of the indicated SEQ ID NO

| Non-wild type substitution at | SEQ ID NO |
| --- | --- |
| C173 | 2 |
| C313 | 10 |
| C173 | 11 |
| C302 | 12 |
| C173 | 13 |
| C302 | 14 |
| C172 | 15 |
| C304 | 16 |
| C173 | 17 |
| C304 | 18 |
| C173 | 19 |
| C293 | 20 |
| C173 | 21 |
| C282 | 22 |
| C178 | 23 |
| C304 | 24 |
| C174 | 25 |
| C300 | 26 |
| C171 | 27 |
| C305 | 28 |
| C173 | 29 |
| C302 | 30 |
| C173 | 31 |
| C313 | 32 |
| C182 | 33 |
| C271 | 34 |
| C176 | 35 |

TABLE 1B

Further TdT variants at position C173 (SEQ ID NO: 2) or functionally equivalent positions of the indicated SEQ ID NO

| Substitution | SEQ ID NO |
| --- | --- |
| C173/G/R/P/A/V/S/N/Q/D | 2 |
| C313/G/R/P/A/V/S/N/Q/D | 10 |
| C173/G/R/P/A/V/S/N/Q/D | 11 |
| C302/G/R/P/A/V/S/N/Q/D | 12 |
| C173/G/R/P/A/V/S/N/Q/D | 13 |
| C302/G/R/P/A/V/S/N/Q/D | 14 |
| C172/G/R/P/A/V/S/N/Q/D | 15 |
| C304/G/R/P/A/V/S/N/Q/D | 16 |
| C173/G/R/P/A/V/S/N/Q/D | 17 |
| C304/G/R/P/A/V/S/N/Q/D | 18 |
| C173/G/R/P/A/V/S/N/Q/D | 19 |
| C293/G/R/P/A/V/S/N/Q/D | 20 |
| C173/G/R/P/A/V/S/N/Q/D | 21 |
| C282/G/R/P/A/V/S/N/Q/D | 22 |
| C178/G/R/P/A/V/S/N/Q/D | 23 |
| C304/G/R/P/A/V/S/N/Q/D | 24 |
| C174/G/R/P/A/V/S/N/Q/D | 25 |
| C300/G/R/P/A/V/S/N/Q/D | 26 |
| C171/G/R/P/A/V/S/N/Q/D | 27 |
| C305/G/R/P/A/V/S/N/Q/D | 28 |
| C173/G/R/P/A/V/S/N/Q/D | 29 |
| C302/G/R/P/A/V/S/N/Q/D | 30 |
| C173/G/R/P/A/V/S/N/Q/D | 31 |
| C313/G/R/P/A/V/S/N/Q/D | 32 |
| C182/G/R/P/A/V/S/N/Q/D | 33 |
| C271/G/R/P/A/V/S/N/Q/D | 34 |
| C176/G/R/P/A/V/S/N/Q/D | 35 |

TABLE 1C

Further TdT variants at position C173 (SEQ ID NO: 2) or functionally equivalent positions of the indicated SEQ ID NO

| Substitutions | SEQ ID NO |
| --- | --- |
| C173/G/R | 2 |
| C313/G/R | 10 |
| C173/G/R | 11 |
| C302/G/R | 12 |
| C173/G/R | 13 |
| C302/G/R | 14 |
| C172/G/R | 15 |
| C304/G/R | 16 |
| C173/G/R | 17 |
| C304/G/R | 18 |
| C173/G/R | 19 |
| C293/G/R | 20 |
| C173/G/R | 21 |
| C282/G/R | 22 |
| C178/G/R | 23 |
| C304/G/R | 24 |
| C174/G/R | 25 |
| C300/G/R | 26 |
| C171/G/R | 27 |
| C305/G/R | 28 |
| C173/G/R | 29 |
| C302/G/R | 30 |
| C173/G/R | 31 |
| C313/G/R | 32 |
| C182/G/R | 33 |
| C271/G/R | 34 |
| C176/G/R | 35 |

TABLE 2A

Further TdT variants at position C173 (SEQ ID NO: 2) and position M63 (SEQ ID NO: 2) or functionally equivalent positions of the indicated SEQ ID NO

| Non-wildtype substitutions at locations | SEQ ID NO |
| --- | --- |
| M63 + C173 | 2 |
| M63 + C173 | 11 |
| M63 + C173 | 13 |
| L62 + C172 | 15 |
| M63 + C173 | 17 |
| M63 + C173 | 19 |
| R64 + C173 | 21 |
| M73 + C178 | 23 |
| M64 + C174 | 25 |
| M61 + C171 | 27 |
| M63 + C173 | 29 |

TABLE 2A-continued

Further TdT variants at position C173 (SEQ ID NO: 2) and position M63 (SEQ ID NO: 2) or functionally equivalent positions of the indicated SEQ ID NO

| Non-wildtype substitutions at locations | SEQ ID NO |
|---|---|
| L63 + C173 | 31 |
| M63 + C182 | 33 |
| M66 + C176 | 35 |

TABLE 2B

Further TdT variants at position C173 (SEQ ID NO: 2) and position M63 (SEQ ID NO: 2) or functionally equivalent positions of the indicated SEQ ID NO

| Substitutions and substitution positions | SEQ ID NO |
|---|---|
| M63R/Q/G/A/V/D/N/H/E + C173G/R/P/A/V/S/N/Q/D | 2 |
| M63R/Q/G/A/V/D/N/H/E + C173G/R/P/A/V/S/N/Q/D | 11 |
| M63R/Q/G/A/V/D/N/H/E + C173G/R/P/A/V/S/N/Q/D | 13 |
| L62R/Q/G/A/V/D/N/H/E + C172G/R/P/A/V/S/N/Q/D | 15 |
| M63R/Q/G/A/V/D/N/H/E + C173G/R/P/A/V/S/N/Q/D | 17 |
| M63R/Q/G/A/V/D/N/H/E + C173G/R/P/A/V/S/N/Q/D | 19 |
| R64R/Q/G/A/V/D/N/H/E + C173G/R/P/A/V/S/N/Q/D | 21 |
| M73R/Q/G/A/V/D/N/H/E + C178G/R/P/A/V/S/N/Q/D | 23 |
| M64R/Q/G/A/V/D/N/H/E + C174G/R/P/A/V/S/N/Q/D | 25 |
| M61R/Q/G/A/V/D/N/H/E + C171G/R/P/A/V/S/N/Q/D | 27 |
| M63R/Q/G/A/V/D/N/H/E + C173G/R/P/A/V/S/N/Q/D | 29 |
| L63R/Q/G/A/V/D/N/H/E + C173G/R/P/A/V/S/N/Q/D | 31 |
| M63R/Q/G/A/V/D/N/H/E + C182G/R/P/A/V/S/N/Q/D | 33 |
| M66R/Q/G/A/V/D/N/H/E + C176G/R/P/A/V/S/N/Q/D | 35 |

TABLE 2C

Further TdT variants at position C173 (SEQ ID NO: 2) and position M63 (SEQ ID NO: 2) or functionally equivalent positions of the indicated SEQ ID NO

| Substitutions and substitution positions | SEQ ID NO |
|---|---|
| M63R/Q + C173G/R | 2 |
| M63R/Q + C173G/R | 11 |
| M63R/Q + C173G/R | 13 |
| L62R/Q + C172G/R | 15 |
| M63R/Q + C173G/R | 17 |
| M63R/Q + C173G/R | 19 |
| R64R/Q + C173G/R | 21 |
| M73R/Q + C178G/R | 23 |
| M64R/Q + C174G/R | 25 |
| M61R/Q + C171G/R | 27 |
| M63R/Q + C173G/R | 29 |
| L63R/Q + C173G/R | 31 |
| M63R/Q + C182G/R | 33 |
| M66R/Q + C176G/R | 35 |

TABLE 3A

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63 + C173 + R207 | 2 |
| M63 + C173 + R207 | 11 |
| M63 + C173 + R207 | 13 |
| L62 + C172 + R206 | 15 |
| M63 + C173 + R207 | 17 |
| M63 + C173 + R207 | 19 |
| R64 + C173 + R208 | 21 |
| M73 + C178 + R207 | 23 |
| M64 + C174 + R208 | 25 |

TABLE 3A-continued

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M61 + C171 + R205 | 27 |
| M63 + C173 + R207 | 29 |
| L63 + C173 + R207 | 31 |
| M63 + C182 + R216 | 33 |
| M66 + C176 + R210 | 35 |

TABLE 3B

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207N/L/K/H/G/D/A/P | 2 |
| M63R/Q/G/A/V/D/N/H/E + C173G/R/P/A/V/S/N/Q/D + R207 N/L/K/H/G/D/A/P | 11 |
| M63R/Q/G/A/V/D/N/H/E + C173G/R/P/A/V/S/N/Q/D + R207 N/L/K/H/G/D/A/P | 13 |
| L62R/Q/G/A/V/D/N/H/E + C172G/R/P/A/V/S/N/Q/D + R206 N/L/K/H/G/D/A/P | 15 |
| M63R/Q/G/A/V/D/N/H/E + C173G/R/P/A/V/S/N/Q/D + R207 N/L/K/H/G/D/A/P | 17 |
| M63R/Q/G/A/V/D/N/H/E + C173G/R/P/A/V/S/N/Q/D + R207 N/L/K/H/G/D/A/P | 19 |
| R64Q/G/A/V/D/N/H/E + C173G/R/P/A/V/S/N/Q/D + R208 N/L/K/H/G/D/A/P | 21 |
| M73R/Q/G/A/V/D/N/H/E + C178G/R/P/A/V/S/N/Q/D + R207 N/L/K/H/G/D/A/P | 23 |
| M64R/Q/G/A/V/D/N/H/E + C174G/R/P/A/V/S/N/Q/D + R208 N/L/K/H/G/D/A/P | 25 |
| M61R/Q/G/A/V/D/N/H/E + C171G/R/P/A/V/S/N/Q/D + R205 N/L/K/H/G/D/A/P | 27 |
| M63R/Q/G/A/V/D/N/H/E + C173G/R/P/A/V/S/N/Q/D + R207 N/L/K/H/G/D/A/P | 29 |
| L63R/Q/G/A/V/D/N/H/E + C173G/R/P/A/V/S/N/Q/D + R207N/L/K/H/G/D/A/P | 31 |
| M63R/Q/G/A/V/D/N/H/E + C182G/R/P/A/V/S/N/Q/D 2 + R216N/L/K/H/G/D/A/P | 33 |
| M66R/Q/G/A/V/D/N/H/E + C176G/R/P/A/V/S/N/Q/D + R210N/L/K/H/G/D/A/P | 35 |

TABLE 3C

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63R/Q + C173G/R + R207L/N | 2 |
| M63R/Q + C173G/R + R207L/N | 11 |
| M63R/Q + C173G/R + R207L/N | 13 |
| M62R/Q + C172G/R + R206L/N | 15 |
| M63R/Q + C173G/R + R207L/N | 17 |
| M63R/Q + C173G/R + R207L/N | 19 |
| R64Q + C173G/R + R208L/N | 21 |
| M73R/Q + C178G/R + R207N/L | 23 |
| M64R/Q + C174G/R + R208 N/L | 25 |
| M61R/Q + C171G/R + R205N/L | 27 |
| M63R/Q + C173G/R + R207L/N | 29 |
| L63R/Q + C173G/R + R207L/N | 31 |
| M63R/Q + C182G/R + R216N/L | 33 |
| M66R/Q + C176G/R + R210N/L | 35 |

TABLE 4A

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63 + C173 + R207 + R325 | 2 |
| M63 + C173 + R207 + R324 | 11 |
| M63 + C173 + R207 + R324 | 13 |
| L62 + C172 + R206 + R320 | 15 |
| M63 + C173 + R207 + R331 | 17 |
| M63 + C173 + R207 + P325 | 19 |
| R64 + C173 + R208 + T331 | 21 |
| M73 + C178 + R207 + R325 | 23 |
| M64 + C174 + R208 + P326 | 25 |
| M61 + C171 + R205 + R323 | 27 |
| M63 + C173 + R207 + R328 | 29 |
| L63 + C173 + R207 + R325 | 31 |
| M63 + C182 + R216 + R338 | 33 |
| M66 + C176 + R210 + R328 | 35 |

TABLE 4B

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207N/L/K/H/G/D/A/P + R325P/N/A/L/K/H/G/D | 2 |
| M63R/Q/G/A/V/D/N/H/E + C173G/R/P/A/V/S/N/Q/D + R207 N/L/K/H/G/D/A/P + R324P/N/A/L/K/H/G/D | 11 |
| M63R/Q/G/A/V/D/N/H/E + C173G/R/P/A/V/S/N/Q/D + R207 N/L/K/H/G/D/A/P + R324P/N/A/L/K/H/G/D | 13 |
| L62R/Q/G/A/V/D/N/H/E + C172G/R/P/A/V/S/N/Q/D + R206 N/L/K/H/G/D/A/P + R320P/N/A/L/K/H/G/D | 15 |
| M63R/Q/G/A/V/D/N/H/E + C173G/R/P/A/V/S/N/Q/D + R207 N/L/K/H/G/D/A/P + R331P/N/A/L/K/H/G/D | 17 |
| M63R/Q/G/A/V/D/N/H/E + C173G/R/P/A/V/S/N/Q/D + R207 N/L/K/H/G/D/A/P + P325N/A/L/K/H/G/D | 19 |
| R64Q/G/A/V/D/N/H/E + C173G/R/P/A/V/S/N/Q/D + R208 N/L/K/H/G/D/A/P + T331P/N/A/L/K/H/G/D | 21 |
| M73R/Q/G/A/V/D/N/H/E + C178G/R/P/A/V/S/N/Q/D + R207 N/L/K/H/G/D/A/P + R325P/N/A/L/K/H/G/D | 23 |
| M64R/Q/G/A/V/D/N/H/E + C174G/R/P/A/V/S/N/Q/D + R208 N/L/K/H/G/D/A/P + P326N/A/L/K/H/G/D | 25 |
| M61R/Q/G/A/V/D/N/H/E + C171G/R/P/A/V/S/N/Q/D + R205 N/L/K/H/G/D/A/P + R323P/N/A/L/K/H/G/D | 27 |
| M63R/Q/G/A/V/D/N/H/E + C173G/R/P/A/V/S/N/Q/D + R207 N/L/K/H/G/D/A/P + R328P/N/A/L/K/H/G/D | 29 |
| L63R/Q/G/A/V/D/N/H/E + C173G/R/P/A/V/S/N/Q/D + R207N/L/K/H/G/D/A/P + R325P/N/A/L/K/H/G/D | 31 |
| M63R/Q/G/A/V/D/N/H/E + C182G/R/P/A/V/S/N/Q/D + R216N/L/K/H/G/D/A/P + R338P/N/A/L/K/H/G/D | 33 |
| M66R/Q/G/A/V/D/N/H/E + C176G/R/P/A/V/S/N/Q/D + R210N/L/K/H/G/D/A/P + R328P/N/A/L/K/H/G/D | 35 |

TABLE 4C

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63R/Q + C173G/R + R207N/L + R325P/N | 2 |
| M63R/Q + C173G/R + R207N/L + R324P/N | 11 |
| M63R/Q + C173G/R + R207N/L + R324P/N | 13 |
| L62R/Q + C172G/R + R206N/L + R320P/N | 15 |
| M63R/Q + C173G/R + R207N/L + R331P/N | 17 |
| M63R/Q + C173G/R + R207N/L + P325N | 19 |
| R64Q/G + C173G/R + R208N/L + T331P/N | 21 |
| M73R/Q/G + C178G/R + R207N/L + R325P/N | 23 |
| M64R/Q + C174G/R + R208N/L + P326N | 25 |
| M61R/Q + C171G/R + R205N/L + R323P/N | 27 |
| M63R/Q + C173G/R + R207N/L + R328P/N | 29 |
| L63R/Q + C173G/R + R207N/L + R325P/N | 31 |
| M63R/Q + C182G/R + R216N/L + R338P/N | 33 |
| M66R/Q + C176G/R + R210N/L + R328P/N | 35 |

TABLE 4D

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63 + C173 + R207 + E328 | 2 |
| M63 + C173 + R207 + E327 | 11 |
| M63 + C173 + R207 + E327 | 13 |
| L62 + C172 + R206 + G323 | 15 |
| M63 + C173 + R207 + E334 | 17 |
| M63 + C173 + R207 + E327 | 19 |
| R64 + C173 + R208 + E334 | 21 |
| M73 + C178 + R207 + E328 | 23 |
| M64 + C174 + R208 + E329 | 25 |
| M61 + C171 + R205 + E326 | 27 |
| M63 + C173 + R207 + E331 | 29 |
| L63 + C173 + R207 + E328 | 31 |
| M63 + C182 + R216 + E341 | 33 |
| M66 + C176 + R210 + E331 | 35 |

TABLE 4E

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207N/L/K/H/G/D/A/P + E328N/L/T/S | 2 |
| M63R/Q/G/A/V/D/N/H/E + C173G/R/P/A/V/S/N/Q/D + R207 N/L/K/H/G/D/A/P + E327N/L/T/S | 11 |
| M63R/Q/G/A/V/D/N/H/E + C173G/R/P/A/V/S/N/Q/D + R207 N/L/K/H/G/D/A/P + E327N/L/T/S | 13 |
| L62R/Q/G/A/V/D/N/H/E + C172G/R/P/A/V/S/N/Q/D + R206 N/L/K/H/G/D/A/P + G323N/L/T/S | 15 |
| M63R/Q/G/A/V/D/N/H/E + C173G/R/P/A/V/S/N/Q/D + R207 N/L/K/H/G/D/A/P + E334N/L/T/S | 17 |
| M63R/Q/G/A/V/D/N/H/E + C173G/R/P/A/V/S/N/Q/D + R207 N/L/K/H/G/D/A/P + E327N/L/T/S | 19 |
| R64Q/G/A/V/D/N/H/E + C173G/R/P/A/V/S/N/Q/D + R208 N/L/K/H/G/D/A/P + E334N/L/T/S | 21 |
| M73R/Q/G/A/V/D/N/H/E + C178G/R/P/A/V/S/N/Q/D + R207 N/L/K/H/G/D/A/P + E328N/L/T/S | 23 |
| M64R/Q/G/A/V/D/N/H/E + C174G/R/P/A/V/S/N/Q/D + R208 N/L/K/H/G/D/A/P + E329N/L/T/S | 25 |
| M61R/Q/G/A/V/D/N/H/E + C171G/R/P/A/V/S/N/Q/D + R205 N/L/K/H/G/D/A/P + E326N/L/T/S | 27 |
| M63R/Q/G/A/V/D/N/H/E + C173G/R/P/A/V/S/N/Q/D + R207 N/L/K/H/G/D/A/P + E331N/L/T/S | 29 |
| L63R/Q/G/A/V/D/N/H/E + C173G/R/P/A/V/S/N/Q/D + R207N/L/K/H/G/D/A/P + E328N/L/T/S | 31 |

TABLE 4E-continued

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63R/Q/G/A/V/D/N/H/E + C182G/R/P/A/V/S/N/Q/D + R216N/L/K/H/G/D/A/P + E341N/L/T/S | 33 |
| M66R/Q/G/A/V/D/N/H/E + C176G/R/P/A/V/S/N/Q/D + R210N/L/K/H/G/D/A/P + E331N/L/T/S | 35 |

TABLE 4F

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63R/Q + C173G/R + R207N/L + E328N/L/T/S | 2 |
| M63R/Q + C173G/R + R207 N/L + E327N/L/T/S | 11 |
| M63R/Q + C173G/R + R207N/L + E327N/L/T/S | 13 |
| L62R/Q + C172G/R + R206N/L + G323N/L/T/S | 15 |
| M63R/Q + C173G/R + R207N/L + E334N/L/T/S | 17 |
| M63R/Q + C173G/R + R207N/L + E327N/L/T/S | 19 |
| R64Q/G + C173G/R + R208N/L + E334N/L/T/S | 21 |
| M73R/Q + C178G/R + R207N/L + E328N/L/T/S | 23 |
| M64R/Q + C174G/R + R208N/L + E329N/L/T/S | 25 |
| M61R/Q + C171G/R + R205N/L + E326N/L/T/S | 27 |
| M63R/Q/G + C173G/R + R207N/L + E331N/L/T/S | 29 |
| L63R/Q + C173G/R + R207N/L + E328N/L/T/S | 31 |
| M63R/Q + C182G/R + R216N/L + E341N/L/T/S | 33 |
| M66R/Q + C176G/R + R210N/L + E331N/L/T/S | 35 |

Advantageously, the substitution is selected from CzzzG/R/P/A/V/S/N/Q/D, where Czzz represents an amino acid residue number functionally equivalent to C173 of SEQ ID NO:2 in SEQ ID NOs:11, 13, 15, 17, 19, 21, 23, 25, 27, 29, 31, 33 and 35, respectively, and such as from CzzzG/R, where Czzz represents an amino acid residue number functionally equivalent to C173 of SEQ ID NO: 2 in SEQ ID NOs:11, 13, 15, 17, 19, 21, 23, 25, 27, 29, 31, 33 and 35, respectively.

In a particular embodiment, the variant further comprises at least one amino acid substitution at position corresponding to functionally equivalent residues of residues selected from M63, R207, R324 and E327, of SEQ ID NO:11.

According to the invention, all variants of TdT as disclosed above are able to both synthesize a nucleic acid fragment without template and incorporate a modified nucleotide into the nucleic acid fragment. Advantageously, said variants have an increased ability to incorporate a modified nucleotide, such as a 3'O-modified nucleotide, into a nucleic acid fragment as compared to a TdT of SEQ ID NOs:2, 11, 13, 15, 17, 19, 21, 23, 25, 27, 29, 31, 33 and 35.

In some of the embodiments described above, the efficiency of a variant TdT in incorporating a 3'O-modified nucleoside triphosphate is at least 110 percent that of a wild type TdT of sequence SEQ ID NO:2, 11, 13, 15, 17, 19, 21, 23, 25, 27, 29, 31, 33 and 35 in other embodiments, the efficiency of a variant TdT in incorporating a 3'O-modified nucleoside triphosphate is at least 150 percent that of a wild type TdT of sequence SEQ ID NOs:2, 11, 13, 15, 17, 19, 21, 23, 25, 27, 29, 31, 33 and 35; in other embodiments, the efficiency of a variant TdT in incorporating a 3'O-modified nucleoside triphosphate is at least 200 percent that of a wild type TdT of sequence SEQ ID NOs:2, 11, 13, 15, 17, 19, 21, 23, 25, 27, 29, 31, 33 and 35.

The present invention further provides a variant of TdT having the amino acid sequence as set forth in SEQ ID NO:2 or functionally equivalent sequence, with at least one substitution or combination of substitutions as listed in Table 5 or Table 6. The variants of the invention comprise at least the amino acid substitutions listed in the left column and called "Variable Mutations", or functionally equivalent residues, and optionally one or both combination of substitutions listed in the right column and called "Optional Constant Mutations", or functionally equivalent sequence.

TABLE 5

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS1  | M63R + L131P + C173R + R207L + D250V + R325P + E328L | L52F + A108V + R354K and/or G284L/S + H287D + E289A |
| DS2  | M63R + L131P + C173R + R207L + D250V + R325P + E328N | L52F + A108V + R354K and/or G284L/S + H287D + E289A |
| DS3  | M63R + L131P + C173R + R207L + D250V + R325P | L52F + A108V + R354K and/or G284L/S + H287D + E289A |
| DS4  | M63R + L131P + C173R + R207L + D250V + R325A + E328L | L52F + A108V + R354K and/or G284L/S + H287D + E289A |
| DS5  | M63R + L131P + C173R + R207L + D250V + R325A + E328N | L52F + A108V + R354K and/or G284L/S + H287D + E289A |
| DS6  | M63R + L131P + C173R + R207L + D250V + R325A | L52F + A108V + R354K and/or G284L/S + H287D + E289A |
| DS7  | M63R + L131P + C173R + R207L + D250V + E328L | L52F + A108V + R354K and/or G284L/S + H287D + E289A |
| DS8  | M63R + L131P + C173R + R207L + D250V + E328N | L52F + A108V + R354K and/or G284L/S + H287D + E289A |
| DS9  | M63R + L131P + C173R + R207L + D250V | L52F + A108V + R354K and/or G284L/S + H287D + E289A |
| DS10 | M63R + L131P + C173R + R207L + R325P + E328L | L52F + A108V + R354K and/or G284L/S + H287D + E289A |
| DS11 | M63R + L131P + C173R + R207L + R325P + E328N | L52F + A108V + R354K and/or G284L/S + H287D + E289A |
| DS12 | M63R + L131P + C173R + R207L + R325P | L52F + A108V + R354K and/or G284L/S + H287D + E289A |
| DS13 | M63R + L131P + C173R + R207L + R325A + E328L | L52F + A108V + R354K and/or G284L/S + H287D + E289A |
| DS14 | M63R + L131P + C173R + R207L + R325A + E328N | L52F + A108V + R354K and/or G284L/S + H287D + E289A |
| DS15 | M63R + L131P + C173R + R207L + R325A | L52F + A108V + R354K and/or G284L/S + H287D + E289A |
| DS16 | M63R + L131P + C173R + R207L + E328L | L52F + A108V + R354K and/or G284L/S + H287D + E289A |
| DS17 | M63R + L131P + C173R + R207L + E328N | L52F + A108V + R354K and/or G284L/S + H287D + E289A |
| DS18 | M63R + L131P + C173R + R207L | L52F + A108V + R354K and/or G284L/S + H287D + E289A |
| DS19 | M63R + L131P + C173R + R207N + D250V + R325P + E328L | L52F + A108V + R354K and/or G284L/S + H287D + E289A |
| DS20 | M63R + L131P + C173R + R207N + D250V + R325P + E328N | L52F + A108V + R354K and/or G284L/S + H287D + E289A |
| DS21 | M63R + L131P + C173R + R207N + D250V + R325P | L52F + A108V + R354K and/or G284L/S + H287D + E289A |
| DS22 | M63R + L131P + C173R + R207N + D250V + R325A + E328L | L52F + A108V + R354K and/or G284L/S + H287D + E289A |
| DS23 | M63R + L131P + C173R + R207N + D250V + R325A + E328N | L52F + A108V + R354K and/or G284L/S + H287D + E289A |
| DS24 | M63R + L131P + C173R + R207N + D250V + R325A | L52F + A108V + R354K and/or G284L/S + H287D + E289A |
| DS25 | M63R + L131P + C173R + R207N + D250V + E328L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS26 | M63R + L131P + C173R + R207N + D250V + E328N | L52F + A108V + R354K and/or G284L/S + H287D + E289A |
| DS27 | M63R + L131P + C173R + R207N + D250V | L52F + A108V + R354K and/or G284L/S + H287D + E289A |
| DS28 | M63R + L131P + C173R + R207N + R325P + E328L | L52F + A108V + R354K and/or G284L/S + H287D + E289A |
| DS29 | M63R + L131P + C173R + R207N + R325P + E328N | L52F + A108V + R354K and/or G284L/S + H287D + E289A |
| DS30 | M63R + L131P + C173R + R207N + R325P | L52F + A108V + R354K and/or G284L/S + H287D + E289A |
| DS31 | M63R + L131P + C173R + R207N + R325A + E328L | L52F + A108V + R354K and/or G284L/S + H287D + E289A |
| DS32 | M63R + L131P + C173R + R207N + R325A + E328N | L52F + A108V + R354K and/or G284L/S + H287D + E289A |
| DS33 | M63R + L131P + C173R + R207N + R325A | L52F + A108V + R354K and/or G284L/S + H287D + E289A |
| DS34 | M63R + L131P + C173R + R207N + E328L | L52F + A108V + R354K and/or G284L/S + H287D + E289A |
| DS35 | M63R + L131P + C173R + R207N + E328N | L52F + A108V + R354K and/or G284L/S + H287D + E289A |
| DS36 | M63R + L131P + C173R + R207N | L52F + A108V + R354K and/or G284L/S + H287D + E289A |
| DS37 | M63R + L131P + C173R + D250V + R325P + E328L | L52F + A108V + R354K and/or G284L/S + H287D + E289A |
| DS38 | M63R + L131P + C173R + D250V + R325P + E328N | L52F + A108V + R354K and/or G284L/S + H287D + E289A |
| DS39 | M63R + L131P + C173R + D250V + R325P | L52F + A108V + R354K and/or G284L/S + H287D + E289A |
| DS40 | M63R + L131P + C173R + D250V + R325A + E328L | L52F + A108V + R354K and/or G284L/S + H287D + E289A |
| DS41 | M63R + L131P + C173R + D250V + R325A + E328N | L52F + A108V + R354K and/or G284L/S + H287D + E289A |
| DS42 | M63R + L131P + C173R + D250V + R325A | L52F + A108V + R354K and/or G284L/S + H287D + E289A |
| DS43 | M63R + L131P + C173R + D250V + E328L | L52F + A108V + R354K and/or G284L/S + H287D + E289A |
| DS44 | M63R + L131P + C173R + D250V + E328N | L52F + A108V + R354K and/or G284L/S + H287D + E289A |
| DS45 | M63R + L131P + C173R + D250V | L52F + A108V + R354K and/or G284L/S + H287D + E289A |
| DS46 | M63R + L131P + C173R + R325P + E328L | L52F + A108V + R354K and/or G284L/S + H287D + E289A |
| DS47 | M63R + L131P + C173R + R325P + E328N | L52F + A108V + R354K and/or G284L/S + H287D + E289A |
| DS48 | M63R + L131P + C173R + R325P | L52F + A108V + R354K and/or G284L/S + H287D + E289A |
| DS49 | M63R + L131P + C173R + R325A + E328L | L52F + A108V + R354K and/or G284L/S + H287D + E289A |
| DS50 | M63R + L131P + C173R + R325A + E328N | L52F + A108V + R354K and/or G284L/S + H287D + E289A |
| DS51 | M63R + L131P + C173R + R325A | L52F + A108V + R354K and/or G284L/S + H287D + E289A |
| DS52 | M63R + L131P + C173R + E328L | L52F + A108V + R354K and/or G284L/S + H287D + E289A |
| DS53 | M63R + L131P + C173R + E328N | L52F + A108V + R354K and/or G284L/S + H287D + E289A |
| DS54 | M63R + L131P + C173R | L52F + A108V + R354K and/or G284L/S + H287D + E289A |
| DS55 | M63R + L131P + C173G + R207L + D250V + R325P + E328L | L52F + A108V + R354K and/or G284L/S + H287D + E289A |
| DS56 | M63R + L131P + C173G + R207L + D250V + R325P + E328N | L52F + A108V + R354K and/or G284L/S + H287D + E289A |
| DS57 | M63R + L131P + C173G + R207L + D250V + R325P | L52F + A108V + R354K and/or G284L/S + H287D + E289A |
| DS58 | M63R + L131P + C173G + R207L + D250V + R325A + E328L | L52F + A108V + R354K and/or G284L/S + H287D + E289A |
| DS59 | M63R + L131P + C173G + R207L + D250V + R325A + E328N | L52F + A108V + R354K and/or G284L/S + H287D + E289A |
| DS60 | M63R + L131P + C173G + R207L + D250V + R325A | L52F + A108V + R354K and/or G284L/S + H287D + E289A |
| DS61 | M63R + L131P + C173G + R207L + D250V + E328L | L52F + A108V + R354K and/or G284L/S + H287D + E289A |
| DS62 | M63R + L131P + C173G + R207L + D250V + E328N | L52F + A108V + R354K and/or G284L/S + H287D + E289A |
| DS63 | M63R + L131P + C173G + R207L + D250V | L52F + A108V + R354K and/or G284L/S + H287D + E289A |
| DS64 | M63R + L131P + C173G + R207L + R325P + E328L | L52F + A108V + R354K and/or G284L/S + H287D + E289A |
| DS65 | M63R + L131P + C173G + R207L + R325P + E328N | L52F + A108V + R354K and/or G284L/S + H287D + E289A |
| DS66 | M63R + L131P + C173G + R207L + R325P | L52F + A108V + R354K and/or G284L/S + H287D + E289A |
| DS67 | M63R + L131P + C173G + R207L + R325A + E328L | L52F + A108V + R354K and/or G284L/S + H287D + E289A |
| DS68 | M63R + L131P + C173G + R207L + R325A + E328N | L52F + A108V + R354K and/or G284L/S + H287D + E289A |
| DS69 | M63R + L131P + C173G + R207L + R325A | L52F + A108V + R354K and/or G284L/S + H287D + E289A |
| DS70 | M63R + L131P + C173G + R207L + E328L | L52F + A108V + R354K and/or G284L/S + H287D + E289A |
| DS71 | M63R + L131P + C173G + R207L + E328N | L52F + A108V + R354K and/or G284L/S + H287D + E289A |
| DS72 | M63R + L131P + C173G + R207L | L52F + A108V + R354K and/or G284L/S + H287D + E289A |
| DS73 | M63R + L131P + C173G + R207N + D250V + R325P + E328L | L52F + A108V + R354K and/or G284L/S + H287D + E289A |
| DS74 | M63R + L131P + C173G + R207N + D250V + R325P + E328N | L52F + A108V + R354K and/or G284L/S + H287D + E289A |
| DS75 | M63R + L131P + C173G + R207N + D250V + R325P | L52F + A108V + R354K and/or G284L/S + H287D + E289A |
| DS76 | M63R + L131P + C173G + R207N + D250V + R325A + E328L | L52F + A108V + R354K and/or G284L/S + H287D + E289A |
| DS77 | M63R + L131P + C173G + R207N + D250V + R325A + E328N | L52F + A108V + R354K and/or G284L/S + H287D + E289A |
| DS78 | M63R + L131P + C173G + R207N + D250V + R325A | L52F + A108V + R354K and/or G284L/S + H287D + E289A |
| DS79 | M63R + L131P + C173G + R207N + D250V + E328L | L52F + A108V + R354K and/or G284L/S + H287D + E289A |
| DS80 | M63R + L131P + C173G + R207N + D250V + E328N | L52F + A108V + R354K and/or G284L/S + H287D + E289A |
| DS81 | M63R + L131P + C173G + R207N + D250V | L52F + A108V + R354K and/or G284L/S + H287D + E289A |
| DS82 | M63R + L131P + C173G + R207N + R325P + E328L | L52F + A108V + R354K and/or G284L/S + H287D + E289A |
| DS83 | M63R + L131P + C173G + R207N + R325P + E328N | L52F + A108V + R354K and/or G284L/S + H287D + E289A |
| DS84 | M63R + L131P + C173G + R207N + R325P | L52F + A108V + R354K and/or G284L/S + H287D + E289A |
| DS85 | M63R + L131P + C173G + R207N + R325A + E328L | L52F + A108V + R354K and/or G284L/S + H287D + E289A |
| DS86 | M63R + L131P + C173G + R207N + R325A + E328N | L52F + A108V + R354K and/or G284L/S + H287D + E289A |
| DS87 | M63R + L131P + C173G + R207N + R325A | L52F + A108V + R354K and/or G284L/S + H287D + E289A |
| DS88 | M63R + L131P + C173G + R207N + E328L | L52F + A108V + R354K and/or G284L/S + H287D + E289A |
| DS89 | M63R + L131P + C173G + R207N + E328N | L52F + A108V + R354K and/or G284L/S + H287D + E289A |
| DS90 | M63R + L131P + C173G + R207N | L52F + A108V + R354K and/or G284L/S + H287D + E289A |
| DS91 | M63R + L131P + C173G + D250V + R325P + E328L | L52F + A108V + R354K and/or G284L/S + H287D + E289A |
| DS92 | M63R + L131P + C173G + D250V + R325P + E328N | L52F + A108V + R354K and/or G284L/S + H287D + E289A |
| DS93 | M63R + L131P + C173G + D250V + R325P | L52F + A108V + R354K and/or G284L/S + H287D + E289A |
| DS94 | M63R + L131P + C173G + D250V + R325A + E328L | L52F + A108V + R354K and/or G284L/S + H287D + E289A |
| DS95 | M63R + L131P + C173G + D250V + R325A + E328N | L52F + A108V + R354K and/or G284L/S + H287D + E289A |
| DS96 | M63R + L131P + C173G + D250V + R325A | L52F + A108V + R354K and/or G284L/S + H287D + E289A |
| DS97 | M63R + L131P + C173G + D250V + E328L | L52F + A108V + R354K and/or G284L/S + H287D + E289A |
| DS98 | M63R + L131P + C173G + D250V + E328N | L52F + A108V + R354K and/or G284L/S + H287D + E289A |
| DS99 | M63R + L131P + C173G + D250V | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS100 | M63R + L131P + C173G + R325P + E328L | L52F + A108V + R354K and/or G284L/S + H287D + E289A |
| DS101 | M63R + L131P + C173G + R325P + E328N | L52F + A108V + R354K and/or G284L/S + H287D + E289A |
| DS102 | M63R + L131P + C173G + R325P | L52F + A108V + R354K and/or G284L/S + H287D + E289A |
| DS103 | M63R + L131P + C173G + R325A + E328L | L52F + A108V + R354K and/or G284L/S + H287D + E289A |
| DS104 | M63R + L131P + C173G + R325A + E328N | L52F + A108V + R354K and/or G284L/S + H287D + E289A |
| DS105 | M63R + L131P + C173G + R325A | L52F + A108V + R354K and/or G284L/S + H287D + E289A |
| DS106 | M63R + L131P + C173G + E328L | L52F + A108V + R354K and/or G284L/S + H287D + E289A |
| DS107 | M63R + L131P + C173G + E328N | L52F + A108V + R354K and/or G284L/S + H287D + E289A |
| DS108 | M63R + L131P + C173G | L52F + A108V + R354K and/or G284L/S + H287D + E289A |
| DS163 | M63R + C173R + R207L + D250V + R325P + E328L | L52F + A108V + R354K and/or G284L/S + H287D + E289A |
| DS164 | M63R + C173R + R207L + D250V + R325P + E328N | L52F + A108V + R354K and/or G284L/S + H287D + E289A |
| DS165 | M63R + C173R + R207L + D250V + R325P | L52F + A108V + R354K and/or G284L/S + H287D + E289A |
| DS166 | M63R + C173R + R207L + D250V + R325A + E328L | L52F + A108V + R354K and/or G284L/S + H287D + E289A |
| DS167 | M63R + C173R + R207L + D250V + R325A + E328N | L52F + A108V + R354K and/or G284L/S + H287D + E289A |
| DS168 | M63R + C173R + R207L + D250V + R325A | L52F + A108V + R354K and/or G284L/S + H287D + E289A |
| DS169 | M63R + C173R + R207L + D250V + E328L | L52F + A108V + R354K and/or G284L/S + H287D + E289A |
| DS170 | M63R + C173R + R207L + D250V + E328N | L52F + A108V + R354K and/or G284L/S + H287D + E289A |
| DS171 | M63R + C173R + R207L + D250V | L52F + A108V + R354K and/or G284L/S + H287D + E289A |
| DS172 | M63R + C173R + R207L + R325P + E328L | L52F + A108V + R354K and/or G284L/S + H287D + E289A |
| DS173 | M63R + C173R + R207L + R325P + E328N | L52F + A108V + R354K and/or G284L/S + H287D + E289A |
| DS174 | M63R + C173R + R207L + R325P | L52F + A108V + R354K and/or G284L/S + H287D + E289A |
| DS175 | M63R + C173R + R207L + R325A + E328L | L52F + A108V + R354K and/or G284L/S + H287D + E289A |
| DS176 | M63R + C173R + R207L + R325A + E328N | L52F + A108V + R354K and/or G284L/S + H287D + E289A |
| DS177 | M63R + C173R + R207L + R325A | L52F + A108V + R354K and/or G284L/S + H287D + E289A |
| DS178 | M63R + C173R + R207L + E328L | L52F + A108V + R354K and/or G284L/S + H287D + E289A |
| DS179 | M63R + C173R + R207L + E328N | L52F + A108V + R354K and/or G284L/S + H287D + E289A |
| DS180 | M63R + C173R + R207L | L52F + A108V + R354K and/or G284L/S + H287D + E289A |
| DS52 | M63R + C173R + R207N + D250V + R325P + E328L | L52F + A108V + R354K and/or G284L/S + H287D + E289A |
| DS182 | M63R + C173R + R207N + D250V + R325P + E328N | L52F + A108V + R354K and/or G284L/S + H287D + E289A |
| DS183 | M63R + C173R + R207N + D250V + R325P | L52F + A108V + R354K and/or G284L/S + H287D + E289A |
| DS184 | M63R + C173R + R207N + D250V + R325A + E328L | L52F + A108V + R354K and/or G284L/S + H287D + E289A |
| DS185 | M63R + C173R + R207N + D250V + R325A + E328N | L52F + A108V + R354K and/or G284L/S + H287D + E289A |
| DS186 | M63R + C173R + R207N + D250V + R325A | L52F + A108V + R354K and/or G284L/S + H287D + E289A |
| DS187 | M63R + C173R + R207N + D250V + E328L | L52F + A108V + R354K and/or G284L/S + H287D + E289A |
| DS188 | M63R + C173R + R207N + D250V + E328N | L52F + A108V + R354K and/or G284L/S + H287D + E289A |
| DS189 | M63R + C173R + R207N + D250V | L52F + A108V + R354K and/or G284L/S + H287D + E289A |
| DS190 | M63R + C173R + R207N + R325P + E328L | L52F + A108V + R354K and/or G284L/S + H287D + E289A |
| DS191 | M63R + C173R + R207N + R325P + E328N | L52F + A108V + R354K and/or G284L/S + H287D + E289A |
| DS63 | M63R + C173R + R207N + R325P | L52F + A108V + R354K and/or G284L/S + H287D + E289A |
| DS193 | M63R + C173R + R207N + R325A + E328L | L52F + A108V + R354K and/or G284L/S + H287D + E289A |
| DS194 | M63R + C173R + R207N + R325A + E328N | L52F + A108V + R354K and/or G284L/S + H287D + E289A |
| DS195 | M63R + C173R + R207N + R325A | L52F + A108V + R354K and/or G284L/S + H287D + E289A |
| DS196 | M63R + C173R + R207N + E328L | L52F + A108V + R354K and/or G284L/S + H287D + E289A |
| DS197 | M63R + C173R + R207N + E328N | L52F + A108V + R354K and/or G284L/S + H287D + E289A |
| DS198 | M63R + C173R + R207N | L52F + A108V + R354K and/or G284L/S + H287D + E289A |
| DS199 | M63R + C173R + D250V + R325P + E328L | L52F + A108V + R354K and/or G284L/S + H287D + E289A |
| DS200 | M63R + C173R + D250V + R325P + E328N | L52F + A108V + R354K and/or G284L/S + H287D + E289A |
| DS201 | M63R + C173R + D250V + R325P | L52F + A108V + R354K and/or G284L/S + H287D + E289A |
| DS202 | M63R + C173R + D250V + R325A + E328L | L52F + A108V + R354K and/or G284L/S + H287D + E289A |
| DS203 | M63R + C173R + D250V + R325A + E328N | L52F + A108V + R354K and/or G284L/S + H287D + E289A |
| DS204 | M63R + C173R + D250V + R325A | L52F + A108V + R354K and/or G284L/S + H287D + E289A |
| DS205 | M63R + C173R + D250V + E328L | L52F + A108V + R354K and/or G284L/S + H287D + E289A |
| DS206 | M63R + C173R + D250V + E328N | L52F + A108V + R354K and/or G284L/S + H287D + E289A |
| DS207 | M63R + C173R + D250V | L52F + A108V + R354K and/or G284L/S + H287D + E289A |
| DS208 | M63R + C173R + R325P + E328L | L52F + A108V + R354K and/or G284L/S + H287D + E289A |
| DS209 | M63R + C173R + R325P + E328N | L52F + A108V + R354K and/or G284L/S + H287D + E289A |
| DS210 | M63R + C173R + R325P | L52F + A108V + R354K and/or G284L/S + H287D + E289A |
| DS211 | M63R + C173R + R325A + E328L | L52F + A108V + R354K and/or G284L/S + H287D + E289A |
| DS212 | M63R + C173R + R325A + E328N | L52F + A108V + R354K and/or G284L/S + H287D + E289A |
| DS213 | M63R + C173R + R325A | L52F + A108V + R354K and/or G284L/S + H287D + E289A |
| DS214 | M63R + C173R + E328L | L52F + A108V + R354K and/or G284L/S + H287D + E289A |
| DS215 | M63R + C173R + E328N | L52F + A108V + R354K and/or G284L/S + H287D + E289A |
| DS216 | M63R + C173R | L52F + A108V + R354K and/or G284L/S + H287D + E289A |
| DS217 | M63R + C173G + R207L + D250V + R325P + E328L | L52F + A108V + R354K and/or G284L/S + H287D + E289A |
| DS218 | M63R + C173G + R207L + D250V + R325P + E328N | L52F + A108V + R354K and/or G284L/S + H287D + E289A |
| DS219 | M63R + C173G + R207L + D250V + R325P | L52F + A108V + R354K and/or G284L/S + H287D + E289A |
| DS220 | M63R + C173G + R207L + D250V + R325A + E328L | L52F + A108V + R354K and/or G284L/S + H287D + E289A |
| DS221 | M63R + C173G + R207L + D250V + R325A + E328N | L52F + A108V + R354K and/or G284L/S + H287D + E289A |
| DS222 | M63R + C173G + R207L + D250V + R325A | L52F + A108V + R354K and/or G284L/S + H287D + E289A |
| DS223 | M63R + C173G + R207L + D250V + E328L | L52F + A108V + R354K and/or G284L/S + H287D + E289A |
| DS224 | M63R + C173G + R207L + D250V + E328N | L52F + A108V + R354K and/or G284L/S + H287D + E289A |
| DS225 | M63R + C173G + R207L + D250V | L52F + A108V + R354K and/or G284L/S + H287D + E289A |
| DS226 | M63R + C173G + R207L + R325P + E328L | L52F + A108V + R354K and/or G284L/S + H287D + E289A |
| DS227 | M63R + C173G + R207L + R325P + E328N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS228 | M63R + C173G + R207L + R325P | L52F + A108V + R354K and/or G284L/S + H287D + E289A |
| DS229 | M63R + C173G + R207L + R325A + E328L | L52F + A108V + R354K and/or G284L/S + H287D + E289A |
| DS230 | M63R + C173G + R207L + R325A + E328N | L52F + A108V + R354K and/or G284L/S + H287D + E289A |
| DS231 | M63R + C173G + R207L + R325A | L52F + A108V + R354K and/or G284L/S + H287D + E289A |
| DS232 | M63R + C173G + R207L + E328L | L52F + A108V + R354K and/or G284L/S + H287D + E289A |
| DS233 | M63R + C173G + R207L + E328N | L52F + A108V + R354K and/or G284L/S + H287D + E289A |
| DS234 | M63R + C173G + R207L | L52F + A108V + R354K and/or G284L/S + H287D + E289A |
| DS235 | M63R + C173G + R207N + D250V + R325P + E328L | L52F + A108V + R354K and/or G284L/S + H287D + E289A |
| DS236 | M63R + C173G + R207N + D250V + R325P + E328N | L52F + A108V + R354K and/or G284L/S + H287D + E289A |
| DS108 | M63R + C173G + R207N + D250V + R325P | L52F + A108V + R354K and/or G284L/S + H287D + E289A |
| DS238 | M63R + C173G + R207N + D250V + R325A + E328L | L52F + A108V + R354K and/or G284L/S + H287D + E289A |
| DS239 | M63R + C173G + R207N + D250V + R325A + E328N | L52F + A108V + R354K and/or G284L/S + H287D + E289A |
| DS240 | M63R + C173G + R207N + D250V + R325A | L52F + A108V + R354K and/or G284L/S + H287D + E289A |
| DS241 | M63R + C173G + R207N + D250V + E328L | L52F + A108V + R354K and/or G284L/S + H287D + E289A |
| DS242 | M63R + C173G + R207N + D250V + E328N | L52F + A108V + R354K and/or G284L/S + H287D + E289A |
| DS243 | M63R + C173G + R207N + D250V | L52F + A108V + R354K and/or G284L/S + H287D + E289A |
| DS244 | M63R + C173G + R207N + R325P + E328L | L52F + A108V + R354K and/or G284L/S + H287D + E289A |
| DS245 | M63R + C173G + R207N + R325P + E328N | L52F + A108V + R354K and/or G284L/S + H287D + E289A |
| DS246 | M63R + C173G + R207N + R325P | L52F + A108V + R354K and/or G284L/S + H287D + E289A |
| DS247 | M63R + C173G + R207N + R325A + E328L | L52F + A108V + R354K and/or G284L/S + H287D + E289A |
| DS248 | M63R + C173G + R207N + R325A + E328N | L52F + A108V + R354K and/or G284L/S + H287D + E289A |
| DS249 | M63R + C173G + R207N + R325A | L52F + A108V + R354K and/or G284L/S + H287D + E289A |
| DS250 | M63R + C173G + R207N + E328L | L52F + A108V + R354K and/or G284L/S + H287D + E289A |
| DS251 | M63R + C173G + R207N + E328N | L52F + A108V + R354K and/or G284L/S + H287D + E289A |
| DS252 | M63R + C173G + R207N | L52F + A108V + R354K and/or G284L/S + H287D + E289A |
| DS253 | M63R + C173G + D250V + R325P + E328L | L52F + A108V + R354K and/or G284L/S + H287D + E289A |
| DS254 | M63R + C173G + D250V + R325P + E328N | L52F + A108V + R354K and/or G284L/S + H287D + E289A |
| DS255 | M63R + C173G + D250V + R325P | L52F + A108V + R354K and/or G284L/S + H287D + E289A |
| DS256 | M63R + C173G + D250V + R325A + E328L | L52F + A108V + R354K and/or G284L/S + H287D + E289A |
| DS257 | M63R + C173G + D250V + R325A + E328N | L52F + A108V + R354K and/or G284L/S + H287D + E289A |
| DS258 | M63R + C173G + D250V + R325A | L52F + A108V + R354K and/or G284L/S + H287D + E289A |
| DS259 | M63R + C173G + D250V + E328L | L52F + A108V + R354K and/or G284L/S + H287D + E289A |
| DS131 | M63R + C173G + D250V + E328N | L52F + A108V + R354K and/or G284L/S + H287D + E289A |
| DS261 | M63R + C173G + D250V | L52F + A108V + R354K and/or G284L/S + H287D + E289A |
| DS262 | M63R + C173G + R325P + E328L | L52F + A108V + R354K and/or G284L/S + H287D + E289A |
| DS263 | M63R + C173G + R325P + E328N | L52F + A108V + R354K and/or G284L/S + H287D + E289A |
| DS264 | M63R + C173G + R325P | L52F + A108V + R354K and/or G284L/S + H287D + E289A |
| DS265 | M63R + C173G + R325A + E328L | L52F + A108V + R354K and/or G284L/S + H287D + E289A |
| DS266 | M63R + C173G + R325A + E328N | L52F + A108V + R354K and/or G284L/S + H287D + E289A |
| DS267 | M63R + C173G + R325A | L52F + A108V + R354K and/or G284L/S + H287D + E289A |
| DS268 | M63R + C173G + E328L | L52F + A108V + R354K and/or G284L/S + H287D + E289A |
| DS269 | M63R + C173G + E328N | L52F + A108V + R354K and/or G284L/S + H287D + E289A |
| DS270 | M63R + C173G | L52F + A108V + R354K and/or G284L/S + H287D + E289A |
| DS325 | M63Q + L131P + C173R + R207L + D250V + R325P + E328L | L52F + A108V + R354K and/or G284L/S + H287D + E289A |
| DS326 | M63Q + L131P + C173R + R207L + D250V + R325P + E328N | L52F + A108V + R354K and/or G284L/S + H287D + E289A |
| DS327 | M63Q + L131P + C173R + R207L + D250V + R325P | L52F + A108V + R354K and/or G284L/S + H287D + E289A |
| DS328 | M63Q + L131P + C173R + R207L + D250V + R325A + E328L | L52F + A108V + R354K and/or G284L/S + H287D + E289A |
| DS329 | M63Q + L131P + C173R + R207L + D250V + R325A + E328N | L52F + A108V + R354K and/or G284L/S + H287D + E289A |
| DS330 | M63Q + L131P + C173R + R207L + D250V + R325A | L52F + A108V + R354K and/or G284L/S + H287D + E289A |
| DS331 | M63Q + L131P + C173R + R207L + D250V + E328L | L52F + A108V + R354K and/or G284L/S + H287D + E289A |
| DS332 | M63Q + L131P + C173R + R207L + D250V + E328N | L52F + A108V + R354K and/or G284L/S + H287D + E289A |
| DS333 | M63Q + L131P + C173R + R207L + D250V | L52F + A108V + R354K and/or G284L/S + H287D + E289A |
| DS334 | M63Q + L131P + C173R + R207L + R325P + E328L | L52F + A108V + R354K and/or G284L/S + H287D + E289A |
| DS335 | M63Q + L131P + C173R + R207L + R325P + E328N | L52F + A108V + R354K and/or G284L/S + H287D + E289A |
| DS207 | M63Q + L131P + C173R + R207L + R325P | L52F + A108V + R354K and/or G284L/S + H287D + E289A |
| DS337 | M63Q + L131P + C173R + R207L + R325A + E328L | L52F + A108V + R354K and/or G284L/S + H287D + E289A |
| DS338 | M63Q + L131P + C173R + R207L + R325A + E328N | L52F + A108V + R354K and/or G284L/S + H287D + E289A |
| DS339 | M63Q + L131P + C173R + R207L + R325A | L52F + A108V + R354K and/or G284L/S + H287D + E289A |
| DS340 | M63Q + L131P + C173R + R207L + E328L | L52F + A108V + R354K and/or G284L/S + H287D + E289A |
| DS341 | M63Q + L131P + C173R + R207L + E328N | L52F + A108V + R354K and/or G284L/S + H287D + E289A |
| DS342 | M63Q + L131P + C173R + R207L | L52F + A108V + R354K and/or G284L/S + H287D + E289A |
| DS343 | M63Q + L131P + C173R + R207N + D250V + R325P + E328L | L52F + A108V + R354K and/or G284L/S + H287D + E289A |
| DS344 | M63Q + L131P + C173R + R207N + D250V + R325P + E328N | L52F + A108V + R354K and/or G284L/S + H287D + E289A |
| DS345 | M63Q + L131P + C173R + R207N + D250V + R325P | L52F + A108V + R354K and/or G284L/S + H287D + E289A |
| DS346 | M63Q + L131P + C173R + R207N + D250V + R325A + E328L | L52F + A108V + R354K and/or G284L/S + H287D + E289A |
| DS347 | M63Q + L131P + C173R + R207N + D250V + R325A + E328N | L52F + A108V + R354K and/or G284L/S + H287D + E289A |
| DS348 | M63Q + L131P + C173R + R207N + D250V + R325A | L52F + A108V + R354K and/or G284L/S + H287D + E289A |
| DS349 | M63Q + L131P + C173R + R207N + D250V + E328L | L52F + A108V + R354K and/or G284L/S + H287D + E289A |
| DS350 | M63Q + L131P + C173R + R207N + D250V + E328N | L52F + A108V + R354K and/or G284L/S + H287D + E289A |
| DS351 | M63Q + L131P + C173R + R207N + D250V | L52F + A108V + R354K and/or G284L/S + H287D + E289A |
| DS352 | M63Q + L131P + C173R + R207N + R325P + E328L | L52F + A108V + R354K and/or G284L/S + H287D + E289A |
| DS353 | M63Q + L131P + C173R + R207N + R325P + E328N | L52F + A108V + R354K and/or G284L/S + H287D + E289A |
| DS354 | M63Q + L131P + C173R + R207N + R325P | L52F + A108V + R354K and/or G284L/S + H287D + E289A |
| DS355 | M63Q + L131P + C173R + R207N + R325A + E328L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS356 | M63Q + L131P + C173R + R207N + R325A + E328N | L52F + A108V + R354K and/or G284L/S + H287D + E289A |
| DS357 | M63Q + L131P + C173R + R207N + R325A | L52F + A108V + R354K and/or G284L/S + H287D + E289A |
| DS358 | M63Q + L131P + C173R + R207N + E328L | L52F + A108V + R354K and/or G284L/S + H287D + E289A |
| DS359 | M63Q + L131P + C173R + R207N + E328N | L52F + A108V + R354K and/or G284L/S + H287D + E289A |
| DS360 | M63Q + L131P + C173R + R207N | L52F + A108V + R354K and/or G284L/S + H287D + E289A |
| DS361 | M63Q + L131P + C173R + D250V + R325P + E328L | L52F + A108V + R354K and/or G284L/S + H287D + E289A |
| DS362 | M63Q + L131P + C173R + D250V + R325P + E328N | L52F + A108V + R354K and/or G284L/S + H287D + E289A |
| DS363 | M63Q + L131P + C173R + D250V + R325P | L52F + A108V + R354K and/or G284L/S + H287D + E289A |
| DS364 | M63Q + L131P + C173R + D250V + R325A + E328L | L52F + A108V + R354K and/or G284L/S + H287D + E289A |
| DS365 | M63Q + L131P + C173R + D250V + R325A + E328N | L52F + A108V + R354K and/or G284L/S + H287D + E289A |
| DS366 | M63Q + L131P + C173R + D250V + R325A | L52F + A108V + R354K and/or G284L/S + H287D + E289A |
| DS367 | M63Q + L131P + C173R + D250V + E328L | L52F + A108V + R354K and/or G284L/S + H287D + E289A |
| DS368 | M63Q + L131P + C173R + D250V + E328N | L52F + A108V + R354K and/or G284L/S + H287D + E289A |
| DS369 | M63Q + L131P + C173R + D250V | L52F + A108V + R354K and/or G284L/S + H287D + E289A |
| DS370 | M63Q + L131P + C173R + R325P + E328L | L52F + A108V + R354K and/or G284L/S + H287D + E289A |
| DS371 | M63Q + L131P + C173R + R325P + E328N | L52F + A108V + R354K and/or G284L/S + H287D + E289A |
| DS372 | M63Q + L131P + C173R + R325P | L52F + A108V + R354K and/or G284L/S + H287D + E289A |
| DS373 | M63Q + L131P + C173R + R325A + E328L | L52F + A108V + R354K and/or G284L/S + H287D + E289A |
| DS374 | M63Q + L131P + C173R + R325A + E328N | L52F + A108V + R354K and/or G284L/S + H287D + E289A |
| DS375 | M63Q + L131P + C173R + R325A | L52F + A108V + R354K and/or G284L/S + H287D + E289A |
| DS376 | M63Q + L131P + C173R + E328L | L52F + A108V + R354K and/or G284L/S + H287D + E289A |
| DS377 | M63Q + L131P + C173R + E328N | L52F + A108V + R354K and/or G284L/S + H287D + E289A |
| DS378 | M63Q + L131P + C173R | L52F + A108V + R354K and/or G284L/S + H287D + E289A |
| DS250 | M63Q + L131P + C173G + R207L + D250V + R325P + E328L | L52F + A108V + R354K and/or G284L/S + H287D + E289A |
| DS380 | M63Q + L131P + C173G + R207L + D250V + R325P + E328N | L52F + A108V + R354K and/or G284L/S + H287D + E289A |
| DS381 | M63Q + L131P + C173G + R207L + D250V + R325P | L52F + A108V + R354K and/or G284L/S + H287D + E289A |
| DS382 | M63Q + L131P + C173G + R207L + D250V + R325A + E328L | L52F + A108V + R354K and/or G284L/S + H287D + E289A |
| DS383 | M63Q + L131P + C173G + R207L + D250V + R325A + E328N | L52F + A108V + R354K and/or G284L/S + H287D + E289A |
| DS384 | M63Q + L131P + C173G + R207L + D250V + R325A | L52F + A108V + R354K and/or G284L/S + H287D + E289A |
| DS385 | M63Q + L131P + C173G + R207L + D250V + E328L | L52F + A108V + R354K and/or G284L/S + H287D + E289A |
| DS386 | M63Q + L131P + C173G + R207L + D250V + E328N | L52F + A108V + R354K and/or G284L/S + H287D + E289A |
| DS387 | M63Q + L131P + C173G + R207L + D250V | L52F + A108V + R354K and/or G284L/S + H287D + E289A |
| DS388 | M63Q + L131P + C173G + R207L + R325P + E328L | L52F + A108V + R354K and/or G284L/S + H287D + E289A |
| DS389 | M63Q + L131P + C173G + R207L + R325P + E328N | L52F + A108V + R354K and/or G284L/S + H287D + E289A |
| DS390 | M63Q + L131P + C173G + R207L + R325P | L52F + A108V + R354K and/or G284L/S + H287D + E289A |
| DS391 | M63Q + L131P + C173G + R207L + R325A + E328L | L52F + A108V + R354K and/or G284L/S + H287D + E289A |
| DS392 | M63Q + L131P + C173G + R207L + R325A + E328N | L52F + A108V + R354K and/or G284L/S + H287D + E289A |
| DS393 | M63Q + L131P + C173G + R207L + R325A | L52F + A108V + R354K and/or G284L/S + H287D + E289A |
| DS394 | M63Q + L131P + C173G + R207L + E328L | L52F + A108V + R354K and/or G284L/S + H287D + E289A |
| DS395 | M63Q + L131P + C173G + R207L + E328N | L52F + A108V + R354K and/or G284L/S + H287D + E289A |
| DS396 | M63Q + L131P + C173G + R207L | L52F + A108V + R354K and/or G284L/S + H287D + E289A |
| DS397 | M63Q + L131P + C173G + R207N + D250V + R325P + E328L | L52F + A108V + R354K and/or G284L/S + H287D + E289A |
| DS398 | M63Q + L131P + C173G + R207N + D250V + R325P + E328N | L52F + A108V + R354K and/or G284L/S + H287D + E289A |
| DS399 | M63Q + L131P + C173G + R207N + D250V + R325P | L52F + A108V + R354K and/or G284L/S + H287D + E289A |
| DS400 | M63Q + L131P + C173G + R207N + D250V + R325A + E328L | L52F + A108V + R354K and/or G284L/S + H287D + E289A |
| DS401 | M63Q + L131P + C173G + R207N + D250V + R325A + E328N | L52F + A108V + R354K and/or G284L/S + H287D + E289A |
| DS402 | M63Q + L131P + C173G + R207N + D250V + R325A | L52F + A108V + R354K and/or G284L/S + H287D + E289A |
| DS403 | M63Q + L131P + C173G + R207N + D250V + E328L | L52F + A108V + R354K and/or G284L/S + H287D + E289A |
| DS404 | M63Q + L131P + C173G + R207N + D250V + E328N | L52F + A108V + R354K and/or G284L/S + H287D + E289A |
| DS405 | M63Q + L131P + C173G + R207N + D250V | L52F + A108V + R354K and/or G284L/S + H287D + E289A |
| DS406 | M63Q + L131P + C173G + R207N + R325P + E328L | L52F + A108V + R354K and/or G284L/S + H287D + E289A |
| DS407 | M63Q + L131P + C173G + R207N + R325P + E328N | L52F + A108V + R354K and/or G284L/S + H287D + E289A |
| DS408 | M63Q + L131P + C173G + R207N + R325P | L52F + A108V + R354K and/or G284L/S + H287D + E289A |
| DS409 | M63Q + L131P + C173G + R207N + R325A + E328L | L52F + A108V + R354K and/or G284L/S + H287D + E289A |
| DS410 | M63Q + L131P + C173G + R207N + R325A + E328N | L52F + A108V + R354K and/or G284L/S + H287D + E289A |
| DS411 | M63Q + L131P + C173G + R207N + R325A | L52F + A108V + R354K and/or G284L/S + H287D + E289A |
| DS412 | M63Q + L131P + C173G + R207N + E328L | L52F + A108V + R354K and/or G284L/S + H287D + E289A |
| DS284 | M63Q + L131P + C173G + R207N + E328N | L52F + A108V + R354K and/or G284L/S + H287D + E289A |
| DS414 | M63Q + L131P + C173G + R207N | L52F + A108V + R354K and/or G284L/S + H287D + E289A |
| DS415 | M63Q + L131P + C173G + D250V + R325P + E328L | L52F + A108V + R354K and/or G284L/S + H287D + E289A |
| DS287 | M63Q + L131P + C173G + D250V + R325P + E328N | L52F + A108V + R354K and/or G284L/S + H287D + E289A |
| DS417 | M63Q + L131P + C173G + D250V + R325P | L52F + A108V + R354K and/or G284L/S + H287D + E289A |
| DS289 | M63Q + L131P + C173G + D250V + R325A + E328L | L52F + A108V + R354K and/or G284L/S + H287D + E289A |
| DS419 | M63Q + L131P + C173G + D250V + R325A + E328N | L52F + A108V + R354K and/or G284L/S + H287D + E289A |
| DS420 | M63Q + L131P + C173G + D250V + R325A | L52F + A108V + R354K and/or G284L/S + H287D + E289A |
| DS421 | M63Q + L131P + C173G + D250V + E328L | L52F + A108V + R354K and/or G284L/S + H287D + E289A |
| DS422 | M63Q + L131P + C173G + D250V + E328N | L52F + A108V + R354K and/or G284L/S + H287D + E289A |
| DS423 | M63Q + L131P + C173G + D250V | L52F + A108V + R354K and/or G284L/S + H287D + E289A |
| DS424 | M63Q + L131P + C173G + R325P + E328L | L52F + A108V + R354K and/or G284L/S + H287D + E289A |
| DS425 | M63Q + L131P + C173G + R325P + E328N | L52F + A108V + R354K and/or G284L/S + H287D + E289A |
| DS426 | M63Q + L131P + C173G + R325P | L52F + A108V + R354K and/or G284L/S + H287D + E289A |
| DS427 | M63Q + L131P + C173G + R325A + E328L | L52F + A108V + R354K and/or G284L/S + H287D + E289A |
| DS428 | M63Q + L131P + C173G + R325A + E328N | L52F + A108V + R354K and/or G284L/S + H287D + E289A |
| DS429 | M63Q + L131P + C173G + R325A | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS430 | M63Q + L131P + C173G + E328L | L52F + A108V + R354K and/or G284L/S + H287D + E289A |
| DS431 | M63Q + L131P + C173G + E328N | L52F + A108V + R354K and/or G284L/S + H287D + E289A |
| DS432 | M63Q + L131P + C173G | L52F + A108V + R354K and/or G284L/S + H287D + E289A |
| DS487 | M63Q + C173R + R207L + D250V + R325P + E328L | L52F + A108V + R354K and/or G284L/S + H287D + E289A |
| DS488 | M63Q + C173R + R207L + D250V + R325P + E328N | L52F + A108V + R354K and/or G284L/S + H287D + E289A |
| DS489 | M63Q + C173R + R207L + D250V + R325P | L52F + A108V + R354K and/or G284L/S + H287D + E289A |
| DS490 | M63Q + C173R + R207L + D250V + R325A + E328L | L52F + A108V + R354K and/or G284L/S + H287D + E289A |
| DS491 | M63Q + C173R + R207L + D250V + R325A + E328N | L52F + A108V + R354K and/or G284L/S + H287D + E289A |
| DS492 | M63Q + C173R + R207L + D250V + R325A | L52F + A108V + R354K and/or G284L/S + H287D + E289A |
| DS493 | M63Q + C173R + R207L + D250V + E328L | L52F + A108V + R354K and/or G284L/S + H287D + E289A |
| DS494 | M63Q + C173R + R207L + D250V + E328N | L52F + A108V + R354K and/or G284L/S + H287D + E289A |
| DS495 | M63Q + C173R + R207L + D250V | L52F + A108V + R354K and/or G284L/S + H287D + E289A |
| DS496 | M63Q + C173R + R207L + R325P + E328L | L52F + A108V + R354K and/or G284L/S + H287D + E289A |
| DS497 | M63Q + C173R + R207L + R325P + E328N | L52F + A108V + R354K and/or G284L/S + H287D + E289A |
| DS498 | M63Q + C173R + R207L + R325P | L52F + A108V + R354K and/or G284L/S + H287D + E289A |
| DS499 | M63Q + C173R + R207L + R325A + E328L | L52F + A108V + R354K and/or G284L/S + H287D + E289A |
| DS500 | M63Q + C173R + R207L + R325A + E328N | L52F + A108V + R354K and/or G284L/S + H287D + E289A |
| DS501 | M63Q + C173R + R207L + R325A | L52F + A108V + R354K and/or G284L/S + H287D + E289A |
| DS502 | M63Q + C173R + R207L + E328L | L52F + A108V + R354K and/or G284L/S + H287D + E289A |
| DS503 | M63Q + C173R + R207L + E328N | L52F + A108V + R354K and/or G284L/S + H287D + E289A |
| DS504 | M63Q + C173R + R207L | L52F + A108V + R354K and/or G284L/S + H287D + E289A |
| DS505 | M63Q + C173R + R207N + D250V + R325P + E328L | L52F + A108V + R354K and/or G284L/S + H287D + E289A |
| DS506 | M63Q + C173R + R207N + D250V + R325P + E328N | L52F + A108V + R354K and/or G284L/S + H287D + E289A |
| DS507 | M63Q + C173R + R207N + D250V + R325P | L52F + A108V + R354K and/or G284L/S + H287D + E289A |
| DS508 | M63Q + C173R + R207N + D250V + R325A + E328L | L52F + A108V + R354K and/or G284L/S + H287D + E289A |
| DS509 | M63Q + C173R + R207N + D250V + R325A + E328N | L52F + A108V + R354K and/or G284L/S + H287D + E289A |
| DS510 | M63Q + C173R + R207N + D250V + R325A | L52F + A108V + R354K and/or G284L/S + H287D + E289A |
| DS511 | M63Q + C173R + R207N + D250V + E328L | L52F + A108V + R354K and/or G284L/S + H287D + E289A |
| DS512 | M63Q + C173R + R207N + D250V + E328N | L52F + A108V + R354K and/or G284L/S + H287D + E289A |
| DS513 | M63Q + C173R + R207N + D250V | L52F + A108V + R354K and/or G284L/S + H287D + E289A |
| DS514 | M63Q + C173R + R207N + R325P + E328L | L52F + A108V + R354K and/or G284L/S + H287D + E289A |
| DS515 | M63Q + C173R + R207N + R325P + E328N | L52F + A108V + R354K and/or G284L/S + H287D + E289A |
| DS516 | M63Q + C173R + R207N + R325P | L52F + A108V + R354K and/or G284L/S + H287D + E289A |
| DS517 | M63Q + C173R + R207N + R325A + E328L | L52F + A108V + R354K and/or G284L/S + H287D + E289A |
| DS518 | M63Q + C173R + R207N + R325A + E328N | L52F + A108V + R354K and/or G284L/S + H287D + E289A |
| DS519 | M63Q + C173R + R207N + R325A | L52F + A108V + R354K and/or G284L/S + H287D + E289A |
| DS520 | M63Q + C173R + R207N + E328L | L52F + A108V + R354K and/or G284L/S + H287D + E289A |
| DS521 | M63Q + C173R + R207N + E328N | L52F + A108V + R354K and/or G284L/S + H287D + E289A |
| DS522 | M63Q + C173R + R207N | L52F + A108V + R354K and/or G284L/S + H287D + E289A |
| DS523 | M63Q + C173R + D250V + R325P + E328L | L52F + A108V + R354K and/or G284L/S + H287D + E289A |
| DS524 | M63Q + C173R + D250V + R325P + E328N | L52F + A108V + R354K and/or G284L/S + H287D + E289A |
| DS525 | M63Q + C173R + D250V + R325P | L52F + A108V + R354K and/or G284L/S + H287D + E289A |
| DS526 | M63Q + C173R + D250V + R325A + E328L | L52F + A108V + R354K and/or G284L/S + H287D + E289A |
| DS527 | M63Q + C173R + D250V + R325A + E328N | L52F + A108V + R354K and/or G284L/S + H287D + E289A |
| DS528 | M63Q + C173R + D250V + R325A | L52F + A108V + R354K and/or G284L/S + H287D + E289A |
| DS529 | M63Q + C173R + D250V + E328L | L52F + A108V + R354K and/or G284L/S + H287D + E289A |
| DS530 | M63Q + C173R + D250V + E328N | L52F + A108V + R354K and/or G284L/S + H287D + E289A |
| DS531 | M63Q + C173R + D250V | L52F + A108V + R354K and/or G284L/S + H287D + E289A |
| DS532 | M63Q + C173R + R325P + E328L | L52F + A108V + R354K and/or G284L/S + H287D + E289A |
| DS533 | M63Q + C173R + R325P + E328N | L52F + A108V + R354K and/or G284L/S + H287D + E289A |
| DS534 | M63Q + C173R + R325P | L52F + A108V + R354K and/or G284L/S + H287D + E289A |
| DS535 | M63Q + C173R + R325A + E328L | L52F + A108V + R354K and/or G284L/S + H287D + E289A |
| DS536 | M63Q + C173R + R325A + E328N | L52F + A108V + R354K and/or G284L/S + H287D + E289A |
| DS537 | M63Q + C173R + R325A | L52F + A108V + R354K and/or G284L/S + H287D + E289A |
| DS538 | M63Q + C173R + E328L | L52F + A108V + R354K and/or G284L/S + H287D + E289A |
| DS539 | M63Q + C173R + E328N | L52F + A108V + R354K and/or G284L/S + H287D + E289A |
| DS540 | M63Q + C173R | L52F + A108V + R354K and/or G284L/S + H287D + E289A |
| DS541 | M63Q + C173G + R207L + D250V + R325P + E328L | L52F + A108V + R354K and/or G284L/S + H287D + E289A |
| DS542 | M63Q + C173G + R207L + D250V + R325P + E328N | L52F + A108V + R354K and/or G284L/S + H287D + E289A |
| DS543 | M63Q + C173G + R207L + D250V + R325P | L52F + A108V + R354K and/or G284L/S + H287D + E289A |
| DS544 | M63Q + C173G + R207L + D250V + R325A + E328L | L52F + A108V + R354K and/or G284L/S + H287D + E289A |
| DS545 | M63Q + C173G + R207L + D250V + R325A + E328N | L52F + A108V + R354K and/or G284L/S + H287D + E289A |
| DS546 | M63Q + C173G + R207L + D250V + R325A | L52F + A108V + R354K and/or G284L/S + H287D + E289A |
| DS547 | M63Q + C173G + R207L + D250V + E328L | L52F + A108V + R354K and/or G284L/S + H287D + E289A |
| DS548 | M63Q + C173G + R207L + D250V + E328N | L52F + A108V + R354K and/or G284L/S + H287D + E289A |
| DS549 | M63Q + C173G + R207L + D250V | L52F + A108V + R354K and/or G284L/S + H287D + E289A |
| DS550 | M63Q + C173G + R207L + R325P + E328L | L52F + A108V + R354K and/or G284L/S + H287D + E289A |
| DS551 | M63Q + C173G + R207L + R325P + E328N | L52F + A108V + R354K and/or G284L/S + H287D + E289A |
| DS552 | M63Q + C173G + R207L + R325P | L52F + A108V + R354K and/or G284L/S + H287D + E289A |
| DS553 | M63Q + C173G + R207L + R325A + E328L | L52F + A108V + R354K and/or G284L/S + H287D + E289A |
| DS554 | M63Q + C173G + R207L + R325A + E328N | L52F + A108V + R354K and/or G284L/S + H287D + E289A |
| DS555 | M63Q + C173G + R207L + R325A | L52F + A108V + R354K and/or G284L/S + H287D + E289A |
| DS556 | M63Q + C173G + R207L + E328L | L52F + A108V + R354K and/or G284L/S + H287D + E289A |
| DS557 | M63Q + C173G + R207L + E328N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS558 | M63Q + C173G + R207L | L52F + A108V + R354K and/or G284L/S + H287D + E289A |
| DS559 | M63Q + C173G + R207N + D250V + R325P + E328L | L52F + A108V + R354K and/or G284L/S + H287D + E289A |
| DS560 | M63Q + C173G + R207N + D250V + R325P + E328N | L52F + A108V + R354K and/or G284L/S + H287D + E289A |
| DS561 | M63Q + C173G + R207N + D250V + R325P | L52F + A108V + R354K and/or G284L/S + H287D + E289A |
| DS562 | M63Q + C173G + R207N + D250V + R325A + E328L | L52F + A108V + R354K and/or G284L/S + H287D + E289A |
| DS563 | M63Q + C173G + R207N + D250V + R325A + E328N | L52F + A108V + R354K and/or G284L/S + H287D + E289A |
| DS564 | M63Q + C173G + R207N + D250V + R325A | L52F + A108V + R354K and/or G284L/S + H287D + E289A |
| DS565 | M63Q + C173G + R207N + D250V + E328L | L52F + A108V + R354K and/or G284L/S + H287D + E289A |
| DS566 | M63Q + C173G + R207N + D250V + E328N | L52F + A108V + R354K and/or G284L/S + H287D + E289A |
| DS567 | M63Q + C173G + R207N + D250V | L52F + A108V + R354K and/or G284L/S + H287D + E289A |
| DS568 | M63Q + C173G + R207N + R325P + E328L | L52F + A108V + R354K and/or G284L/S + H287D + E289A |
| DS569 | M63Q + C173G + R207N + R325P + E328N | L52F + A108V + R354K and/or G284L/S + H287D + E289A |
| DS570 | M63Q + C173G + R207N + R325P | L52F + A108V + R354K and/or G284L/S + H287D + E289A |
| DS571 | M63Q + C173G + R207N + R325A + E328L | L52F + A108V + R354K and/or G284L/S + H287D + E289A |
| DS572 | M63Q + C173G + R207N + R325A + E328N | L52F + A108V + R354K and/or G284L/S + H287D + E289A |
| DS573 | M63Q + C173G + R207N + R325A | L52F + A108V + R354K and/or G284L/S + H287D + E289A |
| DS574 | M63Q + C173G + R207N + E328L | L52F + A108V + R354K and/or G284L/S + H287D + E289A |
| DS575 | M63Q + C173G + R207N + E328N | L52F + A108V + R354K and/or G284L/S + H287D + E289A |
| DS576 | M63Q + C173G + R207N | L52F + A108V + R354K and/or G284L/S + H287D + E289A |
| DS577 | M63Q + C173G + D250V + R325P + E328L | L52F + A108V + R354K and/or G284L/S + H287D + E289A |
| DS578 | M63Q + C173G + D250V + R325P + E328N | L52F + A108V + R354K and/or G284L/S + H287D + E289A |
| DS579 | M63Q + C173G + D250V + R325P | L52F + A108V + R354K and/or G284L/S + H287D + E289A |
| DS580 | M63Q + C173G + D250V + R325A + E328L | L52F + A108V + R354K and/or G284L/S + H287D + E289A |
| DS581 | M63Q + C173G + D250V + R325A + E328N | L52F + A108V + R354K and/or G284L/S + H287D + E289A |
| DS582 | M63Q + C173G + D250V + R325A | L52F + A108V + R354K and/or G284L/S + H287D + E289A |
| DS583 | M63Q + C173G + D250V + E328L | L52F + A108V + R354K and/or G284L/S + H287D + E289A |
| DS584 | M63Q + C173G + D250V + E328N | L52F + A108V + R354K and/or G284L/S + H287D + E289A |
| DS585 | M63Q + C173G + D250V | L52F + A108V + R354K and/or G284L/S + H287D + E289A |
| DS586 | M63Q + C173G + R325P + E328L | L52F + A108V + R354K and/or G284L/S + H287D + E289A |
| DS587 | M63Q + C173G + R325P + E328N | L52F + A108V + R354K and/or G284L/S + H287D + E289A |
| DS588 | M63Q + C173G + R325P | L52F + A108V + R354K and/or G284L/S + H287D + E289A |
| DS589 | M63Q + C173G + R325A + E328L | L52F + A108V + R354K and/or G284L/S + H287D + E289A |
| DS590 | M63Q + C173G + R325A + E328N | L52F + A108V + R354K and/or G284L/S + H287D + E289A |
| DS591 | M63Q + C173G + R325A | L52F + A108V + R354K and/or G284L/S + H287D + E289A |
| DS592 | M63Q + C173G + E328L | L52F + A108V + R354K and/or G284L/S + H287D + E289A |
| DS593 | M63Q + C173G + E328N | L52F + A108V + R354K and/or G284L/S + H287D + E289A |
| DS594 | M63Q + C173G | L52F + A108V + R354K and/or G284L/S + H287D + E289A |
| DS649 | L131P + C173R + R207L + D250V + R325P + E328L | L52F + A108V + R354K and/or G284L/S + H287D + E289A |
| DS650 | L131P + C173R + R207L + D250V + R325P + E328N | L52F + A108V + R354K and/or G284L/S + H287D + E289A |
| DS651 | L131P + C173R + R207L + D250V + R325P | L52F + A108V + R354K and/or G284L/S + H287D + E289A |
| DS652 | L131P + C173R + R207L + D250V + R325A + E328L | L52F + A108V + R354K and/or G284L/S + H287D + E289A |
| DS653 | L131P + C173R + R207L + D250V + R325A + E328N | L52F + A108V + R354K and/or G284L/S + H287D + E289A |
| DS654 | L131P + C173R + R207L + D250V + R325A | L52F + A108V + R354K and/or G284L/S + H287D + E289A |
| DS655 | L131P + C173R + R207L + D250V + E328L | L52F + A108V + R354K and/or G284L/S + H287D + E289A |
| DS656 | L131P + C173R + R207L + D250V + E328N | L52F + A108V + R354K and/or G284L/S + H287D + E289A |
| DS657 | L131P + C173R + R207L + D250V | L52F + A108V + R354K and/or G284L/S + H287D + E289A |
| DS658 | L131P + C173R + R207L + R325P + E328L | L52F + A108V + R354K and/or G284L/S + H287D + E289A |
| DS659 | L131P + C173R + R207L + R325P + E328N | L52F + A108V + R354K and/or G284L/S + H287D + E289A |
| DS660 | L131P + C173R + R207L + R325P | L52F + A108V + R354K and/or G284L/S + H287D + E289A |
| DS661 | L131P + C173R + R207L + R325A + E328L | L52F + A108V + R354K and/or G284L/S + H287D + E289A |
| DS662 | L131P + C173R + R207L + R325A + E328N | L52F + A108V + R354K and/or G284L/S + H287D + E289A |
| DS663 | L131P + C173R + R207L + R325A | L52F + A108V + R354K and/or G284L/S + H287D + E289A |
| DS664 | L131P + C173R + R207L + E328L | L52F + A108V + R354K and/or G284L/S + H287D + E289A |
| DS665 | L131P + C173R + R207L + E328N | L52F + A108V + R354K and/or G284L/S + H287D + E289A |
| DS666 | L131P + C173R + R207L | L52F + A108V + R354K and/or G284L/S + H287D + E289A |
| DS667 | L131P + C173R + R207N + D250V + R325P + E328L | L52F + A108V + R354K and/or G284L/S + H287D + E289A |
| DS668 | L131P + C173R + R207N + D250V + R325P + E328N | L52F + A108V + R354K and/or G284L/S + H287D + E289A |
| DS669 | L131P + C173R + R207N + D250V + R325P | L52F + A108V + R354K and/or G284L/S + H287D + E289A |
| DS670 | L131P + C173R + R207N + D250V + R325A + E328L | L52F + A108V + R354K and/or G284L/S + H287D + E289A |
| DS671 | L131P + C173R + R207N + D250V + R325A + E328N | L52F + A108V + R354K and/or G284L/S + H287D + E289A |
| DS672 | L131P + C173R + R207N + D250V + R325A | L52F + A108V + R354K and/or G284L/S + H287D + E289A |
| DS673 | L131P + C173R + R207N + D250V + E328L | L52F + A108V + R354K and/or G284L/S + H287D + E289A |
| DS674 | L131P + C173R + R207N + D250V + E328N | L52F + A108V + R354K and/or G284L/S + H287D + E289A |
| DS675 | L131P + C173R + R207N + D250V | L52F + A108V + R354K and/or G284L/S + H287D + E289A |
| DS676 | L131P + C173R + R207N + R325P + E328L | L52F + A108V + R354K and/or G284L/S + H287D + E289A |
| DS677 | L131P + C173R + R207N + R325P + E328N | L52F + A108V + R354K and/or G284L/S + H287D + E289A |
| DS678 | L131P + C173R + R207N + R325P | L52F + A108V + R354K and/or G284L/S + H287D + E289A |
| DS679 | L131P + C173R + R207N + R325A + E328L | L52F + A108V + R354K and/or G284L/S + H287D + E289A |
| DS680 | L131P + C173R + R207N + R325A + E328N | L52F + A108V + R354K and/or G284L/S + H287D + E289A |
| DS681 | L131P + C173R + R207N + R325A | L52F + A108V + R354K and/or G284L/S + H287D + E289A |
| DS682 | L131P + C173R + R207N + E328L | L52F + A108V + R354K and/or G284L/S + H287D + E289A |
| DS683 | L131P + C173R + R207N + E328N | L52F + A108V + R354K and/or G284L/S + H287D + E289A |
| DS684 | L131P + C173R + R207N | L52F + A108V + R354K and/or G284L/S + H287D + E289A |
| DS685 | L131P + C173R + D250V + R325P + E328L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS686 | L131P + C173R + D250V + R325P + E328N | L52F + A108V + R354K and/or G284L/S + H287D + E289A |
| DS687 | L131P + C173R + D250V + R325P | L52F + A108V + R354K and/or G284L/S + H287D + E289A |
| DS688 | L131P + C173R + D250V + R325A + E328L | L52F + A108V + R354K and/or G284L/S + H287D + E289A |
| DS689 | L131P + C173R + D250V + R325A + E328N | L52F + A108V + R354K and/or G284L/S + H287D + E289A |
| DS690 | L131P + C173R + D250V + R325A | L52F + A108V + R354K and/or G284L/S + H287D + E289A |
| DS691 | L131P + C173R + D250V + E328L | L52F + A108V + R354K and/or G284L/S + H287D + E289A |
| DS692 | L131P + C173R + D250V + E328N | L52F + A108V + R354K and/or G284L/S + H287D + E289A |
| DS693 | L131P + C173R + D250V | L52F + A108V + R354K and/or G284L/S + H287D + E289A |
| DS694 | L131P + C173R + R325P + E328L | L52F + A108V + R354K and/or G284L/S + H287D + E289A |
| DS695 | L131P + C173R + R325P + E328N | L52F + A108V + R354K and/or G284L/S + H287D + E289A |
| DS696 | L131P + C173R + R325P | L52F + A108V + R354K and/or G284L/S + H287D + E289A |
| DS697 | L131P + C173R + R325A + E328L | L52F + A108V + R354K and/or G284L/S + H287D + E289A |
| DS698 | L131P + C173R + R325A + E328N | L52F + A108V + R354K and/or G284L/S + H287D + E289A |
| DS699 | L131P + C173R + R325A | L52F + A108V + R354K and/or G284L/S + H287D + E289A |
| DS700 | L131P + C173R + E328L | L52F + A108V + R354K and/or G284L/S + H287D + E289A |
| DS701 | L131P + C173R + E328N | L52F + A108V + R354K and/or G284L/S + H287D + E289A |
| DS702 | L131P + C173R | L52F + A108V + R354K and/or G284L/S + H287D + E289A |
| DS703 | L131P + C173G + R207L + D250V + R325P + E328L | L52F + A108V + R354K and/or G284L/S + H287D + E289A |
| DS704 | L131P + C173G + R207L + D250V + R325P + E328N | L52F + A108V + R354K and/or G284L/S + H287D + E289A |
| DS705 | L131P + C173G + R207L + D250V + R325P | L52F + A108V + R354K and/or G284L/S + H287D + E289A |
| DS706 | L131P + C173G + R207L + D250V + R325A + E328L | L52F + A108V + R354K and/or G284L/S + H287D + E289A |
| DS707 | L131P + C173G + R207L + D250V + R325A + E328N | L52F + A108V + R354K and/or G284L/S + H287D + E289A |
| DS708 | L131P + C173G + R207L + D250V + R325A | L52F + A108V + R354K and/or G284L/S + H287D + E289A |
| DS709 | L131P + C173G + R207L + D250V + E328L | L52F + A108V + R354K and/or G284L/S + H287D + E289A |
| DS710 | L131P + C173G + R207L + D250V + E328N | L52F + A108V + R354K and/or G284L/S + H287D + E289A |
| DS711 | L131P + C173G + R207L + D250V | L52F + A108V + R354K and/or G284L/S + H287D + E289A |
| DS712 | L131P + C173G + R207L + R325P + E328L | L52F + A108V + R354K and/or G284L/S + H287D + E289A |
| DS713 | L131P + C173G + R207L + R325P + E328N | L52F + A108V + R354K and/or G284L/S + H287D + E289A |
| DS714 | L131P + C173G + R207L + R325P | L52F + A108V + R354K and/or G284L/S + H287D + E289A |
| DS715 | L131P + C173G + R207L + R325A + E328L | L52F + A108V + R354K and/or G284L/S + H287D + E289A |
| DS716 | L131P + C173G + R207L + R325A + E328N | L52F + A108V + R354K and/or G284L/S + H287D + E289A |
| DS717 | L131P + C173G + R207L + R325A | L52F + A108V + R354K and/or G284L/S + H287D + E289A |
| DS718 | L131P + C173G + R207L + E328L | L52F + A108V + R354K and/or G284L/S + H287D + E289A |
| DS719 | L131P + C173G + R207L + E328N | L52F + A108V + R354K and/or G284L/S + H287D + E289A |
| DS720 | L131P + C173G + R207L | L52F + A108V + R354K and/or G284L/S + H287D + E289A |
| DS721 | L131P + C173G + R207N + D250V + R325P + E328L | L52F + A108V + R354K and/or G284L/S + H287D + E289A |
| DS722 | L131P + C173G + R207N + D250V + R325P + E328N | L52F + A108V + R354K and/or G284L/S + H287D + E289A |
| DS723 | L131P + C173G + R207N + D250V + R325P | L52F + A108V + R354K and/or G284L/S + H287D + E289A |
| DS724 | L131P + C173G + R207N + D250V + R325A + E328L | L52F + A108V + R354K and/or G284L/S + H287D + E289A |
| DS725 | L131P + C173G + R207N + D250V + R325A + E328N | L52F + A108V + R354K and/or G284L/S + H287D + E289A |
| DS726 | L131P + C173G + R207N + D250V + R325A | L52F + A108V + R354K and/or G284L/S + H287D + E289A |
| DS727 | L131P + C173G + R207N + D250V + E328L | L52F + A108V + R354K and/or G284L/S + H287D + E289A |
| DS728 | L131P + C173G + R207N + D250V + E328N | L52F + A108V + R354K and/or G284L/S + H287D + E289A |
| DS729 | L131P + C173G + R207N + D250V | L52F + A108V + R354K and/or G284L/S + H287D + E289A |
| DS730 | L131P + C173G + R207N + R325P + E328L | L52F + A108V + R354K and/or G284L/S + H287D + E289A |
| DS731 | L131P + C173G + R207N + R325P + E328N | L52F + A108V + R354K and/or G284L/S + H287D + E289A |
| DS732 | L131P + C173G + R207N + R325P | L52F + A108V + R354K and/or G284L/S + H287D + E289A |
| DS733 | L131P + C173G + R207N + R325A + E328L | L52F + A108V + R354K and/or G284L/S + H287D + E289A |
| DS734 | L131P + C173G + R207N + R325A + E328N | L52F + A108V + R354K and/or G284L/S + H287D + E289A |
| DS735 | L131P + C173G + R207N + R325A | L52F + A108V + R354K and/or G284L/S + H287D + E289A |
| DS736 | L131P + C173G + R207N + E328L | L52F + A108V + R354K and/or G284L/S + H287D + E289A |
| DS737 | L131P + C173G + R207N + E328N | L52F + A108V + R354K and/or G284L/S + H287D + E289A |
| DS738 | L131P + C173G + R207N | L52F + A108V + R354K and/or G284L/S + H287D + E289A |
| DS739 | L131P + C173G + D250V + R325P + E328L | L52F + A108V + R354K and/or G284L/S + H287D + E289A |
| DS740 | L131P + C173G + D250V + R325P + E328N | L52F + A108V + R354K and/or G284L/S + H287D + E289A |
| DS741 | L131P + C173G + D250V + R325P | L52F + A108V + R354K and/or G284L/S + H287D + E289A |
| DS742 | L131P + C173G + D250V + R325A + E328L | L52F + A108V + R354K and/or G284L/S + H287D + E289A |
| DS743 | L131P + C173G + D250V + R325A + E328N | L52F + A108V + R354K and/or G284L/S + H287D + E289A |
| DS744 | L131P + C173G + D250V + R325A | L52F + A108V + R354K and/or G284L/S + H287D + E289A |
| DS745 | L131P + C173G + D250V + E328L | L52F + A108V + R354K and/or G284L/S + H287D + E289A |
| DS746 | L131P + C173G + D250V + E328N | L52F + A108V + R354K and/or G284L/S + H287D + E289A |
| DS747 | L131P + C173G + D250V | L52F + A108V + R354K and/or G284L/S + H287D + E289A |
| DS748 | L131P + C173G + R325P + E328L | L52F + A108V + R354K and/or G284L/S + H287D + E289A |
| DS749 | L131P + C173G + R325P + E328N | L52F + A108V + R354K and/or G284L/S + H287D + E289A |
| DS750 | L131P + C173G + R325P | L52F + A108V + R354K and/or G284L/S + H287D + E289A |
| DS751 | L131P + C173G + R325A + E328L | L52F + A108V + R354K and/or G284L/S + H287D + E289A |
| DS752 | L131P + C173G + R325A + E328N | L52F + A108V + R354K and/or G284L/S + H287D + E289A |
| DS753 | L131P + C173G + R325A | L52F + A108V + R354K and/or G284L/S + H287D + E289A |
| DS754 | L131P + C173G + E328L | L52F + A108V + R354K and/or G284L/S + H287D + E289A |
| DS755 | L131P + C173G + E328N | L52F + A108V + R354K and/or G284L/S + H287D + E289A |
| DS756 | L131P + C173G | L52F + A108V + R354K and/or G284L/S + H287D + E289A |
| DS811 | C173R + R207L + D250V + R325P + E328L | L52F + A108V + R354K and/or G284L/S + H287D + E289A |
| DS812 | C173R + R207L + D250V + R325P + E328N | L52F + A108V + R354K and/or G284L/S + H287D + E289A |
| DS813 | C173R + R207L + D250V + R325P | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS814 | C173R + R207L + D250V + R325A + E328L | L52F + A108V + R354K and/or G284L/S + H287D + E289A |
| DS815 | C173R + R207L + D250V + R325A + E328N | L52F + A108V + R354K and/or G284L/S + H287D + E289A |
| DS816 | C173R + R207L + D250V + R325A | L52F + A108V + R354K and/or G284L/S + H287D + E289A |
| DS817 | C173R + R207L + D250V + E328L | L52F + A108V + R354K and/or G284L/S + H287D + E289A |
| DS818 | C173R + R207L + D250V + E328N | L52F + A108V + R354K and/or G284L/S + H287D + E289A |
| DS819 | C173R + R207L + D250V | L52F + A108V + R354K and/or G284L/S + H287D + E289A |
| DS820 | C173R + R207L + R325P + E328L | L52F + A108V + R354K and/or G284L/S + H287D + E289A |
| DS821 | C173R + R207L + R325P + E328N | L52F + A108V + R354K and/or G284L/S + H287D + E289A |
| DS822 | C173R + R207L + R325P | L52F + A108V + R354K and/or G284L/S + H287D + E289A |
| DS823 | C173R + R207L + R325A + E328L | L52F + A108V + R354K and/or G284L/S + H287D + E289A |
| DS824 | C173R + R207L + R325A + E328N | L52F + A108V + R354K and/or G284L/S + H287D + E289A |
| DS825 | C173R + R207L + R325A | L52F + A108V + R354K and/or G284L/S + H287D + E289A |
| DS826 | C173R + R207L + E328L | L52F + A108V + R354K and/or G284L/S + H287D + E289A |
| DS827 | C173R + R207L + E328N | L52F + A108V + R354K and/or G284L/S + H287D + E289A |
| DS828 | C173R + R207L | L52F + A108V + R354K and/or G284L/S + H287D + E289A |
| DS829 | C173R + R207N + D250V + R325P + E328L | L52F + A108V + R354K and/or G284L/S + H287D + E289A |
| DS830 | C173R + R207N + D250V + R325P + E328N | L52F + A108V + R354K and/or G284L/S + H287D + E289A |
| DS831 | C173R + R207N + D250V + R325P | L52F + A108V + R354K and/or G284L/S + H287D + E289A |
| DS832 | C173R + R207N + D250V + R325A + E328L | L52F + A108V + R354K and/or G284L/S + H287D + E289A |
| DS833 | C173R + R207N + D250V + R325A + E328N | L52F + A108V + R354K and/or G284L/S + H287D + E289A |
| DS834 | C173R + R207N + D250V + R325A | L52F + A108V + R354K and/or G284L/S + H287D + E289A |
| DS835 | C173R + R207N + D250V + E328L | L52F + A108V + R354K and/or G284L/S + H287D + E289A |
| DS836 | C173R + R207N + D250V + E328N | L52F + A108V + R354K and/or G284L/S + H287D + E289A |
| DS837 | C173R + R207N + D250V | L52F + A108V + R354K and/or G284L/S + H287D + E289A |
| DS838 | C173R + R207N + R325P + E328L | L52F + A108V + R354K and/or G284L/S + H287D + E289A |
| DS839 | C173R + R207N + R325P + E328N | L52F + A108V + R354K and/or G284L/S + H287D + E289A |
| DS840 | C173R + R207N + R325P | L52F + A108V + R354K and/or G284L/S + H287D + E289A |
| DS841 | C173R + R207N + R325A + E328L | L52F + A108V + R354K and/or G284L/S + H287D + E289A |
| DS842 | C173R + R207N + R325A + E328N | L52F + A108V + R354K and/or G284L/S + H287D + E289A |
| DS843 | C173R + R207N + R325A | L52F + A108V + R354K and/or G284L/S + H287D + E289A |
| DS844 | C173R + R207N + E328L | L52F + A108V + R354K and/or G284L/S + H287D + E289A |
| DS845 | C173R + R207N + E328N | L52F + A108V + R354K and/or G284L/S + H287D + E289A |
| DS846 | C173R + R207N | L52F + A108V + R354K and/or G284L/S + H287D + E289A |
| DS847 | C173R + D250V + R325P + E328L | L52F + A108V + R354K and/or G284L/S + H287D + E289A |
| DS848 | C173R + D250V + R325P + E328N | L52F + A108V + R354K and/or G284L/S + H287D + E289A |
| DS849 | C173R + D250V + R325P | L52F + A108V + R354K and/or G284L/S + H287D + E289A |
| DS850 | C173R + D250V + R325A + E328L | L52F + A108V + R354K and/or G284L/S + H287D + E289A |
| DS851 | C173R + D250V + R325A + E328N | L52F + A108V + R354K and/or G284L/S + H287D + E289A |
| DS852 | C173R + D250V + R325A | L52F + A108V + R354K and/or G284L/S + H287D + E289A |
| DS853 | C173R + D250V + E328L | L52F + A108V + R354K and/or G284L/S + H287D + E289A |
| DS854 | C173R + D250V + E328N | L52F + A108V + R354K and/or G284L/S + H287D + E289A |
| DS855 | C173R + D250V | L52F + A108V + R354K and/or G284L/S + H287D + E289A |
| DS856 | C173R + R325P + E328L | L52F + A108V + R354K and/or G284L/S + H287D + E289A |
| DS857 | C173R + R325P + E328N | L52F + A108V + R354K and/or G284L/S + H287D + E289A |
| DS858 | C173R + R325P | L52F + A108V + R354K and/or G284L/S + H287D + E289A |
| DS859 | C173R + R325A + E328L | L52F + A108V + R354K and/or G284L/S + H287D + E289A |
| DS860 | C173R + R325A + E328N | L52F + A108V + R354K and/or G284L/S + H287D + E289A |
| DS861 | C173R + R325A | L52F + A108V + R354K and/or G284L/S + H287D + E289A |
| DS862 | C173R + E328L | L52F + A108V + R354K and/or G284L/S + H287D + E289A |
| DS863 | C173R + E328N | L52F + A108V + R354K and/or G284L/S + H287D + E289A |
| DS864 | C173R | L52F + A108V + R354K and/or G284L/S + H287D + E289A |
| DS865 | C173G + R207L + D250V + R325P + E328L | L52F + A108V + R354K and/or G284L/S + H287D + E289A |
| DS866 | C173G + R207L + D250V + R325P + E328N | L52F + A108V + R354K and/or G284L/S + H287D + E289A |
| DS867 | C173G + R207L + D250V + R325P | L52F + A108V + R354K and/or G284L/S + H287D + E289A |
| DS868 | C173G + R207L + D250V + R325A + E328L | L52F + A108V + R354K and/or G284L/S + H287D + E289A |
| DS869 | C173G + R207L + D250V + R325A + E328N | L52F + A108V + R354K and/or G284L/S + H287D + E289A |
| DS870 | C173G + R207L + D250V + R325A | L52F + A108V + R354K and/or G284L/S + H287D + E289A |
| DS871 | C173G + R207L + D250V + E328L | L52F + A108V + R354K and/or G284L/S + H287D + E289A |
| DS872 | C173G + R207L + D250V + E328N | L52F + A108V + R354K and/or G284L/S + H287D + E289A |
| DS873 | C173G + R207L + D250V | L52F + A108V + R354K and/or G284L/S + H287D + E289A |
| DS874 | C173G + R207L + R325P + E328L | L52F + A108V + R354K and/or G284L/S + H287D + E289A |
| DS875 | C173G + R207L + R325P + E328N | L52F + A108V + R354K and/or G284L/S + H287D + E289A |
| DS876 | C173G + R207L + R325P | L52F + A108V + R354K and/or G284L/S + H287D + E289A |
| DS877 | C173G + R207L + R325A + E328L | L52F + A108V + R354K and/or G284L/S + H287D + E289A |
| DS878 | C173G + R207L + R325A + E328N | L52F + A108V + R354K and/or G284L/S + H287D + E289A |
| DS879 | C173G + R207L + R325A | L52F + A108V + R354K and/or G284L/S + H287D + E289A |
| DS880 | C173G + R207L + E328L | L52F + A108V + R354K and/or G284L/S + H287D + E289A |
| DS881 | C173G + R207L + E328N | L52F + A108V + R354K and/or G284L/S + H287D + E289A |
| DS882 | C173G + R207L | L52F + A108V + R354K and/or G284L/S + H287D + E289A |
| DS883 | C173G + R207N + D250V + R325P + E328L | L52F + A108V + R354K and/or G284L/S + H287D + E289A |
| DS884 | C173G + R207N + D250V + R325P + E328N | L52F + A108V + R354K and/or G284L/S + H287D + E289A |
| DS885 | C173G + R207N + D250V + R325P | L52F + A108V + R354K and/or G284L/S + H287D + E289A |
| DS886 | C173G + R207N + D250V + R325A + E328L | L52F + A108V + R354K and/or G284L/S + H287D + E289A |
| DS887 | C173G + R207N + D250V + R325A + E328N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS888 | C173G + R207N + D250V + R325A | L52F + A108V + R354K and/or G284L/S + H287D + E289A |
| DS889 | C173G + R207N + D250V + E328L | L52F + A108V + R354K and/or G284L/S + H287D + E289A |
| DS890 | C173G + R207N + D250V + E328N | L52F + A108V + R354K and/or G284L/S + H287D + E289A |
| DS891 | C173G + R207N + D250V | L52F + A108V + R354K and/or G284L/S + H287D + E289A |
| DS892 | C173G + R207N + R325P + E328L | L52F + A108V + R354K and/or G284L/S + H287D + E289A |
| DS893 | C173G + R207N + R325P + E328N | L52F + A108V + R354K and/or G284L/S + H287D + E289A |
| DS894 | C173G + R207N + R325P | L52F + A108V + R354K and/or G284L/S + H287D + E289A |
| DS895 | C173G + R207N + R325A + E328L | L52F + A108V + R354K and/or G284L/S + H287D + E289A |
| DS896 | C173G + R207N + R325A + E328N | L52F + A108V + R354K and/or G284L/S + H287D + E289A |
| DS897 | C173G + R207N + R325A | L52F + A108V + R354K and/or G284L/S + H287D + E289A |
| DS898 | C173G + R207N + E328L | L52F + A108V + R354K and/or G284L/S + H287D + E289A |
| DS899 | C173G + R207N + E328N | L52F + A108V + R354K and/or G284L/S + H287D + E289A |
| DS900 | C173G + R207N | L52F + A108V + R354K and/or G284L/S + H287D + E289A |
| DS901 | C173G + D250V + R325P + E328L | L52F + A108V + R354K and/or G284L/S + H287D + E289A |
| DS902 | C173G + D250V + R325P + E328N | L52F + A108V + R354K and/or G284L/S + H287D + E289A |
| DS903 | C173G + D250V + R325P | L52F + A108V + R354K and/or G284L/S + H287D + E289A |
| DS904 | C173G + D250V + R325A + E328L | L52F + A108V + R354K and/or G284L/S + H287D + E289A |
| DS905 | C173G + D250V + R325A + E328N | L52F + A108V + R354K and/or G284L/S + H287D + E289A |
| DS906 | C173G + D250V + R325A | L52F + A108V + R354K and/or G284L/S + H287D + E289A |
| DS907 | C173G + D250V + E328L | L52F + A108V + R354K and/or G284L/S + H287D + E289A |
| DS908 | C173G + D250V + E328N | L52F + A108V + R354K and/or G284L/S + H287D + E289A |
| DS909 | C173G + D250V | L52F + A108V + R354K and/or G284L/S + H287D + E289A |
| DS910 | C173G + R325P + E328L | L52F + A108V + R354K and/or G284L/S + H287D + E289A |
| DS911 | C173G + R325P + E328N | L52F + A108V + R354K and/or G284L/S + H287D + E289A |
| DS912 | C173G + R325P | L52F + A108V + R354K and/or G284L/S + H287D + E289A |
| DS913 | C173G + R325A + E328L | L52F + A108V + R354K and/or G284L/S + H287D + E289A |
| DS914 | C173G + R325A + E328N | L52F + A108V + R354K and/or G284L/S + H287D + E289A |
| DS915 | C173G + R325A | L52F + A108V + R354K and/or G284L/S + H287D + E289A |
| DS916 | C173G + E328L | L52F + A108V + R354K and/or G284L/S + H287D + E289A |
| DS917 | C173G + E328N | L52F + A108V + R354K and/or G284L/S + H287D + E289A |
| DS918 | C173G | L52F + A108V + R354K and/or G284L/S + H287D + E289A |

In a particular embodiment, the variants of the invention comprise the amino acid sequence of SEQ ID NO:2 (or functionally equivalent sequence) and optionally additional amino acid fragments at the C-ter or N-ter. In another embodiment, the variants of the invention consist solely on the amino acid sequence of SEQ ID NO:2 (or functionally equivalent sequence). More particularly, in a particular embodiment, the variants of the invention are deprived of the BRTC-like domain, which corresponds to residues 1 to 129 of SEQ ID NO:1.

According to a second aspect of the invention, the variant of Terminal deoxynucleotidyl Transferase (TdT) (i) comprises an amino acid sequence as set forth in SEQ ID NO:2 or a functionally equivalent sequence (such as, SEQ ID NOs:11, 13, 15, 17, 19, 21, 23, 25, 27, 29, 31, 33 or 35) or an amino acid sequence having a specified percent sequence identity of any of the foregoing sequences, with at least three amino acid substitutions selected from M63R/Q, L131P, C173G/R, R207L/N, D250V, R325P/N and E328N/L/T/S, or a functionally equivalent residue, wherein the positions are numbered by reference to the amino acid sequence set forth in SEQ ID NO:1 or as set forth directly elsewhere herein in respect of their individual SEQ ID NOs, (ii) is able to synthesize a nucleic acid fragment without template and (iii) is able to incorporate a modified nucleotide, such as a 3'-O-modified nucleotide, into the nucleic fragment.

For instance, the variant of TdT comprises an amino acid sequence within a specified percent sequence identity of SEQ ID NO:2 and a combination of substitutions selected from M63R+L131P+R207L, M63R+L131P+R207N, M63R+L131P+D250V, M63R+L131P+R325P, M63R+L131P+R325A, M63R+L131P+E328L, M63R+L131P+E328N, M63R+R207L+D250V, M63R+R207L+R325P, M63R+R207L+R325A, M63R+R207L+E328L, M63R+R207L+E328N, M63R+R207N+D250V, M63R+R207N+R325P, M63R+R207N+R325A, M63R+R207N+E328L, M63R+R207N+E328N, M63R+D250V+R325P, M63R+D250V+R325A, M63R+R325P+E328L, M63R+R325P+E328N, M63R+R325A+E328L, M63R+R325A+E328N, M63Q+L131P+R207L, M63Q+L131P+R207N, M63Q+L131P+D250V, M63Q+L131P+R325P, M63Q+L131P+R325A, M63Q+L131P+E328L, M63Q+L131P+E328N, M63Q+R207L+D250V, M63Q+R207L+R325P, M63Q+R207L+R325A, M63Q+R207L+E328L, M63Q+R207L+E328N, M63Q+D250V+R325P, M63Q+D250V+R325A, M63Q+D250V+E328L, M63Q+D250V+E328N, M63Q+R325P+E328L, M63Q+R325P+E328N, M63Q+R325A+E328L, M63Q+R325A+E328N, L131P+R207L+D250V, L131P+R207L+R325A, L131P+R207L+E328L, L131P+R207L+E328N, L131P+R207N+D250V, L131P+R207N+R325P, L131P+R207N+R325A, L131P+R207N+E328L, L131P+R207N+E328N, L131P+D250V+R325P, L131P+D250V+R325A, L131P+D250V+E328L, L131P+D250V+E328N, L131P+R325P+E328L, L131P+R325P+E328N, L131P+R325A+E328L, L131P+R325A+E328N, R207L+D250V+R325P, R207L+D250V+R325A, R207L+D250V+E328L, R207L+D250V+E328N, R207L+R325P+E328L, R207L+R325P+E328N, R207L+R325A+E328L, R207L+R325A+E328N, R207N+D250V+R325P, R207N+D250V+R325A, R207N+D250V+E328L, R207N+D250V+E328N, R207N+R325P+E328L, R207N+R325P+E328N, R207N+R325A+E328L, R207N+R325A+E328N, D250V+R325P+E328L, D250V+R325P+E328N, D250V+R325A+E328L, D250V+R325A+E328N and R207L+D250V+R325P, or functionally equivalent residue(s) wherein the above position numbers are with respect to SEQ ID NO:2.

In a particular embodiment, the variant of TdT comprises an amino acid sequence within a specified percent sequence identity of SEQ ID NO:2, or functionally equivalent sequence, with the combination of substitutions R207L+R325P+E328L (DS928), or functionally equivalent residues.

In a particular embodiment, the variant of TdT comprises an amino acid sequence within a specified percent sequence identity of SEQ ID NO:2, or functionally equivalent sequence, with the combination of substitutions R207N+R325A+E328N (DS950), or functionally equivalent residues.

Such variant may further comprise at least one substitution at position corresponding to residues selected from L52, A108, L131, T340, G284, H287, E289, W450, R354 and A510, or functionally equivalent residue(s).

As exposed above, said variant may also comprise the combination of constant mutations L52F+A108V+R354K and/or G284L/S+H287D+E289A, or functionally equivalent residue(s).

According to a further aspect, the invention provides a variant of Terminal deoxynucleotidyl Transferase (TdT) which (i) comprises an amino acid sequence within a specified percent sequence identity of SEQ ID NO:2 or a functionally equivalent sequence, with at least one amino acid substitution selected from M63R, M63Q, L131P, R207L, R207N, D250V, R325P, R325A, E328L, E328N, or functionally equivalent residue(s), (ii) is able to synthesize a nucleic acid fragment without a template and (iii) is able to incorporate a 3'-O-modified nucleotide into the nucleic fragment.

In another aspect, the invention provides a variant of Terminal deoxynucleotidyl Transferase (TdT) which (i) comprises an amino acid sequence within a specified percent sequence identity of SEQ ID NO:2 or a functionally equivalent sequence, with at least the combination of substitutions selected from M63R+L131P, M63R+R207L, M63R+R207N, M63R+D250V, M63R+R325P, M63R+R325A, M63R+E328L, M63R+E328N, M63Q+L131P, M63Q+R207L, M63Q+R207N, M63Q+D250V, M63Q+R325P, M63Q+R325A, M63Q+E328L, M63Q+E328N, L131P+R207L, L131P+R207N, L131P+D250V, L131P+R325P, L131P+R325A, L131P+E328L, L131P+E328N, R207L+D250V, R207L+R325P, R207L+R325A, R207L+E328L, R207L+E328N, R207N+D250V, R207N+R325P, R207N+R325A, R207N+E328L, R207N+E328N, D250V+R325P, D250V+R325A, D250V+E328L, D250V+E328N, R325P+E328L, R325P+E328N, R325A+E328L and R325A+E328N, or functionally equivalent residue(s), wherein the positions are numbered by reference to the amino acid sequence set forth in SEQ ID NO:2, (ii) is able to synthesize a nucleic acid fragment without a template and (iii) is able to incorporate a 3'-O-modified nucleotide into the nucleic fragment.

It is thus an object of the invention to provide a TdT variant having an amino acid sequence within a specified percent sequence identity of SEQ ID NO:2, or functionally equivalent sequence, with any substitution or combination of substitutions listed in Table 6, listed as "Variable Mutations", or functionally equivalent residue(s) and optionally one or both combinations of constant mutations L52F+A108V+R354K an G284L/S+H287D+E289A, or functionally equivalent residue(s).

According to a particular embodiment, the variant comprises at least one substitution or combination of substitutions as listed in Table 6, and optionally one or more additional mutation(s).

TABLE 2

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
| --- | --- | --- |
| DS109 | M63R + L131P + R207L + D250V + R325P + E328L | L52F + A108V + R354K and/or G284L/S + H287D + E289A |
| DS110 | M63R + L131P + R207L + D250V + R325P + E328N | L52F + A108V + R354K and/or G284L/S + H287D + E289A |
| DS111 | M63R + L131P + R207L + D250V + R325P | L52F + A108V + R354K and/or G284L/S + H287D + E289A |
| DS112 | M63R + L131P + R207L + D250V + R325A + E328L | L52F + A108V + R354K and/or G284L/S + H287D + E289A |
| DS113 | M63R + L131P + R207L + D250V + R325A + E328N | L52F + A108V + R354K and/or G284L/S + H287D + E289A |
| DS114 | M63R + L131P + R207L + D250V + R325A | L52F + A108V + R354K and/or G284L/S + H287D + E289A |
| DS115 | M63R + L131P + R207L + D250V + E328L | L52F + A108V + R354K and/or G284L/S + H287D + E289A |
| DS116 | M63R + L131P + R207L + D250V + E328N | L52F + A108V + R354K and/or G284L/S + H287D + E289A |
| DS117 | M63R + L131P + R207L + D250V | L52F + A108V + R354K and/or G284L/S + H287D + E289A |
| DS118 | M63R + L131P + R207L + R325P + E328L | L52F + A108V + R354K and/or G284L/S + H287D + E289A |
| DS119 | M63R + L131P + R207L + R325P + E328N | L52F + A108V + R354K and/or G284L/S + H287D + E289A |
| DS120 | M63R + L131P + R207L + R325P | L52F + A108V + R354K and/or G284L/S + H287D + E289A |
| DS121 | M63R + L131P + R207L + R325A + E328L | L52F + A108V + R354K and/or G284L/S + H287D + E289A |
| DS122 | M63R + L131P + R207L + R325A + E328N | L52F + A108V + R354K and/or G284L/S + H287D + E289A |
| DS123 | M63R + L131P + R207L + R325A | L52F + A108V + R354K and/or G284L/S + H287D + E289A |
| DS124 | M63R + L131P + R207L + E328L | L52F + A108V + R354K and/or G284L/S + H287D + E289A |
| DS125 | M63R + L131P + R207L + E328N | L52F + A108V + R354K and/or G284L/S + H287D + E289A |
| DS126 | M63R + L131P + R207L | L52F + A108V + R354K and/or G284L/S + H287D + E289A |
| DS127 | M63R + L131P + R207N + D250V + R325P + E328L | L52F + A108V + R354K and/or G284L/S + H287D + E289A |
| DS128 | M63R + L131P + R207N + D250V + R325P + E328N | L52F + A108V + R354K and/or G284L/S + H287D + E289A |
| DS129 | M63R + L131P + R207N + D250V + R325P | L52F + A108V + R354K and/or G284L/S + H287D + E289A |
| DS130 | M63R + L131P + R207N + D250V + R325A + E328L | L52F + A108V + R354K and/or G284L/S + H287D + E289A |
| DS131 | M63R + L131P + R207N + D250V + R325A + E328N | L52F + A108V + R354K and/or G284L/S + H287D + E289A |
| DS132 | M63R + L131P + R207N + D250V + R325A | L52F + A108V + R354K and/or G284L/S + H287D + E289A |
| DS133 | M63R + L131P + R207N + D250V + E328L | L52F + A108V + R354K and/or G284L/S + H287D + E289A |
| DS134 | M63R + L131P + R207N + D250V + E328N | L52F + A108V + R354K and/or G284L/S + H287D + E289A |
| DS135 | M63R + L131P + R207N + D250V | L52F + A108V + R354K and/or G284L/S + H287D + E289A |
| DS136 | M63R + L131P + R207N + R325P + E328L | L52F + A108V + R354K and/or G284L/S + H287D + E289A |
| DS137 | M63R + L131P + R207N + R325P + E328N | L52F + A108V + R354K and/or G284L/S + H287D + E289A |
| DS138 | M63R + L131P + R207N + R325P | L52F + A108V + R354K and/or G284L/S + H287D + E289A |
| DS139 | M63R + L131P + R207N + R325A + E328L | L52F + A108V + R354K and/or G284L/S + H287D + E289A |

TABLE 2-continued

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
| --- | --- | --- |
| DS140 | M63R + L131P + R207N + R325A + E328N | L52F + A108V + R354K and/or G284L/S + H287D + E289A |
| DS141 | M63R + L131P + R207N + R325A | L52F + A108V + R354K and/or G284L/S + H287D + E289A |
| DS142 | M63R + L131P + R207N + E328L | L52F + A108V + R354K and/or G284L/S + H287D + E289A |
| DS143 | M63R + L131P + R207N + E328N | L52F + A108V + R354K and/or G284L/S + H287D + E289A |
| DS144 | M63R + L131P + R207N | L52F + A108V + R354K and/or G284L/S + H287D + E289A |
| DS145 | M63R + L131P + D250V + R325P + E328L | L52F + A108V + R354K and/or G284L/S + H287D + E289A |
| DS146 | M63R + L131P + D250V + R325P + E328N | L52F + A108V + R354K and/or G284L/S + H287D + E289A |
| DS147 | M63R + L131P + D250V + R325P | L52F + A108V + R354K and/or G284L/S + H287D + E289A |
| DS148 | M63R + L131P + D250V + R325A + E328L | L52F + A108V + R354K and/or G284L/S + H287D + E289A |
| DS149 | M63R + L131P + D250V + R325A + E328N | L52F + A108V + R354K and/or G284L/S + H287D + E289A |
| DS150 | M63R + L131P + D250V + R325A | L52F + A108V + R354K and/or G284L/S + H287D + E289A |
| DS151 | M63R + L131P + D250V + E328L | L52F + A108V + R354K and/or G284L/S + H287D + E289A |
| DS152 | M63R + L131P + D250V + E328N | L52F + A108V + R354K and/or G284L/S + H287D + E289A |
| DS153 | M63R + L131P + D250V | L52F + A108V + R354K and/or G284L/S + H287D + E289A |
| DS154 | M63R + L131P + R325P + E328L | L52F + A108V + R354K and/or G284L/S + H287D + E289A |
| DS155 | M63R + L131P + R325P + E328N | L52F + A108V + R354K and/or G284L/S + H287D + E289A |
| DS156 | M63R + L131P + R325P | L52F + A108V + R354K and/or G284L/S + H287D + E289A |
| DS157 | M63R + L131P + R325A + E328L | L52F + A108V + R354K and/or G284L/S + H287D + E289A |
| DS158 | M63R + L131P + R325A + E328N | L52F + A108V + R354K and/or G284L/S + H287D + E289A |
| DS159 | M63R + L131P + R325A | L52F + A108V + R354K and/or G284L/S + H287D + E289A |
| DS160 | M63R + L131P + E328L | L52F + A108V + R354K and/or G284L/S + H287D + E289A |
| DS161 | M63R + L131P + E328N | L52F + A108V + R354K and/or G284L/S + H287D + E289A |
| DS162 | M63R + L131P | L52F + A108V + R354K and/or G284L/S + H287D + E289A |
| DS271 | M63R + R207L + D250V + R325P + E328L | L52F + A108V + R354K and/or G284L/S + H287D + E289A |
| DS272 | M63R + R207L + D250V + R325P + E328N | L52F + A108V + R354K and/or G284L/S + H287D + E289A |
| DS273 | M63R + R207L + D250V + R325P | L52F + A108V + R354K and/or G284L/S + H287D + E289A |
| DS274 | M63R + R207L + D250V + R325A + E328L | L52F + A108V + R354K and/or G284L/S + H287D + E289A |
| DS275 | M63R + R207L + D250V + R325A + E328N | L52F + A108V + R354K and/or G284L/S + H287D + E289A |
| DS276 | M63R + R207L + D250V + R325A | L52F + A108V + R354K and/or G284L/S + H287D + E289A |
| DS277 | M63R + R207L + D250V + E328L | L52F + A108V + R354K and/or G284L/S + H287D + E289A |
| DS278 | M63R + R207L + D250V + E328N | L52F + A108V + R354K and/or G284L/S + H287D + E289A |
| DS279 | M63R + R207L + D250V | L52F + A108V + R354K and/or G284L/S + H287D + E289A |
| DS280 | M63R + R207L + R325P + E328L | L52F + A108V + R354K and/or G284L/S + H287D + E289A |
| DS281 | M63R + R207L + R325P + E328N | L52F + A108V + R354K and/or G284L/S + H287D + E289A |
| DS282 | M63R + R207L + R325P | L52F + A108V + R354K and/or G284L/S + H287D + E289A |
| DS283 | M63R + R207L + R325A + E328L | L52F + A108V + R354K and/or G284L/S + H287D + E289A |
| DS284 | M63R + R207L + R325A + E328N | L52F + A108V + R354K and/or G284L/S + H287D + E289A |
| DS285 | M63R + R207L + R325A | L52F + A108V + R354K and/or G284L/S + H287D + E289A |
| DS286 | M63R + R207L + E328L | L52F + A108V + R354K and/or G284L/S + H287D + E289A |
| DS287 | M63R + R207L + E328N | L52F + A108V + R354K and/or G284L/S + H287D + E289A |
| DS288 | M63R + R207L | L52F + A108V + R354K and/or G284L/S + H287D + E289A |
| DS289 | M63R + R207N + D250V + R325P + E328L | L52F + A108V + R354K and/or G284L/S + H287D + E289A |
| DS290 | M63R + R207N + D250V + R325P + E328N | L52F + A108V + R354K and/or G284L/S + H287D + E289A |
| DS291 | M63R + R207N + D250V + R325P | L52F + A108V + R354K and/or G284L/S + H287D + E289A |
| DS292 | M63R + R207N + D250V + R325A + E328L | L52F + A108V + R354K and/or G284L/S + H287D + E289A |
| DS293 | M63R + R207N + D250V + R325A + E328N | L52F + A108V + R354K and/or G284L/S + H287D + E289A |
| DS294 | M63R + R207N + D250V + R325A | L52F + A108V + R354K and/or G284L/S + H287D + E289A |
| DS295 | M63R + R207N + D250V + E328L | L52F + A108V + R354K and/or G284L/S + H287D + E289A |
| DS296 | M63R + R207N + D250V + E328N | L52F + A108V + R354K and/or G284L/S + H287D + E289A |
| DS297 | M63R + R207N + D250V | L52F + A108V + R354K and/or G284L/S + H287D + E289A |
| DS298 | M63R + R207N + R325P + E328L | L52F + A108V + R354K and/or G284L/S + H287D + E289A |
| DS299 | M63R + R207N + R325P + E328N | L52F + A108V + R354K and/or G284L/S + H287D + E289A |
| DS300 | M63R + R207N + R325P | L52F + A108V + R354K and/or G284L/S + H287D + E289A |
| DS301 | M63R + R207N + R325A + E328L | L52F + A108V + R354K and/or G284L/S + H287D + E289A |
| DS173 | M63R + R207N + R325A + E328N | L52F + A108V + R354K and/or G284L/S + H287D + E289A |
| DS303 | M63R + R207N + R325A | L52F + A108V + R354K and/or G284L/S + H287D + E289A |
| DS304 | M63R + R207N + E328L | L52F + A108V + R354K and/or G284L/S + H287D + E289A |
| DS305 | M63R + R207N + E328N | L52F + A108V + R354K and/or G284L/S + H287D + E289A |
| DS306 | M63R + R207N | L52F + A108V + R354K and/or G284L/S + H287D + E289A |
| DS307 | M63R + D250V + R325P + E328L | L52F + A108V + R354K and/or G284L/S + H287D + E289A |
| DS308 | M63R + D250V + R325P + E328N | L52F + A108V + R354K and/or G284L/S + H287D + E289A |
| DS309 | M63R + D250V + R325P | L52F + A108V + R354K and/or G284L/S + H287D + E289A |
| DS310 | M63R + D250V + R325A + E328L | L52F + A108V + R354K and/or G284L/S + H287D + E289A |
| DS311 | M63R + D250V + R325A + E328N | L52F + A108V + R354K and/or G284L/S + H287D + E289A |
| DS312 | M63R + D250V + R325A | L52F + A108V + R354K and/or G284L/S + H287D + E289A |
| DS313 | M63R + D250V + E328L | L52F + A108V + R354K and/or G284L/S + H287D + E289A |
| DS314 | M63R + D250V + E328N | L52F + A108V + R354K and/or G284L/S + H287D + E289A |
| DS315 | M63R + D250V | L52F + A108V + R354K and/or G284L/S + H287D + E289A |
| DS316 | M63R + R325P + E328L | L52F + A108V + R354K and/or G284L/S + H287D + E289A |
| DS317 | M63R + R325P + E328N | L52F + A108V + R354K and/or G284L/S + H287D + E289A |
| DS318 | M63R + R325P | L52F + A108V + R354K and/or G284L/S + H287D + E289A |
| DS319 | M63R + R325A + E328L | L52F + A108V + R354K and/or G284L/S + H287D + E289A |
| DS320 | M63R + R325A + E328N | L52F + A108V + R354K and/or G284L/S + H287D + E289A |
| DS321 | M63R + R325A | L52F + A108V + R354K and/or G284L/S + H287D + E289A |

TABLE 2-continued

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
|---|---|---|
| DS322 | M63R + E328L | L52F + A108V + R354K and/or G284L/S + H287D + E289A |
| DS323 | M63R + E328N | L52F + A108V + R354K and/or G284L/S + H287D + E289A |
| DS324 | M63R | L52F + A108V + R354K and/or G284L/S + H287D + E289A |
| DS433 | M63Q + L131P + R207L + D250V + R325P + E328L | L52F + A108V + R354K and/or G284L/S + H287D + E289A |
| DS434 | M63Q + L131P + R207L + D250V + R325P + E328N | L52F + A108V + R354K and/or G284L/S + H287D + E289A |
| DS435 | M63Q + L131P + R207L + D250V + R325P | L52F + A108V + R354K and/or G284L/S + H287D + E289A |
| DS436 | M63Q + L131P + R207L + D250V + R325A + E328L | L52F + A108V + R354K and/or G284L/S + H287D + E289A |
| DS437 | M63Q + L131P + R207L + D250V + R325A + E328N | L52F + A108V + R354K and/or G284L/S + H287D + E289A |
| DS438 | M63Q + L131P + R207L + D250V + R325A | L52F + A108V + R354K and/or G284L/S + H287D + E289A |
| DS439 | M63Q + L131P + R207L + D250V + E328L | L52F + A108V + R354K and/or G284L/S + H287D + E289A |
| DS440 | M63Q + L131P + R207L + D250V + E328N | L52F + A108V + R354K and/or G284L/S + H287D + E289A |
| DS441 | M63Q + L131P + R207L + D250V | L52F + A108V + R354K and/or G284L/S + H287D + E289A |
| DS442 | M63Q + L131P + R207L + R325P + E328L | L52F + A108V + R354K and/or G284L/S + H287D + E289A |
| DS443 | M63Q + L131P + R207L + R325P + E328N | L52F + A108V + R354K and/or G284L/S + H287D + E289A |
| DS444 | M63Q + L131P + R207L + R325P | L52F + A108V + R354K and/or G284L/S + H287D + E289A |
| DS445 | M63Q + L131P + R207L + R325A + E328L | L52F + A108V + R354K and/or G284L/S + H287D + E289A |
| DS446 | M63Q + L131P + R207L + R325A + E328N | L52F + A108V + R354K and/or G284L/S + H287D + E289A |
| DS447 | M63Q + L131P + R207L + R325A | L52F + A108V + R354K and/or G284L/S + H287D + E289A |
| DS448 | M63Q + L131P + R207L + E328L | L52F + A108V + R354K and/or G284L/S + H287D + E289A |
| DS449 | M63Q + L131P + R207L + E328N | L52F + A108V + R354K and/or G284L/S + H287D + E289A |
| DS450 | M63Q + L131P + R207L | L52F + A108V + R354K and/or G284L/S + H287D + E289A |
| DS451 | M63Q + L131P + R207N + D250V + R325P + E328L | L52F + A108V + R354K and/or G284L/S + H287D + E289A |
| DS452 | M63Q + L131P + R207N + D250V + R325P + E328N | L52F + A108V + R354K and/or G284L/S + H287D + E289A |
| DS453 | M63Q + L131P + R207N + D250V + R325P | L52F + A108V + R354K and/or G284L/S + H287D + E289A |
| DS325 | M63Q + L131P + R207N + D250V + R325A + E328L | L52F + A108V + R354K and/or G284L/S + H287D + E289A |
| DS455 | M63Q + L131P + R207N + D250V + R325A + E328N | L52F + A108V + R354K and/or G284L/S + H287D + E289A |
| DS456 | M63Q + L131P + R207N + D250V + R325A | L52F + A108V + R354K and/or G284L/S + H287D + E289A |
| DS328 | M63Q + L131P + R207N + D250V + E328L | L52F + A108V + R354K and/or G284L/S + H287D + E289A |
| DS458 | M63Q + L131P + R207N + D250V + E328N | L52F + A108V + R354K and/or G284L/S + H287D + E289A |
| DS459 | M63Q + L131P + R207N + D250V | L52F + A108V + R354K and/or G284L/S + H287D + E289A |
| DS460 | M63Q + L131P + R207N + R325P + E328L | L52F + A108V + R354K and/or G284L/S + H287D + E289A |
| DS461 | M63Q + L131P + R207N + R325P + E328N | L52F + A108V + R354K and/or G284L/S + H287D + E289A |
| DS462 | M63Q + L131P + R207N + R325P | L52F + A108V + R354K and/or G284L/S + H287D + E289A |
| DS463 | M63Q + L131P + R207N + R325A + E328L | L52F + A108V + R354K and/or G284L/S + H287D + E289A |
| DS464 | M63Q + L131P + R207N + R325A + E328N | L52F + A108V + R354K and/or G284L/S + H287D + E289A |
| DS465 | M63Q + L131P + R207N + R325A | L52F + A108V + R354K and/or G284L/S + H287D + E289A |
| DS466 | M63Q + L131P + R207N + E328L | L52F + A108V + R354K and/or G284L/S + H287D + E289A |
| DS467 | M63Q + L131P + R207N + E328N | L52F + A108V + R354K and/or G284L/S + H287D + E289A |
| DS468 | M63Q + L131P + R207N | L52F + A108V + R354K and/or G284L/S + H287D + E289A |
| DS469 | M63Q + L131P + D250V + R325P + E328L | L52F + A108V + R354K and/or G284L/S + H287D + E289A |
| DS470 | M63Q + L131P + D250V + R325P + E328N | L52F + A108V + R354K and/or G284L/S + H287D + E289A |
| DS471 | M63Q + L131P + D250V + R325P | L52F + A108V + R354K and/or G284L/S + H287D + E289A |
| DS472 | M63Q + L131P + D250V + R325A + E328L | L52F + A108V + R354K and/or G284L/S + H287D + E289A |
| DS473 | M63Q + L131P + D250V + R325A + E328N | L52F + A108V + R354K and/or G284L/S + H287D + E289A |
| DS474 | M63Q + L131P + D250V + R325A | L52F + A108V + R354K and/or G284L/S + H287D + E289A |
| DS475 | M63Q + L131P + D250V + E328L | L52F + A108V + R354K and/or G284L/S + H287D + E289A |
| DS476 | M63Q + L131P + D250V + E328N | L52F + A108V + R354K and/or G284L/S + H287D + E289A |
| DS477 | M63Q + L131P + D250V | L52F + A108V + R354K and/or G284L/S + H287D + E289A |
| DS478 | M63Q + L131P + R325P + E328L | L52F + A108V + R354K and/or G284L/S + H287D + E289A |
| DS479 | M63Q + L131P + R325P + E328N | L52F + A108V + R354K and/or G284L/S + H287D + E289A |
| DS354 | M63Q + L131P + R325P | L52F + A108V + R354K and/or G284L/S + H287D + E289A |
| DS481 | M63Q + L131P + R325A + E328L | L52F + A108V + R354K and/or G284L/S + H287D + E289A |
| DS482 | M63Q + L131P + R325A + E328N | L52F + A108V + R354K and/or G284L/S + H287D + E289A |
| DS483 | M63Q + L131P + R325A | L52F + A108V + R354K and/or G284L/S + H287D + E289A |
| DS484 | M63Q + L131P + E328L | L52F + A108V + R354K and/or G284L/S + H287D + E289A |
| DS485 | M63Q + L131P + E328N | L52F + A108V + R354K and/or G284L/S + H287D + E289A |
| DS486 | M63Q + L131P | L52F + A108V + R354K and/or G284L/S + H287D + E289A |
| DS595 | M63Q + R207L + D250V + R325P + E328L | L52F + A108V + R354K and/or G284L/S + H287D + E289A |
| DS596 | M63Q + R207L + D250V + R325P + E328N | L52F + A108V + R354K and/or G284L/S + H287D + E289A |
| DS597 | M63Q + R207L + D250V + R325P | L52F + A108V + R354K and/or G284L/S + H287D + E289A |
| DS598 | M63Q + R207L + D250V + R325A + E328L | L52F + A108V + R354K and/or G284L/S + H287D + E289A |
| DS599 | M63Q + R207L + D250V + R325A + E328N | L52F + A108V + R354K and/or G284L/S + H287D + E289A |
| DS600 | M63Q + R207L + D250V + R325A | L52F + A108V + R354K and/or G284L/S + H287D + E289A |
| DS601 | M63Q + R207L + D250V + E328L | L52F + A108V + R354K and/or G284L/S + H287D + E289A |
| DS602 | M63Q + R207L + D250V + E328N | L52F + A108V + R354K and/or G284L/S + H287D + E289A |
| DS603 | M63Q + R207L + D250V | L52F + A108V + R354K and/or G284L/S + H287D + E289A |
| DS604 | M63Q + R207L + R325P + E328L | L52F + A108V + R354K and/or G284L/S + H287D + E289A |
| DS605 | M63Q + R207L + R325P + E328N | L52F + A108V + R354K and/or G284L/S + H287D + E289A |
| DS606 | M63Q + R207L + R325P | L52F + A108V + R354K and/or G284L/S + H287D + E289A |
| DS607 | M63Q + R207L + R325A+ E328L | L52F + A108V + R354K and/or G284L/S + H287D + E289A |
| DS608 | M63Q + R207L + R325A+ E328N | L52F + A108V + R354K and/or G284L/S + H287D + E289A |
| DS609 | M63Q + R207L + R325A | L52F + A108V + R354K and/or G284L/S + H287D + E289A |
| DS610 | M63Q + R207L + E328L | L52F + A108V + R354K and/or G284L/S + H287D + E289A |
| DS611 | M63Q + R207L + E328N | L52F + A108V + R354K and/or G284L/S + H287D + E289A |

TABLE 2-continued

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
| --- | --- | --- |
| DS612 | M63Q + R207L | L52F + A108V + R354K and/or G284L/S + H287D + E289A |
| DS613 | M63Q + R207N + D250V + R325P + E328L | L52F + A108V + R354K and/or G284L/S + H287D + E289A |
| DS614 | M63Q + R207N + D250V + R325P + E328N | L52F + A108V + R354K and/or G284L/S + H287D + E289A |
| DS615 | M63Q + R207N + D250V + R325P | L52F + A108V + R354K and/or G284L/S + H287D + E289A |
| DS616 | M63Q + R207N + D250V + R325A + E328L | L52F + A108V + R354K and/or G284L/S + H287D + E289A |
| DS617 | M63Q + R207N + D250V + R325A + E328N | L52F + A108V + R354K and/or G284L/S + H287D + E289A |
| DS618 | M63Q + R207N + D250V + R325A | L52F + A108V + R354K and/or G284L/S + H287D + E289A |
| DS619 | M63Q + R207N + D250V + E328L | L52F + A108V + R354K and/or G284L/S + H287D + E289A |
| DS620 | M63Q + R207N + D250V + E328N | L52F + A108V + R354K and/or G284L/S + H287D + E289A |
| DS621 | M63Q + R207N + D250V | L52F + A108V + R354K and/or G284L/S + H287D + E289A |
| DS622 | M63Q + R207N + R325P + E328L | L52F + A108V + R354K and/or G284L/S + H287D + E289A |
| DS623 | M63Q + R207N + R325P + E328N | L52F + A108V + R354K and/or G284L/S + H287D + E289A |
| DS624 | M63Q + R207N + R325P | L52F + A108V + R354K and/or G284L/S + H287D + E289A |
| DS625 | M63Q + R207N + R325A + E328L | L52F + A108V + R354K and/or G284L/S + H287D + E289A |
| DS626 | M63Q + R207N + R325A + E328N | L52F + A108V + R354K and/or G284L/S + H287D + E289A |
| DS627 | M63Q + R207N + R325A | L52F + A108V + R354K and/or G284L/S + H287D + E289A |
| DS628 | M63Q + R207N + E328L | L52F + A108V + R354K and/or G284L/S + H287D + E289A |
| DS629 | M63Q + R207N + E328N | L52F + A108V + R354K and/or G284L/S + H287D + E289A |
| DS630 | M63Q + R207N | L52F + A108V + R354K and/or G284L/S + H287D + E289A |
| DS631 | M63Q + D250V + R325P + E328L | L52F + A108V + R354K and/or G284L/S + H287D + E289A |
| DS632 | M63Q + D250V + R325P + E328N | L52F + A108V + R354K and/or G284L/S + H287D + E289A |
| DS633 | M63Q + D250V + R325P | L52F + A108V + R354K and/or G284L/S + H287D + E289A |
| DS634 | M63Q + D250V + R325A + E328L | L52F + A108V + R354K and/or G284L/S + H287D + E289A |
| DS635 | M63Q + D250V + R325A + E328N | L52F + A108V + R354K and/or G284L/S + H287D + E289A |
| DS636 | M63Q + D250V + R325A | L52F + A108V + R354K and/or G284L/S + H287D + E289A |
| DS637 | M63Q + D250V + E328L | L52F + A108V + R354K and/or G284L/S + H287D + E289A |
| DS638 | M63Q + D250V + E328N | L52F + A108V + R354K and/or G284L/S + H287D + E289A |
| DS639 | M63Q + D250V | L52F + A108V + R354K and/or G284L/S + H287D + E289A |
| DS640 | M63Q + R325P + E328L | L52F + A108V + R354K and/or G284L/S + H287D + E289A |
| DS641 | M63Q + R325P + E328N | L52F + A108V + R354K and/or G284L/S + H287D + E289A |
| DS642 | M63Q + R325P | L52F + A108V + R354K and/or G284L/S + H287D + E289A |
| DS643 | M63Q + R325A + E328L | L52F + A108V + R354K and/or G284L/S + H287D + E289A |
| DS644 | M63Q + R325A + E328N | L52F + A108V + R354K and/or G284L/S + H287D + E289A |
| DS645 | M63Q + R325A | L52F + A108V + R354K and/or G284L/S + H287D + E289A |
| DS646 | M63Q + E328L | L52F + A108V + R354K and/or G284L/S + H287D + E289A |
| DS647 | M63Q + E328N | L52F + A108V + R354K and/or G284L/S + H287D + E289A |
| DS648 | M63Q | L52F + A108V + R354K and/or G284L/S + H287D + E289A |
| DS757 | L131P + R207L + D250V + R325P + E328L | L52F + A108V + R354K and/or G284L/S + H287D + E289A |
| DS758 | L131P + R207L + D250V + R325P + E328N | L52F + A108V + R354K and/or G284L/S + H287D + E289A |
| DS759 | L131P + R207L + D250V + R325P | L52F + A108V + R354K and/or G284L/S + H287D + E289A |
| DS760 | L131P + R207L + D250V + R325A + E328L | L52F + A108V + R354K and/or G284L/S + H287D + E289A |
| DS761 | L131P + R207L + D250V + R325A + E328N | L52F + A108V + R354K and/or G284L/S + H287D + E289A |
| DS762 | L131P + R207L + D250V + R325A | L52F + A108V + R354K and/or G284L/S + H287D + E289A |
| DS763 | L131P + R207L + D250V + E328L | L52F + A108V + R354K and/or G284L/S + H287D + E289A |
| DS764 | L131P + R207L + D250V + E328N | L52F + A108V + R354K and/or G284L/S + H287D + E289A |
| DS765 | L131P + R207L + D250V | L52F + A108V + R354K and/or G284L/S + H287D + E289A |
| DS766 | L131P + R207L + R325P + E328L | L52F + A108V + R354K and/or G284L/S + H287D + E289A |
| DS767 | L131P + R207L + R325P + E328N | L52F + A108V + R354K and/or G284L/S + H287D + E289A |
| DS768 | L131P + R207L + R325P | L52F + A108V + R354K and/or G284L/S + H287D + E289A |
| DS769 | L131P + R207L + R325A + E328L | L52F + A108V + R354K and/or G284L/S + H287D + E289A |
| DS770 | L131P + R207L + R325A + E328N | L52F + A108V + R354K and/or G284L/S + H287D + E289A |
| DS771 | L131P + R207L + R325A | L52F + A108V + R354K and/or G284L/S + H287D + E289A |
| DS772 | L131P + R207L + E328L | L52F + A108V + R354K and/or G284L/S + H287D + E289A |
| DS773 | L131P + R207L + E328N | L52F + A108V + R354K and/or G284L/S + H287D + E289A |
| DS774 | L131P + R207L | L52F + A108V + R354K and/or G284L/S + H287D + E289A |
| DS775 | L131P + R207N + D250V + R325P + E328L | L52F + A108V + R354K and/or G284L/S + H287D + E289A |
| DS776 | L131P + R207N + D250V + R325P + E328N | L52F + A108V + R354K and/or G284L/S + H287D + E289A |
| DS777 | L131P + R207N + D250V + R325P | L52F + A108V + R354K and/or G284L/S + H287D + E289A |
| DS778 | L131P + R207N + D250V + R325A + E328L | L52F + A108V + R354K and/or G284L/S + H287D + E289A |
| DS779 | L131P + R207N + D250V + R325A + E328N | L52F + A108V + R354K and/or G284L/S + H287D + E289A |
| DS780 | L131P + R207N + D250V + R325A | L52F + A108V + R354K and/or G284L/S + H287D + E289A |
| DS781 | L131P + R207N + D250V + E328L | L52F + A108V + R354K and/or G284L/S + H287D + E289A |
| DS782 | L131P + R207N + D250V + E328N | L52F + A108V + R354K and/or G284L/S + H287D + E289A |
| DS783 | L131P + R207N + D250V | L52F + A108V + R354K and/or G284L/S + H287D + E289A |
| DS784 | L131P + R207N + R325P + E328L | L52F + A108V + R354K and/or G284L/S + H287D + E289A |
| DS785 | L131P + R207N + R325P + E328N | L52F + A108V + R354K and/or G284L/S + H287D + E289A |
| DS786 | L131P + R207N + R325P | L52F + A108V + R354K and/or G284L/S + H287D + E289A |
| DS787 | L131P + R207N + R325A + E328L | L52F + A108V + R354K and/or G284L/S + H287D + E289A |
| DS788 | L131P + R207N + R325A + E328N | L52F + A108V + R354K and/or G284L/S + H287D + E289A |
| DS789 | L131P + R207N + R325A | L52F + A108V + R354K and/or G284L/S + H287D + E289A |
| DS790 | L131P + R207N + E328L | L52F + A108V + R354K and/or G284L/S + H287D + E289A |
| DS791 | L131P + R207N + E328N | L52F + A108V + R354K and/or G284L/S + H287D + E289A |
| DS792 | L131P + R207N | L52F + A108V + R354K and/or G284L/S + H287D + E289A |
| DS793 | L131P + D250V + R325P + E328L | L52F + A108V + R354K and/or G284L/S + H287D + E289A |

TABLE 2-continued

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
| --- | --- | --- |
| DS794 | L131P + D250V + R325P + E328N | L52F + A108V + R354K and/or G284L/S + H287D + E289A |
| DS795 | L131P + D250V + R325P | L52F + A108V + R354K and/or G284L/S + H287D + E289A |
| DS796 | L131P + D250V + R325A + E328L | L52F + A108V + R354K and/or G284L/S + H287D + E289A |
| DS797 | L131P + D250V + R325A + E328N | L52F + A108V + R354K and/or G284L/S + H287D + E289A |
| DS798 | L131P + D250V + R325A | L52F + A108V + R354K and/or G284L/S + H287D + E289A |
| DS799 | L131P + D250V + E328L | L52F + A108V + R354K and/or G284L/S + H287D + E289A |
| DS800 | L131P + D250V + E328N | L52F + A108V + R354K and/or G284L/S + H287D + E289A |
| DS801 | L131P + D250V | L52F + A108V + R354K and/or G284L/S + H287D + E289A |
| DS802 | L131P + R325P + E328L | L52F + A108V + R354K and/or G284L/S + H287D + E289A |
| DS803 | L131P + R325P + E328N | L52F + A108V + R354K and/or G284L/S + H287D + E289A |
| DS804 | L131P + R325P | L52F + A108V + R354K and/or G284L/S + H287D + E289A |
| DS805 | L131P + R325A + E328L | L52F + A108V + R354K and/or G284L/S + H287D + E289A |
| DS806 | L131P + R325A + E328N | L52F + A108V + R354K and/or G284L/S + H287D + E289A |
| DS807 | L131P + R325A | L52F + A108V + R354K and/or G284L/S + H287D + E289A |
| DS808 | L131P + E328L | L52F + A108V + R354K and/or G284L/S + H287D + E289A |
| DS809 | L131P + E328N | L52F + A108V + R354K and/or G284L/S + H287D + E289A |
| DS810 | L131P | L52F + A108V + R354K and/or G284L/S + H287D + E289A |
| DS921 | R207L + D250V + R325P | L52F + A108V + R354K and/or G284L/S + H287D + E289A |
| DS922 | R207L + D250V + R325A + E328L | L52F + A108V + R354K and/or G284L/S + H287D + E289A |
| DS923 | R207L + D250V + R325A + E328N | L52F + A108V + R354K and/or G284L/S + H287D + E289A |
| DS924 | R207L + D250V + R325A | L52F + A108V + R354K and/or G284L/S + H287D + E289A |
| DS925 | R207L + D250V + E328L | L52F + A108V + R354K and/or G284L/S + H287D + E289A |
| DS926 | R207L + D250V + E328N | L52F + A108V + R354K and/or G284L/S + H287D + E289A |
| DS927 | R207L + D250V | L52F + A108V + R354K and/or G284L/S + H287D + E289A |
| DS928 | R207L + R325P + E328L | L52F + A108V + R354K and/or G284L/S + H287D + E289A |
| DS929 | R207L + R325P + E328N | L52F + A108V + R354K and/or G284L/S + H287D + E289A |
| DS930 | R207L + R325P | L52F + A108V + R354K and/or G284L/S + H287D + E289A |
| DS931 | R207L + R325A + E328L | L52F + A108V + R354K and/or G284L/S + H287D + E289A |
| DS932 | R207L + R325A + E328N | L52F + A108V + R354K and/or G284L/S + H287D + E289A |
| DS933 | R207L + R325A | L52F + A108V + R354K and/or G284L/S + H287D + E289A |
| DS934 | R207L + E328L | L52F + A108V + R354K and/or G284L/S + H287D + E289A |
| DS935 | R207L + E328N | L52F + A108V + R354K and/or G284L/S + H287D + E289A |
| DS936 | R207L | L52F + A108V + R354K and/or G284L/S + H287D + E289A |
| DS937 | R207N + D250V + R325P + E328L | L52F + A108V + R354K and/or G284L/S + H287D + E289A |
| DS938 | R207N + D250V + R325P + E328N | L52F + A108V + R354K and/or G284L/S + H287D + E289A |
| DS939 | R207N + D250V + R325P | L52F + A108V + R354K and/or G284L/S + H287D + E289A |
| DS940 | R207N + D250V + R325A + E328L | L52F + A108V + R354K and/or G284L/S + H287D + E289A |
| DS941 | R207N + D250V + R325A + E328N | L52F + A108V + R354K and/or G284L/S + H287D + E289A |
| DS942 | R207N + D250V + R325A | L52F + A108V + R354K and/or G284L/S + H287D + E289A |
| DS943 | R207N + D250V + E328L | L52F + A108V + R354K and/or G284L/S + H287D + E289A |
| DS944 | R207N + D250V + E328N | L52F + A108V + R354K and/or G284L/S + H287D + E289A |
| DS945 | R207N + D250V | L52F + A108V + R354K and/or G284L/S + H287D + E289A |
| DS946 | R207N + R325P + E328L | L52F + A108V + R354K and/or G284L/S + H287D + E289A |
| DS947 | R207N + R325P + E328N | L52F + A108V + R354K and/or G284L/S + H287D + E289A |
| DS948 | R207N + R325P | L52F + A108V + R354K and/or G284L/S + H287D + E289A |
| DS949 | R207N + R325A + E328L | L52F + A108V + R354K and/or G284L/S + H287D + E289A |
| DS950 | R207N + R325A + E328N | L52F + A108V + R354K and/or G284L/S + H287D + E289A |
| DS951 | R207N + R325A | L52F + A108V + R354K and/or G284L/S + H287D + E289A |
| DS952 | R207N + E328L | L52F + A108V + R354K and/or G284L/S + H287D + E289A |
| DS953 | R207N + E328N | L52F + A108V + R354K and/or G284L/S + H287D + E289A |
| DS954 | R207N | L52F + A108V + R354K and/or G284L/S + H287D + E289A |
| DS955 | D250V + R325P + E328L | L52F + A108V + R354K and/or G284L/S + H287D + E289A |
| DS956 | D250V + R325P + E328N | L52F + A108V + R354K and/or G284L/S + H287D + E289A |
| DS957 | D250V + R325P | L52F + A108V + R354K and/or G284L/S + H287D + E289A |
| DS958 | D250V + R325A + E328L | L52F + A108V + R354K and/or G284L/S + H287D + E289A |
| DS959 | D250V + R325A + E328N | L52F + A108V + R354K and/or G284L/S + H287D + E289A |
| DS960 | D250V + R325A | L52F + A108V + R354K and/or G284L/S + H287D + E289A |
| DS961 | D250V + E328L | L52F + A108V + R354K and/or G284L/S + H287D + E289A |
| DS962 | D250V + E328N | L52F + A108V + R354K and/or G284L/S + H287D + E289A |
| DS963 | D250V | L52F + A108V + R354K and/or G284L/S + H287D + E289A |
| DS964 | R325P + E328L | L52F + A108V + R354K and/or G284L/S + H287D + E289A |
| DS965 | R325P + E328N | L52F + A108V + R354K and/or G284L/S + H287D + E289A |
| DS966 | R325P | L52F + A108V + R354K and/or G284L/S + H287D + E289A |
| DS967 | R325A + E328L | L52F + A108V + R354K and/or G284L/S + H287D + E289A |
| DS968 | R325A + E328N | L52F + A108V + R354K and/or G284L/S + H287D + E289A |
| DS969 | R325A | L52F + A108V + R354K and/or G284L/S + H287D + E289A |
| DS970 | E328L | L52F + A108V + R354K and/or G284L/S + H287D + E289A |
| DS971 | E328N | L52F + A108V + R354K and/or G284L/S + H287D + E289A |
| DS919 | R207L + D250V + R325P + E328L | L52F + A108V + R354K and/or G284L/S + H287D + E289A |
| DS920 | R207L + D250V + R325P + E328N | L52F + A108V + R354K and/or G284L/S + H287D + E289A |

According to some embodiments, a variant of TdT has a substitution or combination of substitutions described above and has an amino acid sequence within at least 80% identity with SEQ ID NO:2 or with a functionally equivalent sequence (such as, SEQ ID NOs:11, 13, 15, 17, 19, 21, 23, 25, 27, 29, 31, 33 or 35); in some embodiments, such amino acid sequence is within at least 85%, 90%, 95%, 96%, 97%, 98%, or 99% identity with SEQ ID NO:2 or functionally equivalent sequence (such as, SEQ ID NOs:11, 13, 15, 17, 19, 21, 23, 25, 27, 29, 31, 33 or 35).

Additional Modifications

In an embodiment, the variant of TdT further includes any type of tagging peptide in its N-terminal, C-terminal or both extremity, such as a His-tag sequence. Said tagging peptide could be used for purification, identification, increasing expression, secretability or increasing catalytic activity. It will be understood that such different tags are extensively described in the literature and thus all tag known to a skilled person are covered by the present invention.

The variants of the invention can also include one or more exogenous or heterologous features at the N- and/or C-terminal regions of the protein for use, e.g., in the purification of the recombinant polymerase.

The variant of the invention may further comprise a substitution of residues between positions C378 to L406, wherein the positions are numbered by reference to the amino acid sequence set forth in SEQ ID NO1, or functionally equivalent residues, by residues H363 to C390 of the Polµ polymerase of sequence SEQ ID NO:3, wherein the positions are numbered by reference to the amino acid sequence set forth in SEQ ID NO:3 or functionally equivalent residues.

Advantageously, the variant of TdT comprises at least the amino acid sequence SEQ ID NO:2, 11, 13, 15, 17, 19, 21, 23, 25, 27, 29, 31, 33 or 35, with the disclosed substitution(s) and percent sequence identity values.

Nucleic Acids, Expression Cassette, Vector

It is also the purpose of the invention to provide a nucleic acid molecule encoding a variant of the invention. As used herein, the term "nucleic acid", "nucleic sequence," "polynucleotide", "oligonucleotide" and "nucleotide sequence" are used interchangeably and refer to a sequence of deoxyribonucleotides and/or ribonucleotides. In one embodiment, the nucleic acid is a DNA. In an alternative embodiment, the nucleic acid is RNA. In an alternative embodiment, the nucleic acid is XNA.

The nucleic acids can be in single stranded form or in duplex form or a mixture of the two. It can be of recombinant, artificial and/or synthetic origin and it can comprise modified nucleotides. Such modifications could be natural modifications such as epigenetic modifications, or unnatural modification such as labels, modified bond, a modified purine or pyrimidine base, or a modified sugar. In one embodiment, nucleic acid molecules are DNA, RNA or XNA bearing naturally occurring epigenetic modifications such as methylation, hydroxymethylation, formylation or 5-carboxylation. In one embodiment, nucleic acid molecules are DNA, RNA or XNA bearing unnaturally occurring modifications such as fluorescent tag, fluorescent label, interaction groups.

The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding a TdT variant as defined above. Such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding a TdT variant of the invention, wherein the sequence of said nucleic acids, or a portion of said sequence at least, has been engineered using optimized codon usage.

Alternatively, the nucleic acids according to the invention may be deduced from the sequence of the TdT variant according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

In one embodiment, nucleic acid molecules are polymeric molecules having length of more than 50, 100, 200, 300, 400, 500, 600, 700, 800, 900, 1 000, 2 000, 3 000, 4 000, 5 000, 6 000, 7 000, 8 000, 9 000, 10 000, 15 000, 20 000, 30 000, 40 000, 50 000 or 100 000 nucleotides.

Nucleic acids of the invention may further comprise additional nucleotide sequences, such as regulatory regions, i.e., promoters, enhancers, silencers, terminators, signal peptides and the like that can be used to cause or regulate expression of the polypeptide in a selected host cell or system.

The present invention further relates to an expression cassette comprising a nucleic acid according to the invention operably linked to one or more control sequences that direct the expression of said nucleic acid in a suitable host cell. Typically, the expression cassette comprises, or consists of, a nucleic acid according to the invention operably linked to a control sequence such as transcriptional promoter and/or transcription terminator. The control sequence may include a promoter that is recognized by a host cell or an in vitro expression system for expression of a nucleic acid encoding a TdT variant of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell. The control sequence may also be a transcription terminator, which is recognized by a host cell to terminate transcription. The terminator is operably linked to the 3'-terminus of the nucleic acid encoding the esterase. Any terminator that is functional in the host cell may be used in the present invention. Typically, the expression cassette comprises, or consists of, a nucleic acid according to the invention operably linked to a transcriptional promoter and a transcription terminator.

The invention also relates to a vector comprising a nucleic acid or an expression cassette as defined above.

The term "vector" refers to DNA molecule used as a vehicle to transfer recombinant genetic material into a host cell. The major types of vectors are plasmids, bacteriophages, viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. Generally, the regulatory elements that are present in an expression vector include a transcriptional promoter, a ribosome binding site, a terminator, and optionally present operator. An expression vector can also contain an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. The choice of the vector will typically depend on the compatibility of the vector with the host cell into which the vector is to be introduced.

It is another object of the invention to provide a host cell comprising a nucleic acid, an expression cassette or a vector as described above. The present invention thus relates to the use of a nucleic acid, expression cassette or vector according to the invention to transform, transfect or transduce a host cell. The choice of the vector will typically depend on the compatibility of the vector with the host cell into which it must be introduced.

According to the invention, the host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The term "host cell" also encompasses any progeny of a parent host cell that is not identical to the parent host cell due to mutations that occur during replication. The host cell may be any cell useful in the production of a variant of the present invention, e.g., a prokaryote or a eukaryote. The prokaryotic host cell may be any Gram-positive or Gram-negative bacterium. The host cell may also be an eukaryotic cell, such as a yeast, fungal, mammalian, insect or plant cell.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation, Optionally, more than one copy of a nucleic acid, cassette or vector of the present invention may be inserted into a host cell to increase production of the variant.

Modified Nucleotides

According to the invention, the variants of TdT are able to incorporate modified nucleotides, such as modified 3'O— nucleotides, including 3'O-blocked nucleotides.

In the context of the invention, the expression "Modified Nucleotide" refers to a molecule containing a nucleoside (i.e. a base attached to a deoxyribose or ribose sugar molecule) bound to three phosphate groups which has at least one additional group on one of its extremity: 2', 3', 5' or base. Said additional group blocks further addition of nucleotides by preventing the formation of any phosphodiester bond (3'O-modification, 2' or 2'O modifications) or by sterically preventing the polymerase to attach to any nucleic acid fragments that comprises on its 3' extremity such modified nucleotide (5' or base modification). Furtherly, said additional group has advantageously a reversible nature allowing that group to be removed through a specific cleaving reaction.

Nucleosides or nucleotide triphosphates include deoxyadenosine triphosphate (dATP), deoxyguanosine triphosphate (dGTP), deoxycytidine triphosphate (dCTP) or deoxythymidine triphosphate (dTTP) for examples of nucleotide containing deoxyribose. Adenosine triphosphate (ATP), guanosine triphosphate (GTP), cytidine triphosphate (CTP) or uridine triphosphate (UTP) are further examples of nucleotide triphosphates containing ribose. Other types of nucleosides may be bound to three phosphates to form nucleotide triphosphates, such as naturally occurring modified nucleosides and artificial nucleosides.

In a particular embodiment, the modified nucleotide is a 3'O-blocked nucleotide, which comprises a group reversibly attached to the 3' end of the nucleotide triphosphate to prevent further nucleotide addition. Said group could have diverse chemical natures, such as azidomethyl, aminoxy, and allyl.

Advantageously, the modified nucleotide is selected from a 3'-O—NH$_2$-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

wherein —Z is any of —C(R')2-O—R", —C(R')2-N(R")2, —C(R')2-N(H)R", —C(R')2-S—R" and —C(R')2-F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')2 represents an alkylidene group of formula =C(R''')2 wherein each R''' may be the same or different and is selected from the group comprising hydrogen and halogen atoms and alkyl groups, with the proviso that in some embodiments the alkyl of each R" has from 1 to 3 carbon atoms; and wherein the molecule may be reacted to yield an intermediate in which each R" is exchanged for H or, where Z is —(R')2-F, the F is exchanged for OH, SH or NH2, preferably OH, which intermediate dissociates under aqueous conditions to afford a molecule with a free 3'-OH; with the proviso that where Z is —C(R')2-S—R", both R groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, —Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less.

In a further particular embodiment, "3'O modified nucleotide" refers to nucleotide triphosphate bearing at the 3' extremity either a 3'-O-methyl, 3'-azido, 3'-O-azidomethyl, 3'-O-amino, 3'-aminoxy or 3'-O-allyl group. In a further embodiment, the 3'-blocked nucleotide triphosphate is blocked by either a 3'-O-azidomethyl, 3'-aminoxy or 3'-O-allyl group. In other embodiments, "3'O modified nucleotide" refers to nucleotide triphosphate bearing at the 3' extremity either esters, ethers, carbonitriles, phosphates, carbonates, carbamates, hydroxylamine, borates, nitrates, sugars, phosphoramide, phosphoramidates, phenylsulfonates, sulfates, sulfones or amino acids. In some embodiments, the foregoing 3'-O-blocking groups have a molecule weight of 100 or less.

In another embodiments, 3'-O-blocking groups of the invention include methyl, 3'-0-(2-nitrobenzyl), allyl, amine, azidomethyl, tert-butoxy ethoxy, or propargyl.

In further particular embodiment, "3'O modified nucleotide" refers to a nucleotide triphosphate having a terminator effector modifying group such as those described in WO2016034807.

Interestingly, the variants of the invention exhibit an increased affinity for modified nucleotides, as compared to wild type TdT, and thereby an increased ability to incorporate such modified nucleotide in a nucleic acid sequence during nucleic acid synthesis. More particularly, the variants of the invention are able to use and incorporate modified 3'O— nucleotides (and more particularly, 3'O-blocked nucleotide) in nucleic acid sequence, which is not possible with wild type TdT (see Knapp et al. Chem. Eur. J., 2011, 17:2903).

According to a particular aspect, the invention relates to variants of TdT able to work with modified nucleotides in a nucleic acids enzymatic synthesis process, particularly with 3'O-modified nucleotides (e.g., 3'O-blocked nucleotide), and having the ability to produce long length nucleic acid molecules or derivative of nucleic acid molecules.

Enzymatic Synthesis of Nucleic Acid

It is the purpose of the present invention to provide variants of TdT that may be used for the synthesis of nucleic acid, such as described in Ybert et al, WO2015/159023; Jensen et al, Biochemistry, 57: 1821-1832 (2018); Hiatt et al, U.S. Pat. No. 5,808,045. More particularly, it is the purpose of the present invention to provide variants of TdT suitable to add modified nucleotides, to an initiating nucleic acid strand. The blocking group may be then removed for allowing a new addition of modified nucleotide.

According to the invention, by use of a variant of the invention, it is possible to implement successive cycles comprising additions and deprotections. This process will therefore allow by multiple cycles of addition of a reversible modified nucleotide and further removal of the blocking group to allow the controlled extension of an initiating nucleic acid strand into a defined sequence.

The present invention contemplates the use of modified TdT according to the present invention in any enzymatic nucleic acid synthesis process.

It is thus an object of the present invention to provide a method of synthesizing a polynucleotide having a predetermined sequence, comprising the steps of:
a) providing an initiator having a 3'-terminal nucleotide having a free 3'-hydroxyl;
b) repeating cycles of (i) contacting under elongation conditions the initiator or elongated fragments having free 3'-O-hydroxyls with a 3'-O-blocked nucleoside triphosphate and a TdT variant of the present invention, so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until the polynucleotide is formed.

It is also the purpose of the present invention to provide a process for synthesizing a nucleic acid molecule without template, comprising a step of contacting a nucleic acid primer with both at least one nucleotide, such as at least one 3'O-modified nucleotide, and a variant of the invention.

The present invention contemplates the concept of enzymatic nucleic acids synthesis process. In such process, nucleic acids molecules are de novo synthesized in absence of any template strand. Accordingly, ordered sequence of nucleotides are coupled to an initiator nucleic acid fragment with the help of the variant of the invention. It will be understood that quantitative coupling and more generally high coupling efficiency of each nucleotide to the growing nucleic acid chain is of great importance. It will also be understood that non-terminator nucleotides, such as natural nucleotides or permanent labeled nucleotides, will not permit any control over the sequence synthesized and will result, for example, in uncontrolled and undesired poly-additions.

In some embodiments, the method of synthesizing a polynucleotide comprises the steps of (a) providing an initiator having a free 3'-hydroxyl; (b) reacting under extension conditions the initiator or an extension intermediate having a free 3'-hydroxyl with a variant TdT of the invention in the presence of a 3'-O-blocked nucleoside triphosphate to produce a 3'-O-blocked extension intermediate; (c) deblocking the extension intermediate to produce an extension intermediate with a free 3'-hydroxyl; and (d) repeating steps (b) and (c) until the polynucleotide is synthesized.

In some embodiments, the method of synthesizing a polynucleotide comprises the steps of (a) providing an initiator attached to a solid support, the intiator being an oligonucleotide having a free 3'-hydroxyl; (b) reacting under extension conditions the initiator or an extension intermediate having a free 3'-hydroxyl with a variant TdT of the invention in the presence of a 3'-O-blocked nucleoside triphosphate to produce a 3'-O-blocked extension intermediate; (c) washing the solid support to remove unincorporated 3'-O-blocked nucleoside triphosphate; (d) deblocking the extension intermediate by exposing the solid support to a deblocking agent to produce an extension intermediate having a free 3'-hydroxyl; and (e) repeating steps (b) and (d) until the polynucleotide is synthesized. The method may include a further step of cleaving the completed polynucleotide from the solid support.

In some embodiments, for TdT catalyzed addition reactions, the enzymatic conditions may contain from about 0.20 and about 200 µM of the nucleotide having the removable blocking moiety protecting the 3'-hydroxyl and from about 0.20 to 200 µM of free and unmodified 3'-hydroxyls derived from the initiating substrate. In some embodiments, the reaction buffer contains from about 10 to about 500 mM potassium cacodylate buffer (pH between 6.5 and 7.5). and from about 0.01 to about 10 mM of a divalent cation (e.g. $CoCl_2$ or $MnCl_2$). Other buffer compositions and components may be suitable for particular desired embodiment of the present invention.

In the context of the invention, the expression "cleaving reaction" refers to any action of substance or physical conditions, which is able to cleave the additional group previously described on reversible modified nucleotides. A person skilled in the art is able to determine a cleaving reaction for any previously listed group.

In one embodiment, the cleaving agent is a chemical cleaving agent. In an alternative embodiment, the cleaving agent is an enzymatic cleaving agent.

It will be understood by the person skilled in the art that the selection of cleaving agent is dependent on the type of 3'-nucleotide blocking group used. For example, tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiment, the cleaving reaction is involving: TCEP, a palladium complex or sodium nitrite.

In particular embodiment, the cleaving reaction is performed in the presence of additional components such as denaturant (urea, guanidinium chloride, formamide or betaine for example). In a further embodiment, the cleavage reaction is performed with one or more buffers. It will be understood by the person skilled in the art that the choice of buffer is dependent on the exact mechanism of reaction.

The present invention relates to variants of TdT with the capacity to incorporate, in a quantitative way, modified nucleotides. By "quantitative way" or "quantitative reaction", it is meant a reaction that goes to completion, i.e. in which reactants are totally converted into the product. Polymerase that incorporates in a quantitative way reversible modified nucleotide is a polymerase able to elongate every fragment of nucleic acid with all the nucleotides available leading to the conversion of all the initiating fragments of length n, to fragments of length n+1.

As used herein, "initiating fragment" refers to a short oligonucleotide sequence with a free 3'-end, which can be further elongated. In one embodiment, the initiating fragment is a DNA initiating fragment. In an alternative embodiment, the initiating fragment is an RNA initiating fragment.

In one embodiment, the initiating fragment possesses between 3 and 100 nucleotides, in particular between 3 and 20 nucleotides.

In one embodiment, the initiating fragment is single-stranded. In an alternative embodiment, the initiating fragment is double-stranded.

In one embodiment, the initiating fragment is immobilized on a solid support. The initiating fragment may be attached with various method to a solid support resulting in a stable under the various enzymatic or synthesis reaction conditions that the fragment will undergo.

In one embodiment, the initiating fragment is immobilized on a solid support via a reversible interacting moiety, such as a chemically-cleavable linker, an antibody/immunogenic epitope, a biotin/biotin-binding protein or glutathione-GST tag. In a further embodiment, the initiating fragment is immobilized on a solid support via a chemically-cleavable linker, such as a disulfide, allyl, or azide-masked hemiaminal ether linker.

In an initiating fragment, the immobilized part contains at least one restriction site. The use of restriction enzymes and restriction sites to selectively hydrolyze nucleic acids chain at a specific site is describe in the literature. Any skilled person will be able to choose the appropriate restriction enzyme that will match the initiating fragment cleaving site sequence.

In an alternative embodiment, the initiating fragment contains at least one uridine. Treatment with uracil-DNA glycosylase (UDG) generates an abasic site. Treatment on an appropriate substrate with an apurinic/apyrimidinic (AP) site endonuclease will extract the nucleic acid strand.

Applications

Described herein is the use of variants of TdT to be used for nucleic acid synthesis, oligonucleotide synthesis, probe synthesis, tagging, nucleic acid amplification, aptamers, therapeutic nucleic acid molecules, drug target discovery and validation, disease diagnosis, metabolic engineering, data storage, crops improvement, library design, sequencing pools, nucleic acid labeling or attachment or any other application that is involving nucleic acid molecules.

Production of Variant TdTs

Variants of the invention may be produced by mutating known reference or wild type TdT-coding polynucleotides, then expressing it using conventional molecular biology techniques. For example, the mouse TdT gene (SEQ ID NO:1) may be assembled from synthetic fragments using conventional molecular biology techniques, e.g. using protocols described by Stemmer et al, Gene, 164: 49-53 (1995); Kodumal et al, Proc. Natl. Acad. Sci., 101: 15573-15578 (2004); or the like, or it may be directly cloned from mouse cells using protocols described by Boule et al, Mol. Biotechnology, 10: 199-208 (1998), or Bentolila et al, EMBO J., 14: 4221-4229 (1995); or the like.

For example, an isolated TdT gene may be inserted into an expression vector, such as pET32 (Novagen) to give a vector pCTdT which then may be used to make and express variant TdT proteins using conventional protocols. Vectors with the correct sequence may be transformed in E. coli producer strains.

Transformed strains are cultured using conventional techniques to pellets from which TdT protein is extracted. For example, previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h30 at 10,000 rpm. Centrifugate is pass through a 0.2 μm filter to remove any debris before column purification.

TdT protein may be purified from the centrifugate in a one-step affinity procedure. For example, Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDSPAGE gels.

Kits, Enzyme and Nucleotide Composition

A particular aspect of the invention is relative to the composition and the use of kits comprising a variant of TdT according to the invention, or to any particular aspect of the present invention, with optionally any combination of one or more components selected from: an initiating fragment, one or more reversible terminator nucleotides, additional enzyme and reagents used in a cleaving reaction. Said kits can be used in a method of enzymatic nucleic acid synthesis.

The present invention covers the composition of matter comprising variants of TdT according to the invention, or to any particular aspect of the present invention, with reversible modified nucleotide in a mix with appropriate buffer and ratio concentration.

EXAMPLES

Example 1—Generation, Expression and Purification of Variants of TdT According to the Invention Expression Strain Generation The TdT mouse gene has been generated from the pET28 plasmid described in [Boulé et al., 1998, Mol. Biotechnol. 10, 199-208]. Sequence SEQ ID N°4 (Tag TdT) has been amplified by using the following primers:

```
T7-pro:
                              (SEQ ID NO: 5)
TAATACGACTCACTATAGGG

T7-ter:
                              (SEQ ID NO: 6)
GCTAGTTATTGCTCAGCGG
``` through standard molecular biology techniques. The sequence is then cloned into plasmid pET32 backbone to give the new pCTdT plasmid.

After sequencing pCTdT is transformed into commercial E. coli cells, BL21 (DE3, from Novagen). Growing colonies on plate with kanamycin are isolated and named Ec-CTdT.

Polymerase Variants Generation

The pCTdT vector is used as starting vector. Specific primers comprising one or several point mutations have been generated from Agilent online software (http://www.genomics.agilent.com:80/primerDesignProgram.jsp). The commercially available kit QuickChange II (Agilent) has been used to generate the desired modified polymerase comprising the targeted mutations. Experimental procedure has followed the supplier's protocol. After generation of the different vectors, each of them have been sequenced. Vectors with the correct sequence have been transformed in E. coli producer strains, as described before. Clones able to grow on kanamycin LB-agar plates are isolated.

Expression

The Ec-CTdT and Ec-DSi or Ec-DSi' strains have been used for inoculating 250 mL erlens with 50 mL of LB media supplemented with appropriate amount of kanamycin. After overnight growth at 37° C., appropriate volumes of these pre-cultures have been used to inoculate 5 L erlens with 2 L LB media with kanamycin. The initial OD for the 5 L cultures is chosen to be 0.01. The erlens are put at 37° C. under strong agitation and the OD of the different cultures are regularly checked. After reaching an OD comprised between 0.6 and 0.9 each erlen is supplemented by the addition of 1 mL of 1M IPTG (Isopropyl β-D-1-thiogalactopyranoside, Sigma). The erlens are put back to agitation under a controlled temperature of 37° C. After overnight expression, the cells are harvested in several pellets. Pellets expressing the same variants are pooled and stored at −20° C., eventually for several months.

Extraction

Previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h30 at 10,000 rpm. Centrifugate is pass through a 0.2 µm filter to remove any debris before column purification.

Purification

A one-step affinity procedure is used to purify the produced and extracted polymerase enzymes. A Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH$_4$]$_2$SO$_4$) The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDS-PAGE gels.

Results are presented by FIG. 1. The gel shows, for each TdT (both variants and wild-type), the column flowthrough (FT) and the different fractions F1 to F4, corresponding to the elution peaks. A molecular weight marker (M) was also loaded in the gel. FIG. 1 shows that the variants of TdT according to the invention present a high purity level (about 90%) and a good expression as compared to TdT wild-type (see columns F2 and/or F3).

Example 2—Evaluation of the Activity of Variants of TdT with Fluorescent Primers Activity Test Elongation performance of TdT variants of SEQ ID NO: 2: DS11 (M63R+L131P+C173R+R207L+R325P+E328N) DS29 (M63R+L131P+C173R+R207N+R325P+E328N), DS173 (M63R+C173R+R207L+R325P+E328N), DS659

(L131P+C173R+R207L+R325P+E328N), DS874 (C173G+R207L+R325P+E328L) generated, expressed and purified according to example 1 is evaluated through the following assay. All the results are compared with each other and with the wild type TdT enzyme (SEQ ID N°1) and to a control tube lacking any polymerase enzyme.

TABLE 7

Activity test

| Reagent | Concentration | Volume |
|---|---|---|
| $H_2O$ | — | 12 µL |
| Activity Buffer | 10x | 2 µL |
| dNTP | 250 µM | 2 µL |
| Purified enzyme | 20 µM | 2 µL |
| Fluorescent primer DNA | 500 nM | 2 µL |

The Activity buffer comprises, for example, TdT reaction buffer (available from New England Biolabs) supplemented with $CoCl_2$. Primer used is the following:

(SEQ ID NO: 7)
5'-AAAAAAAAAAAAAAGGGG-3'

The primer has also an ATTO fluorescent dye on the 5' extremity.

Nucleotides used (noted as dNTP in table 7) are 3'-O-amino-2',3'-dideoxynucleotides-5'-triphosphate ($ONH_2$, Firebird Biosciences) such as 3'-O-amino-2',3'-dideoxyadenosine-5'-triphosphate for example.

For each different variant tested, one tube is used for the reaction. The reagents are added in the tube, starting from water, and then in the order of Table 7. After 30 min at 37° C. the reaction is stopped by addition of formamide (Sigma).

Analysis

The analysis is involving polyacrylamide gel analysis. Samples from activity test are analyzed through polyacrylamide 16% (biorad) denaturing gel. Gels are made just before the analysis by pouring polyacrylamide inside glass plates and let it polymerize. The gel inside the glass plates is mounted on an adapted tank filed with TBE buffer (Sigma) for the electrophoresis step. The samples to be analyzed are loaded on the top of the gel. A tension of 500 to 2,000V is applied between the top and bottom of the gel for 3 to 6 h at room temperature. Once migrated according to the sample target size, system is dismounted, and gel fluorescence is scanned through the use of Typhoon instrument (GE Life Sciences). After image acquisition, ImageJ software (imagej.nih.gov/ij/) is used to analyze the percentage of incorporation of the modified nucleotides.

Figure 2:
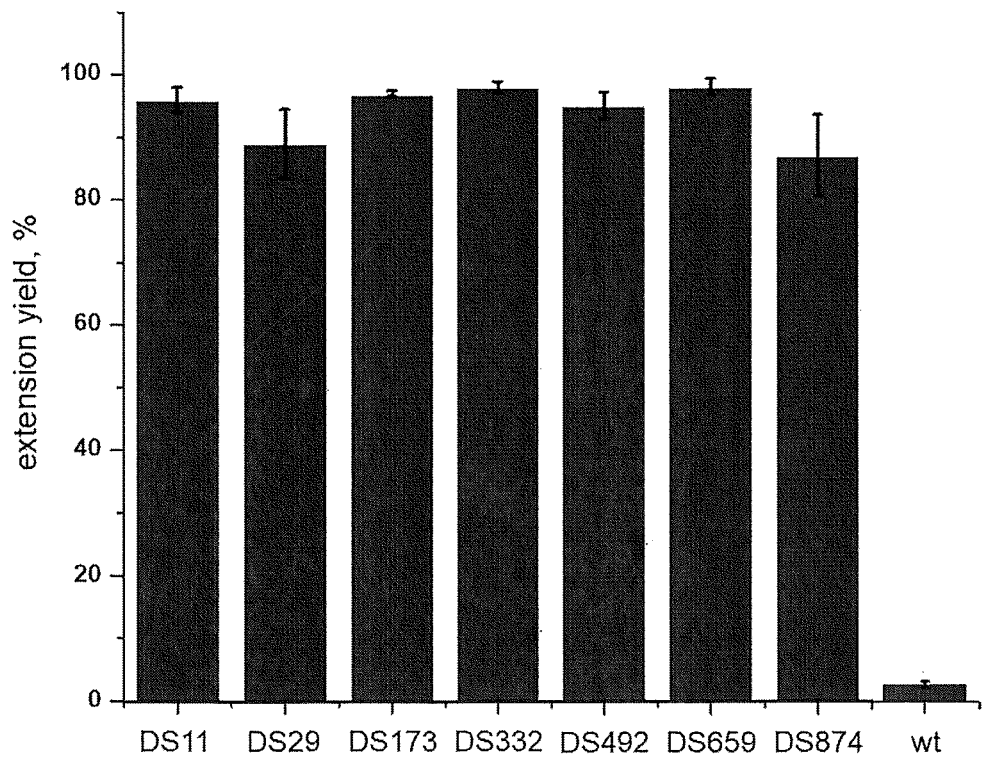
FIG. 2: Comparative results of performances for an elongation assay using wt TdT and TdT variants of the invention. The assay involves fluorescent labeled primers and 3'-O-amino reversible terminator modified nucleotides. The results represent mean value of n=3 experiments for each enzyme.

Results are showed on FIG. 2. For each variant, on the x-axis, the extension percentage has been evaluated as the quantity of expected elongated product over the total quantity of DNA loaded on the gel. Each experiment has been performed in triplicates. The bar height, y-axis, corresponds to the mean value of those three experiments. All the variants according to the invention show more than a 10-fold increase of activity compared to the wt enzyme, confirming the possibility of developing a nucleic acid synthesis technology with these variants.

Example 3—Evaluation of the Activity of Variants of TdT with Unlabeled Primer

Activity Test

Elongation performance of variants of SEQ ID NO: 2: DS928 (R207L+R325P+E328L) and DS950 (R207N+R325A+E328N) generated, expressed and purified according to example 1 was evaluated through the following assay. All the results are compared with a reference variant (SEQ ID N°9) obtained from previous research and to a control tube lacking any polymerase enzyme.

TABLE 8

Activity test

| Reagent | Concentration | Volume |
|---|---|---|
| $H_2O$ | — | 12 µL |
| Activity Buffer | 10x | 2 µL |
| dNTP | 250 µM | 2 µL |
| Purified enzyme | 20 µM | 2 µL |
| Fluorescent primer DNA | 500 nM | 2 µL |

Primer used is the following:

(SEQ ID NO: 8)
5'-TTTTTTTTTTTTAAATAAGG-3'

Nucleotides used (noted as dNTP in table 8) were 3'-O-amino-2',3'-dideoxynucleotides-5'-triphosphate ($ONH_2$, Firebird Biosciences) such as 3'-O-amino-2',3'-dideoxyadenosine-5'-triphosphate for example.

For each variant tested one tube was used for the reaction. The reagents were added in the tube starting from the water and then in the order of Table 8. After 30 min at 37° C. the reaction was stopped by addition of formamide (Sigma).

Analysis

The analysis used liquid chromatography and mass spectrometer detection and quantification (LC/MS). Samples from activity test were analyzed through LC/MS. Samples were loaded into the LC/MS instrument and a standard oligonucleotide separation method was performed. Acquisition of data was followed by deconvolution and spectrum calculation.

Figure 3:
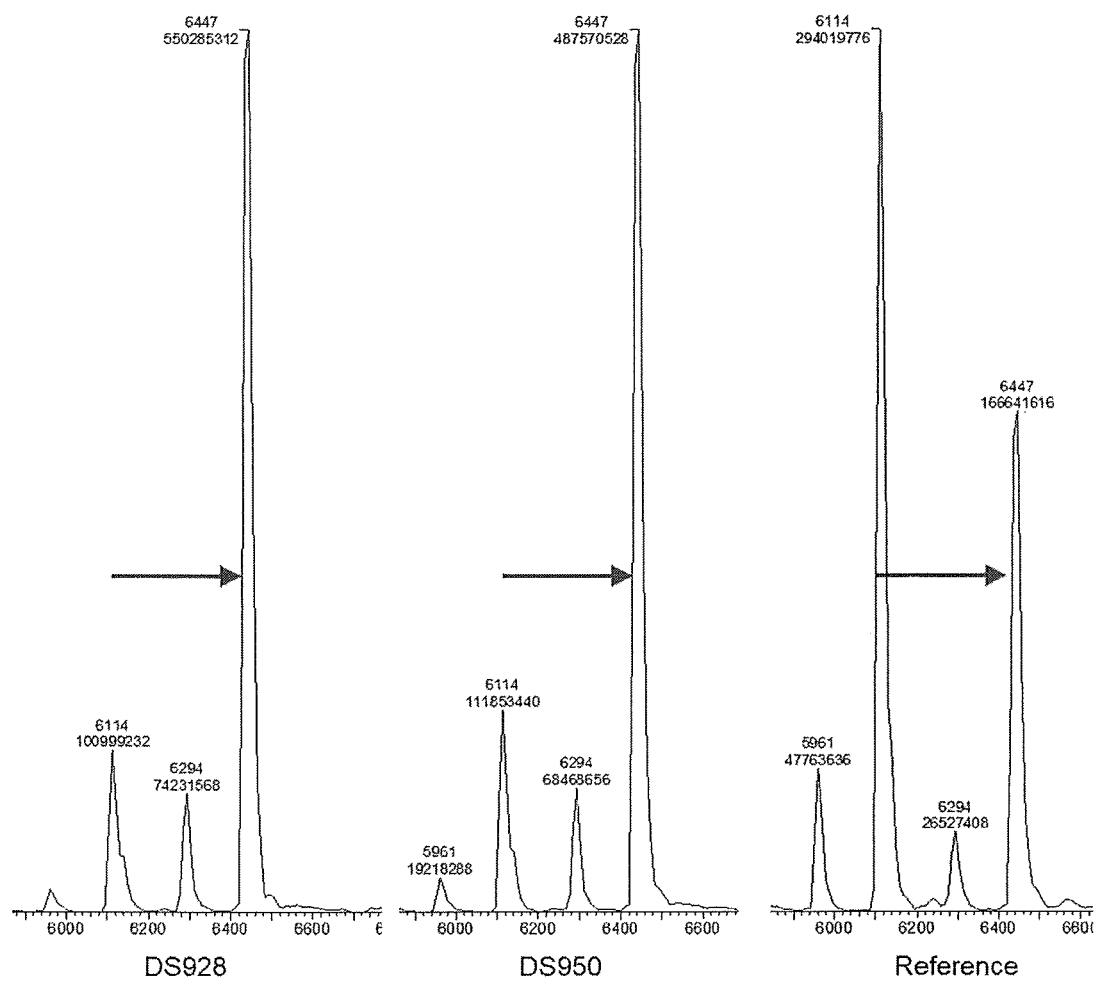
FIG. 3: Mass spectrum analysis of the results obtained for the elongation assay with different TdT variants of the invention. Only the relevant part of the mass spectrum is shown. The arrow shows the peak (mass) for the expected elongated primer.

Results are showed on FIG. 3. The spectrums correspond to the extension analysis of variants DS928, DS950 and references respectively. Initial primer mass is around 6114 and the expected extended product mass is around 6447 (emphasized by the arrows). The intensity of the signal (i.e., the height of the peaks) may be directly correlated to the quantity of material. Both variants DS928, DS950 show significant improvement in the elongation of the starting primer as compared to the reference variant. These results confirm that the new variants according to the invention bring indisputable improvement over the TdT of the prior art.

The invention claimed is:

1. A terminal deoxynucleotidyl transferase (TdT) variant comprising an amino acid sequence at least 90% identical to SEQ ID NO:2, SEQ ID NO:11, SEQ ID NO: 13, SEQ ID NO: 17, SEQ ID NO:19, SEQ ID NO:21, SEQ ID NO:29, or SEQ ID NO:31 with an amino acid substitution of cysteine at position 173, wherein the TdT variant (i) is capable of synthesizing a nucleic acid fragment without a template and (ii) is capable of incorporating a 3'-O-modified nucleotide into the nucleic acid fragment, and wherein the TdT variant incorporates the 3'-O-modified nucleotide at a rate greater than that of a wild type TdT.

2. The TdT variant of claim 1, wherein the 3'-O-modified nucleotide is a 3'-O—$NH_2$-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

3. The TdT variant of claim 1, wherein the modified nucleotide is incorporated onto a free 3'-hydroxyl of a nucleic acid fragment.

4. The TdT variant of claim 1, further comprising a substitution of methionine at position 63 with respect to SEQ ID NO:2, SEQ ID NO:11, SEQ ID NO:13, SEQ ID NO: 17, SEQ ID NO: 19, or SEQ ID NO:29.

5. The TdT variant of claim 1, further comprising a substitution of arginine at position 207 with respect to SEQ ID NO:2, SEQ ID NO:11, SEQ ID NO:13, SEQ ID NO: 17, SEQ ID NO: 19, SEQ ID NO:29 of SEQ ID NO:31.

6. The TdT variant of claim 1, further comprising a substitution of arginine at position 208 with respect to SEQ ID NO:21.

7. The TdT variant of claim 1, further comprising a substitution of arginine at position 324 with respect to SEQ ID NO:11 or SEQ ID NO:13.

8. The TdT variant of claim 1, further comprising a substitution of arginine at position 331 with respect to SEQ ID NO:17.

9. The TdT variant of claim 1, further comprising a substitution of arginine at position 325 with respect to SEQ ID NO:2, SEQ ID NO: 19 or SEQ ID NO:31.

10. The TdT variant of claim 1, further comprising a substitution of arginine at position 328 with respect to SEQ ID NO: 29.

11. The TdT variant of claim 1, further comprising a substitution of glutamic acid at position 327 with respect to SEQ ID NO:11 or SEQ ID NO:13.

12. The TdT variant of claim 1, further comprising a substitution of glutamic acid at position 334 with respect to SEQ ID NO: 17 or SEQ ID NO:21.

13. The TdT variant of claim 1, further comprising a substitution of glutamic acid at position 331 with respect to SEQ ID NO:29.

14. The TdT variant of claim 1, further comprising a substitution of glutamic acid at position 328 with respect to SEQ ID NO:2, SEQ ID NO:19, or SEQ ID NO:31.

15. The TdT variant of claim 1, wherein the substitution of the cysteine is G, R, P, A, V, S, N, Q or D.

16. The TdT variant of claim 4, wherein said substitution of said methionine is R, Q, G, A, V, D, N, H or E.

17. The TdT variant of claim 5, wherein the substitution of the arginine is N, L, K, H, G, D, A or P.

18. The TdT variant of claim 11, wherein the substitution of the glutamic acid is N, L, T or S.

19. The TdT variant of claim 1, wherein the amino acid sequence at least 95% identical to SEQ ID NO:2, SEQ ID NO:11, SEQ ID NO:13, SEQ ID NO:17, SEQ ID NO:19, SEQ ID NO:21, SEQ ID NO:29, or SEQ ID NO:31.

20. The TdT variant of claim 1, wherein the amino acid sequence at least 97% identical to SEQ ID NO:2, SEQ ID NO:11, SEQ ID NO:13, SEQ ID NO:17, SEQ ID NO: 19, SEQ ID NO:21, SEQ ID NO:29, or SEQ ID NO:31.

21. A nucleic acid encoding a TdT variant as defined in claim 1.

22. A method of producing a TdT variant comprising:
(a) culturing a host cell comprising a nucleic acid according to claim 19 under conditions suitable to express the nucleic acid encoding the TdT variant; and optionally
(b) recovering said TdT variant from the cell culture.

* * * * *

SEQUENCE LISTING

<160> NUMBER OF SEQ ID NOS: 35

<210> SEQ ID NO 1
<211> LENGTH: 510

<212> TYPE: PRT
<213> ORGANISM: Mus musculus

<400> SEQUENCE: 1

Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365

Trp Lys Gln Gln Gly Leu Leu Leu Tyr Cys Asp Ile Leu Glu Ser Thr
    370                 375                 380

Phe Glu Lys Phe Lys Gln Pro Ser Arg Lys Val Asp Ala Leu Asp His
385                 390                 395                 400

```
Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
            420                 425                 430

Val Asp Leu Val Met Cys Pro Tyr Asp Arg Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Ile Phe Ala
                485                 490                 495

His Leu Gly Leu Asp Tyr Ile Glu Pro Trp Glu Arg Asn Ala
            500                 505                 510

<210> SEQ ID NO 2
<211> LENGTH: 381
<212> TYPE: PRT
<213> ORGANISM: Mus musculus

<400> SEQUENCE: 2

Asn Ser Ser Pro Ser Pro Val Pro Gly Ser Gln Asn Val Pro Ala Pro
1               5                   10                  15

Ala Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
        35                  40                  45

Asn Asp Glu Leu Arg Glu Asn Glu Gly Ser Cys Leu Ala Phe Met Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Ala Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Cys Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Arg Gly
        195                 200                 205

Lys Met Thr Gly His Asp Val Asp Phe Leu Ile Thr Ser Pro Glu Ala
    210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
```

```
                   260               265               270
Gln Lys Cys Phe Leu Ile Leu Lys Leu Asp His Gly Arg Val His Ser
            275                 280                 285
Glu Lys Ser Gly Gln Gln Glu Gly Lys Gly Trp Lys Ala Ile Arg Val
            290                 295                 300
Asp Leu Val Met Cys Pro Tyr Asp Arg Arg Ala Phe Ala Leu Leu Gly
305                 310                 315                 320
Trp Thr Gly Ser Arg Gln Phe Glu Arg Asp Leu Arg Arg Tyr Ala Thr
                325                 330                 335
His Glu Arg Lys Met Met Leu Asp Asn His Ala Leu Tyr Asp Arg Thr
                340                 345                 350
Lys Arg Val Phe Leu Glu Ala Glu Ser Glu Glu Ile Phe Ala His
                355                 360                 365
Leu Gly Leu Asp Tyr Ile Glu Pro Trp Glu Arg Asn Ala
                370                 375                 380

<210> SEQ ID NO 3
<211> LENGTH: 494
<212> TYPE: PRT
<213> ORGANISM: Homo sapiens

<400> SEQUENCE: 3

Met Leu Pro Lys Arg Arg Arg Ala Arg Val Gly Ser Pro Ser Gly Asp
1               5                  10                  15
Ala Ala Ser Ser Thr Pro Pro Ser Thr Arg Phe Pro Gly Val Ala Ile
                20                  25                  30
Tyr Leu Val Glu Pro Arg Met Gly Arg Ser Arg Arg Ala Phe Leu Thr
            35                  40                  45
Gly Leu Ala Arg Ser Lys Gly Phe Arg Val Leu Asp Ala Cys Ser Ser
        50                  55                  60
Glu Ala Thr His Val Val Met Glu Gly Thr Ser Ala Glu Glu Ala Val
65                  70                  75                  80
Ser Trp Gln Glu Arg Arg Met Ala Ala Pro Pro Gly Cys Thr Pro
                85                  90                  95
Pro Ala Leu Leu Asp Ile Ser Trp Leu Thr Glu Ser Leu Gly Ala Gly
                100                 105                 110
Gln Pro Val Pro Val Glu Cys Arg His Arg Leu Glu Val Ala Gly Pro
            115                 120                 125
Arg Lys Gly Pro Leu Ser Pro Ala Trp Met Pro Ala Tyr Ala Cys Gln
        130                 135                 140
Arg Pro Thr Pro Leu Thr His His Asn Thr Gly Leu Ser Glu Ala Leu
145                 150                 155                 160
Glu Ile Leu Ala Glu Ala Ala Gly Phe Glu Gly Ser Glu Gly Arg Leu
                165                 170                 175
Leu Thr Phe Cys Arg Ala Ala Ser Val Leu Lys Ala Leu Pro Ser Pro
                180                 185                 190
Val Thr Thr Leu Ser Gln Leu Gln Gly Leu Pro His Phe Gly Glu His
            195                 200                 205
Ser Ser Arg Val Val Gln Glu Leu Leu Glu His Gly Val Cys Glu Glu
        210                 215                 220
Val Glu Arg Val Arg Arg Ser Glu Arg Tyr Gln Thr Met Lys Leu Phe
225                 230                 235                 240
Thr Gln Ile Phe Gly Val Gly Val Lys Thr Ala Asp Arg Trp Tyr Arg
                245                 250                 255
```

Glu Gly Leu Arg Thr Leu Asp Asp Leu Arg Glu Gln Pro Gln Lys Leu
                260                 265                 270

Thr Gln Gln Gln Lys Ala Gly Leu Gln His His Gln Asp Leu Ser Thr
            275                 280                 285

Pro Val Leu Arg Ser Asp Val Asp Ala Leu Gln Gln Val Val Glu Glu
        290                 295                 300

Ala Val Gly Gln Ala Leu Pro Gly Ala Thr Val Thr Leu Thr Gly Gly
305                 310                 315                 320

Phe Arg Arg Gly Lys Leu Gln Gly His Asp Val Asp Phe Leu Ile Thr
                325                 330                 335

His Pro Lys Glu Gly Gln Glu Ala Gly Leu Leu Pro Arg Val Met Cys
            340                 345                 350

Arg Leu Gln Asp Gln Gly Leu Ile Leu Tyr His Gln His Gln His Ser
        355                 360                 365

Cys Cys Glu Ser Pro Thr Arg Leu Ala Gln Gln Ser His Met Asp Ala
    370                 375                 380

Phe Glu Arg Ser Phe Cys Ile Phe Arg Leu Pro Gln Pro Pro Gly Ala
385                 390                 395                 400

Ala Val Gly Gly Ser Thr Arg Pro Cys Pro Ser Trp Lys Ala Val Arg
                405                 410                 415

Val Asp Leu Val Val Ala Pro Val Ser Gln Phe Pro Phe Ala Leu Leu
            420                 425                 430

Gly Trp Thr Gly Ser Lys Leu Phe Gln Arg Glu Leu Arg Arg Phe Ser
        435                 440                 445

Arg Lys Glu Lys Gly Leu Trp Leu Asn Ser His Gly Leu Phe Asp Pro
    450                 455                 460

Glu Gln Lys Thr Phe Phe Gln Ala Ala Ser Glu Glu Asp Ile Phe Arg
465                 470                 475                 480

His Leu Gly Leu Glu Tyr Leu Pro Pro Glu Gln Arg Asn Ala
                485                 490

<210> SEQ ID NO 4
<211> LENGTH: 401
<212> TYPE: PRT
<213> ORGANISM: Homo sapiens

<400> SEQUENCE: 4

Thr Met Gly Ser Ser His His His His His His Ser Ser Gly Leu Val
1               5                   10                  15

Pro Arg Gly Ser His Met Ser Pro Ser Pro Val Pro Gly Ser Gln Asn
            20                  25                  30

Val Pro Ala Pro Ala Val Lys Lys Ile Ser Gln Tyr Ala Cys Gln Arg
        35                  40                  45

Arg Thr Thr Leu Asn Asn Tyr Asn Gln Leu Phe Thr Asp Ala Leu Asp
    50                  55                  60

Ile Leu Ala Glu Asn Asp Glu Leu Arg Glu Asn Glu Gly Ser Cys Leu
65                  70                  75                  80

Ala Phe Met Arg Ala Ser Ser Val Leu Lys Ser Leu Pro Phe Pro Ile
                85                  90                  95

Thr Ser Met Lys Asp Thr Glu Gly Ile Pro Cys Leu Gly Asp Lys Val
            100                 105                 110

Lys Ser Ile Ile Glu Gly Ile Ile Glu Asp Gly Glu Ser Ser Glu Ala
        115                 120                 125

Lys Ala Val Leu Asn Asp Glu Arg Tyr Lys Ser Phe Lys Leu Phe Thr
    130                 135                 140

```
Ser Val Phe Gly Val Gly Leu Lys Thr Ala Glu Lys Trp Phe Arg Met
145                 150                 155                 160

Gly Phe Arg Thr Leu Ser Lys Ile Gln Ser Asp Lys Ser Leu Arg Phe
                165                 170                 175

Thr Gln Met Gln Lys Ala Gly Phe Leu Tyr Tyr Glu Asp Leu Val Ser
            180                 185                 190

Cys Val Asn Arg Pro Glu Ala Glu Ala Val Ser Met Leu Val Lys Glu
        195                 200                 205

Ala Val Val Thr Phe Leu Pro Asp Ala Leu Val Thr Met Thr Gly Gly
    210                 215                 220

Phe Arg Arg Gly Lys Met Thr Gly His Asp Val Asp Phe Leu Ile Thr
225                 230                 235                 240

Ser Pro Glu Ala Thr Glu Asp Glu Glu Gln Gln Leu Leu His Lys Val
                245                 250                 255

Thr Asp Phe Trp Lys Gln Gln Gly Leu Leu Leu Tyr Cys Asp Ile Leu
                260                 265                 270

Glu Ser Thr Phe Glu Lys Phe Lys Gln Pro Ser Arg Lys Val Asp Ala
            275                 280                 285

Leu Asp His Phe Gln Lys Cys Phe Leu Ile Leu Lys Leu Asp His Gly
        290                 295                 300

Arg Val His Ser Glu Lys Ser Gly Gln Gln Glu Gly Lys Gly Trp Lys
305                 310                 315                 320

Ala Ile Arg Val Asp Leu Val Met Cys Pro Tyr Asp Arg Arg Ala Phe
                325                 330                 335

Ala Leu Leu Gly Trp Thr Gly Ser Arg Gln Phe Glu Arg Asp Leu Arg
                340                 345                 350

Arg Tyr Ala Thr His Glu Arg Lys Met Met Leu Asp Asn His Ala Leu
            355                 360                 365

Tyr Asp Arg Thr Lys Arg Val Phe Leu Glu Ala Glu Ser Glu Glu Glu
        370                 375                 380

Ile Phe Ala His Leu Gly Leu Asp Tyr Ile Glu Pro Trp Glu Arg Asn
385                 390                 395                 400

Ala

<210> SEQ ID NO 5
<211> LENGTH: 20
<212> TYPE: DNA
<213> ORGANISM: Artificial Sequence
<220> FEATURE:
<223> OTHER INFORMATION: t7-pro primer

<400> SEQUENCE: 5
taatacgact cactataggg                                              20

<210> SEQ ID NO 6
<211> LENGTH: 19
<212> TYPE: DNA
<213> ORGANISM: Artificial Sequence
<220> FEATURE:
<223> OTHER INFORMATION: T7-ter primer

<400> SEQUENCE: 6
gctagttatt gctcagcgg                                               19

<210> SEQ ID NO 7
<211> LENGTH: 18
<212> TYPE: DNA
```

<213> ORGANISM: Artificial Sequence
<220> FEATURE:
<223> OTHER INFORMATION: primer

<400> SEQUENCE: 7
aaaaaaaaaa aaaagggg                                                    18

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tttttttttt ttaaataagg                                                  20

<210> SEQ ID NO 9
<211> LENGTH: 401
<212> TYPE: PRT
<213> ORGANISM: Artificial Sequence
<220> FEATURE:
<223> OTHER INFORMATION: Reference TdT variant

<400> SEQUENCE: 9

Thr Met Gly Ser Ser His His His His His Ser Ser Gly Leu Val
1               5                   10                  15

Pro Arg Gly Ser His Met Ser Pro Ser Pro Val Pro Gly Ser Gln Asn
            20                  25                  30

Val Pro Ala Pro Ala Val Lys Lys Ile Ser Gln Tyr Ala Cys Gln Arg
        35                  40                  45

Arg Thr Thr Leu Asn Asn Tyr Asn Gln Leu Phe Thr Asp Ala Leu Asp
    50                  55                  60

Ile Leu Ala Glu Asn Asp Glu Leu Arg Glu Asn Glu Gly Ser Cys Leu
65                  70                  75                  80

Ala Phe Met Arg Ala Ser Ser Val Leu Lys Ser Leu Pro Phe Pro Ile
                85                  90                  95

Thr Ser Met Lys Asp Thr Glu Gly Ile Pro Cys Leu Gly Asp Lys Val
            100                 105                 110

Lys Ser Ile Ile Glu Gly Ile Ile Glu Asp Gly Glu Ser Ser Glu Ala
        115                 120                 125

Lys Ala Val Leu Asn Asp Glu Arg Tyr Lys Ser Phe Lys Leu Phe Thr
    130                 135                 140

Ser Val Phe Gly Val Gly Leu Lys Thr Ala Glu Lys Trp Phe Arg Met
145                 150                 155                 160

Gly Phe Arg Thr Leu Ser Lys Ile Gln Ser Asp Lys Ser Leu Arg Phe
                165                 170                 175

Thr Gln Met Gln Lys Ala Gly Phe Leu Tyr Tyr Glu Asp Leu Val Ser
            180                 185                 190

Cys Val Asn Arg Pro Glu Ala Glu Ala Val Ser Met Leu Val Lys Glu
        195                 200                 205

Ala Val Val Thr Phe Leu Pro Asp Ala Leu Val Thr Met Thr Gly Gly
    210                 215                 220

Phe Arg Arg Gly Lys Met Thr Gly His Asp Val Asp Phe Leu Ile Thr
225                 230                 235                 240

Ser Pro Glu Ala Thr Glu Asp Glu Glu Gln Gln Leu Leu His Lys Val
                245                 250                 255

Thr Asp Phe Trp Lys Gln Gln Gly Leu Leu Leu Tyr Cys Asp Ile Leu

```
                   260                 265                 270
Glu Ser Thr Phe Glu Lys Phe Lys Gln Pro Ser Arg Lys Val Asp Ala
            275                 280                 285

Leu Asp His Phe Gln Lys Cys Phe Leu Ile Leu Lys Leu Asp His Gly
        290                 295                 300

Arg Val His Ser Glu Lys Ser Gly Gln Gln Glu Lys Gly Trp Lys
305                 310                 315                 320

Ala Ile Arg Val Asp Leu Val Met Cys Pro Tyr Asp Arg Arg Ala Phe
                325                 330                 335

Ala Leu Leu Gly Trp Thr Gly Ser Ala Gln Phe Ser Arg Asp Leu Arg
            340                 345                 350

Arg Tyr Ala Thr His Glu Arg Lys Met Met Leu Asp Asn His Ala Leu
        355                 360                 365

Tyr Asp Arg Thr Lys Arg Val Phe Leu Glu Ala Glu Ser Glu Glu
    370                 375                 380

Ile Phe Ala His Leu Gly Leu Asp Tyr Ile Glu Pro Trp Glu Arg Asn
385                 390                 395                 400

Ala

<210> SEQ ID NO 10
<211> LENGTH: 519
<212> TYPE: PRT
<213> ORGANISM: Bos taurus

<400> SEQUENCE: 10

Met Ala Gln Gln Arg Gln His Gln Arg Leu Pro Met Asp Pro Leu Cys
1               5                   10                  15

Thr Ala Ser Ser Gly Pro Arg Lys Lys Arg Pro Arg Gln Val Gly Ala
            20                  25                  30

Ser Met Ala Ser Pro Pro His Asp Ile Lys Phe Gln Asn Leu Val Leu
        35                  40                  45

Phe Ile Leu Glu Lys Lys Met Gly Thr Thr Arg Arg Asn Phe Leu Met
    50                  55                  60

Glu Leu Ala Arg Arg Lys Gly Phe Arg Val Glu Asn Glu Leu Ser Asp
65                  70                  75                  80

Ser Val Thr His Ile Val Ala Glu Asn Asn Ser Gly Ser Glu Val Leu
                85                  90                  95

Glu Trp Leu Gln Val Gln Asn Ile Arg Ala Ser Ser Gln Leu Glu Leu
            100                 105                 110

Leu Asp Val Ser Trp Leu Ile Glu Ser Met Gly Ala Gly Lys Pro Val
        115                 120                 125

Glu Ile Thr Gly Lys His Gln Leu Val Val Arg Thr Asp Tyr Ser Ala
    130                 135                 140

Thr Pro Asn Pro Gly Phe Gln Lys Thr Pro Pro Leu Ala Val Lys Lys
145                 150                 155                 160

Ile Ser Gln Tyr Ala Cys Gln Arg Lys Thr Thr Leu Asn Asn Tyr Asn
                165                 170                 175

His Ile Phe Thr Asp Ala Phe Glu Ile Leu Ala Glu Asn Ser Glu Phe
            180                 185                 190

Lys Glu Asn Glu Val Ser Tyr Val Thr Phe Met Arg Ala Ala Ser Val
        195                 200                 205

Leu Lys Ser Leu Pro Phe Thr Ile Ile Ser Met Lys Asp Thr Glu Gly
    210                 215                 220

Ile Pro Cys Leu Gly Asp Lys Val Lys Cys Ile Ile Glu Glu Ile Ile
```

```
                225                 230                 235                 240
  Glu Asp Gly Glu Ser Ser Glu Val Lys Ala Val Leu Asn Asp Glu Arg
                  245                 250                 255

Tyr Gln Ser Phe Lys Leu Phe Thr Ser Val Phe Gly Val Gly Leu Lys
                  260                 265                 270

Thr Ser Glu Lys Trp Phe Arg Met Gly Phe Arg Ser Leu Ser Lys Ile
                  275                 280                 285

Met Ser Asp Lys Thr Leu Lys Phe Thr Lys Met Gln Lys Ala Gly Phe
                  290                 295                 300

Leu Tyr Tyr Glu Asp Leu Val Ser Cys Val Thr Arg Ala Glu Ala Glu
  305                 310                 315                 320

Ala Val Gly Val Leu Val Lys Glu Ala Val Trp Ala Phe Leu Pro Asp
                  325                 330                 335

Ala Phe Val Thr Met Thr Gly Gly Phe Arg Arg Gly Lys Lys Ile Gly
                  340                 345                 350

His Asp Val Asp Phe Leu Ile Thr Ser Pro Gly Ser Ala Glu Asp Glu
                  355                 360                 365

Glu Gln Leu Leu Pro Lys Val Ile Asn Leu Trp Glu Lys Lys Gly Leu
                  370                 375                 380

Leu Leu Tyr Tyr Asp Leu Val Glu Ser Thr Phe Glu Lys Phe Lys Leu
  385                 390                 395                 400

Pro Ser Arg Gln Val Asp Thr Leu Asp His Phe Gln Lys Cys Phe Leu
                  405                 410                 415

Ile Leu Lys Leu His His Gln Arg Val Asp Ser Ser Lys Ser Asn Gln
                  420                 425                 430

Gln Glu Gly Lys Thr Trp Lys Ala Ile Arg Val Asp Leu Val Met Cys
                  435                 440                 445

Pro Tyr Glu Asn Arg Ala Phe Ala Leu Leu Gly Trp Thr Gly Ser Arg
                  450                 455                 460

Gln Phe Glu Arg Asp Ile Arg Arg Tyr Ala Thr His Glu Arg Lys Met
  465                 470                 475                 480

Met Leu Asp Asn His Ala Leu Tyr Asp Lys Thr Lys Arg Val Phe Leu
                  485                 490                 495

Lys Ala Glu Ser Glu Glu Ile Phe Ala His Leu Gly Leu Asp Tyr
                  500                 505                 510

Ile Glu Pro Trp Glu Arg Asn
            515

<210> SEQ ID NO 11
<211> LENGTH: 380
<212> TYPE: PRT
<213> ORGANISM: Bos taurus

<400> SEQUENCE: 11

Asp Tyr Ser Ala Thr Pro Asn Pro Gly Phe Gln Lys Thr Pro Pro Leu
  1               5                  10                  15

Ala Val Lys Lys Ile Ser Gln Tyr Ala Cys Gln Arg Lys Thr Thr Leu
                  20                  25                  30

Asn Asn Tyr Asn His Ile Phe Thr Asp Ala Phe Glu Ile Leu Ala Glu
              35                  40                  45

Asn Ser Glu Phe Lys Glu Asn Glu Val Ser Tyr Val Thr Phe Met Arg
          50                  55                  60

Ala Ala Ser Val Leu Lys Ser Leu Pro Phe Thr Ile Ile Ser Met Lys
  65                  70                  75                  80
```

```
Asp Thr Glu Gly Ile Pro Cys Leu Gly Asp Lys Val Lys Cys Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
            115                 120                 125

Val Gly Leu Lys Thr Ser Glu Lys Trp Phe Arg Met Gly Phe Arg Ser
130                 135                 140

Leu Ser Lys Ile Met Ser Asp Lys Thr Leu Lys Phe Thr Lys Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Trp Ala
            180                 185                 190

Phe Leu Pro Asp Ala Phe Val Thr Met Thr Gly Gly Phe Arg Arg Gly
            195                 200                 205

Lys Lys Ile Gly His Asp Val Asp Phe Leu Ile Thr Ser Pro Gly Ser
            210                 215                 220

Ala Glu Asp Glu Glu Gln Leu Leu Pro Lys Val Ile Asn Leu Trp Glu
225                 230                 235                 240

Lys Lys Gly Leu Leu Leu Tyr Tyr Asp Leu Val Glu Ser Thr Phe Glu
                245                 250                 255

Lys Phe Lys Leu Pro Ser Arg Gln Val Asp Thr Leu Asp His Phe Gln
            260                 265                 270

Lys Cys Phe Leu Ile Leu Lys Leu His His Gln Arg Val Asp Ser Ser
            275                 280                 285

Lys Ser Asn Gln Gln Glu Gly Lys Thr Trp Lys Ala Ile Arg Val Asp
290                 295                 300

Leu Val Met Cys Pro Tyr Glu Asn Arg Ala Phe Ala Leu Leu Gly Trp
305                 310                 315                 320

Thr Gly Ser Arg Gln Phe Glu Arg Asp Ile Arg Arg Tyr Ala Thr His
                325                 330                 335

Glu Arg Lys Met Met Leu Asp Asn His Ala Leu Tyr Asp Lys Thr Lys
            340                 345                 350

Arg Val Phe Leu Lys Ala Glu Ser Glu Glu Glu Ile Phe Ala His Leu
            355                 360                 365

Gly Leu Asp Tyr Ile Glu Pro Trp Glu Arg Asn Ala
            370                 375                 380

<210> SEQ ID NO 12
<211> LENGTH: 509
<212> TYPE: PRT
<213> ORGANISM: Homo sapiens

<400> SEQUENCE: 12

Met Asp Pro Pro Arg Ala Ser His Leu Ser Pro Arg Lys Lys Arg Pro
1               5                   10                  15

Arg Gln Thr Gly Ala Leu Met Ala Ser Ser Pro Gln Asp Ile Lys Phe
            20                  25                  30

Gln Asp Leu Val Val Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80
```

```
Gly Ser Asp Val Leu Glu Trp Leu Gln Ala Gln Lys Val Gln Val Ser
                85                  90                  95

Ser Gln Pro Glu Leu Leu Asp Val Ser Trp Leu Ile Glu Cys Ile Arg
            100                 105                 110

Ala Gly Lys Pro Val Glu Met Thr Gly Lys His Gln Leu Val Val Arg
        115                 120                 125

Arg Asp Tyr Ser Asp Ser Thr Asn Pro Gly Pro Lys Thr Pro Pro
130                 135                 140

Ile Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Val Lys Gly Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Val Arg Ser Asp Lys Ser Leu Lys Phe Thr Arg Met
        275                 280                 285

Gln Lys Ala Gly Phe Leu Tyr Tyr Glu Asp Leu Val Ser Cys Val Thr
290                 295                 300

Arg Ala Glu Ala Glu Ala Val Ser Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Glu Asp Glu Glu Gln Leu Leu Gln Lys Val Met Asn Leu Trp
        355                 360                 365

Glu Lys Lys Gly Leu Leu Leu Tyr Tyr Asp Leu Val Glu Ser Thr Phe
370                 375                 380

Glu Lys Leu Arg Leu Pro Ser Arg Lys Val Asp Ala Leu Asp His Phe
385                 390                 395                 400

Gln Lys Cys Phe Leu Ile Phe Lys Leu Pro Arg Gln Arg Val Asp Ser
                405                 410                 415

Asp Gln Ser Ser Trp Gln Glu Gly Lys Thr Trp Lys Ala Ile Arg Val
            420                 425                 430

Asp Leu Val Leu Cys Pro Tyr Glu Arg Arg Ala Phe Ala Leu Leu Gly
        435                 440                 445

Trp Thr Gly Ser Arg Gln Phe Glu Arg Asp Leu Arg Arg Tyr Ala Thr
450                 455                 460

His Glu Arg Lys Met Ile Leu Asp Asn His Ala Leu Tyr Asp Lys Thr
465                 470                 475                 480

Lys Arg Ile Phe Leu Lys Ala Glu Ser Glu Glu Glu Ile Phe Ala His
                485                 490                 495
```

```
Leu Gly Leu Asp Tyr Ile Glu Pro Trp Glu Arg Asn Ala
            500                 505

<210> SEQ ID NO 13
<211> LENGTH: 380
<212> TYPE: PRT
<213> ORGANISM: Homo sapiens

<400> SEQUENCE: 13

Asp Tyr Ser Asp Ser Thr Asn Pro Gly Pro Lys Thr Pro Pro Ile
1               5                   10                  15

Ala Val Gln Lys Ile Ser Gln Tyr Ala Cys Gln Arg Arg Thr Thr Leu
                20                  25                  30

Asn Asn Cys Asn Gln Ile Phe Thr Asp Ala Phe Asp Ile Leu Ala Glu
            35                  40                  45

Asn Cys Glu Phe Arg Glu Asn Glu Asp Ser Cys Val Thr Phe Met Arg
50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Ser Lys Val Lys Gly Ile Ile
                85                  90                  95

Glu Glu Ile Ile Glu Asp Gly Glu Ser Ser Glu Val Lys Ala Val Leu
                100                 105                 110

Asn Asp Glu Arg Tyr Gln Ser Phe Lys Leu Phe Thr Ser Val Phe Gly
            115                 120                 125

Val Gly Leu Lys Thr Ser Glu Lys Trp Phe Arg Met Gly Phe Arg Thr
130                 135                 140

Leu Ser Lys Val Arg Ser Asp Lys Ser Leu Lys Phe Thr Arg Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Ser Val Leu Val Lys Glu Ala Val Trp Ala
            180                 185                 190

Phe Leu Pro Asp Ala Phe Val Thr Met Thr Gly Gly Phe Arg Arg Gly
            195                 200                 205

Lys Lys Met Gly His Asp Val Asp Phe Leu Ile Thr Ser Pro Gly Ser
210                 215                 220

Thr Glu Asp Glu Glu Gln Leu Leu Gln Lys Val Met Asn Leu Trp Glu
225                 230                 235                 240

Lys Lys Gly Leu Leu Leu Tyr Tyr Asp Leu Val Glu Ser Thr Phe Glu
                245                 250                 255

Lys Leu Arg Leu Pro Ser Arg Lys Val Asp Ala Leu Asp His Phe Gln
            260                 265                 270

Lys Cys Phe Leu Ile Phe Lys Leu Pro Arg Gln Arg Val Asp Ser Asp
            275                 280                 285

Gln Ser Ser Trp Gln Glu Gly Lys Thr Trp Lys Ala Ile Arg Val Asp
            290                 295                 300

Leu Val Leu Cys Pro Tyr Glu Arg Arg Ala Phe Ala Leu Leu Gly Trp
305                 310                 315                 320

Thr Gly Ser Arg Gln Phe Glu Arg Asp Leu Arg Arg Tyr Ala Thr His
                325                 330                 335

Glu Arg Lys Met Ile Leu Asp Asn His Ala Leu Tyr Asp Lys Thr Lys
                340                 345                 350

Arg Ile Phe Leu Lys Ala Glu Ser Glu Glu Ile Phe Ala His Leu
                355                 360                 365
```

```
Gly Leu Asp Tyr Ile Glu Pro Trp Glu Arg Asn Ala
    370             375             380
```

<210> SEQ ID NO 14
<211> LENGTH: 506
<212> TYPE: PRT
<213> ORGANISM: Gallus gallus
<400> SEQUENCE: 14

```
Met Glu Arg Ile Arg Pro Pro Thr Val Val Ser Gln Arg Lys Arg Gln
1               5                   10                  15

Lys Gly Met Tyr Ser Pro Lys Leu Ser Cys Gly Tyr Glu Ile Lys Phe
            20                  25                  30

Asn Lys Leu Val Ile Phe Ile Met Gln Arg Lys Met Gly Met Thr Arg
                35                  40                  45

Arg Thr Phe Leu Met Glu Leu Ala Arg Ser Lys Gly Phe Arg Val Glu
        50                  55                  60

Ser Glu Leu Ser Asp Ser Val Thr His Ile Val Ala Glu Asn Asn Ser
65                  70                  75                  80

Tyr Pro Glu Val Leu Asp Trp Leu Lys Gly Gln Ala Val Gly Asp Ser
                85                  90                  95

Ser Arg Phe Glu Ile Leu Asp Ile Ser Trp Leu Thr Ala Cys Met Glu
            100                 105                 110

Met Gly Arg Pro Val Asp Leu Glu Lys Lys Tyr His Leu Val Glu Gln
        115                 120                 125

Ala Gly Gln Tyr Pro Thr Leu Lys Thr Pro Glu Ser Glu Val Ser Ser
    130                 135                 140

Phe Thr Ala Ser Lys Val Ser Gln Tyr Ser Cys Gln Arg Lys Thr Thr
145                 150                 155                 160

Leu Asn Asn Cys Asn Lys Lys Phe Thr Asp Ala Phe Glu Ile Met Ala
                165                 170                 175

Glu Asn Tyr Glu Phe Lys Glu Asn Glu Ile Phe Cys Leu Glu Phe Leu
            180                 185                 190

Arg Ala Ala Ser Val Leu Lys Ser Leu Pro Phe Pro Val Thr Arg Met
        195                 200                 205

Lys Asp Ile Gln Gly Leu Pro Cys Met Gly Asp Arg Val Arg Asp Val
    210                 215                 220

Ile Glu Glu Ile Ile Glu Gly Glu Ser Ser Arg Ala Lys Asp Val
225                 230                 235                 240

Leu Asn Asp Glu Arg Tyr Lys Ser Phe Lys Glu Phe Thr Ser Val Phe
                245                 250                 255

Gly Val Gly Val Lys Thr Ser Glu Lys Trp Phe Arg Met Gly Leu Arg
            260                 265                 270

Thr Val Glu Glu Val Lys Ala Asp Lys Thr Leu Lys Leu Ser Lys Met
        275                 280                 285

Gln Arg Ala Gly Phe Leu Tyr Tyr Glu Asp Leu Val Ser Cys Val Ser
    290                 295                 300

Lys Ala Glu Ala Asp Ala Val Ser Ser Ile Val Lys Asn Thr Val Cys
305                 310                 315                 320

Thr Phe Leu Pro Asp Ala Leu Val Thr Ile Thr Gly Gly Phe Arg Arg
                325                 330                 335

Gly Lys Lys Ile Gly His Asp Ile Asp Phe Leu Ile Thr Ser Pro Gly
            340                 345                 350

Gln Arg Glu Asp Asp Glu Leu Leu His Lys Gly Leu Leu Leu Tyr Cys
```

```
                355                 360                 365
Asp Ile Ile Glu Ser Thr Phe Val Lys Glu Gln Ile Pro Ser Arg His
    370                 375                 380

Val Asp Ala Met Asp His Phe Gln Lys Cys Phe Ala Ile Leu Lys Leu
385                 390                 395                 400

Tyr Gln Pro Arg Val Asp Asn Ser Ser Tyr Asn Met Ser Lys Lys Cys
                405                 410                 415

Asp Met Ala Glu Val Lys Asp Trp Lys Ala Ile Arg Val Asp Leu Val
            420                 425                 430

Ile Thr Pro Phe Glu Gln Tyr Ala Tyr Ala Leu Leu Gly Trp Thr Gly
            435                 440                 445

Ser Arg Gln Phe Gly Arg Asp Leu Arg Arg Tyr Ala Thr His Glu Arg
        450                 455                 460

Lys Met Met Leu Asp Asn His Ala Leu Tyr Asp Lys Arg Lys Arg Val
465                 470                 475                 480

Phe Leu Lys Ala Gly Ser Glu Glu Ile Phe Ala His Leu Gly Leu
                485                 490                 495

Asp Tyr Val Glu Pro Trp Glu Arg Asn Ala
            500                 505

<210> SEQ ID NO 15
<211> LENGTH: 376
<212> TYPE: PRT
<213> ORGANISM: Gallus gallus

<400> SEQUENCE: 15

Gln Tyr Pro Thr Leu Lys Thr Pro Glu Ser Glu Val Ser Ser Phe Thr
1               5                   10                  15

Ala Ser Lys Val Ser Gln Tyr Ser Cys Gln Arg Lys Thr Thr Leu Asn
                20                  25                  30

Asn Cys Asn Lys Lys Phe Thr Asp Ala Phe Glu Ile Met Ala Glu Asn
            35                  40                  45

Tyr Glu Phe Lys Glu Asn Glu Ile Phe Cys Leu Glu Phe Leu Arg Ala
    50                  55                  60

Ala Ser Val Leu Lys Ser Leu Pro Phe Pro Val Thr Arg Met Lys Asp
65                  70                  75                  80

Ile Gln Gly Leu Pro Cys Met Gly Asp Arg Val Arg Asp Val Ile Glu
                85                  90                  95

Glu Ile Ile Glu Glu Gly Glu Ser Ser Arg Ala Lys Asp Val Leu Asn
            100                 105                 110

Asp Glu Arg Tyr Lys Ser Phe Lys Glu Phe Thr Ser Val Phe Gly Val
        115                 120                 125

Gly Val Lys Thr Ser Glu Lys Trp Phe Arg Met Gly Leu Arg Thr Val
130                 135                 140

Glu Glu Val Lys Ala Asp Lys Thr Leu Lys Leu Ser Lys Met Gln Arg
145                 150                 155                 160

Ala Gly Phe Leu Tyr Tyr Glu Asp Leu Val Ser Cys Val Ser Lys Ala
                165                 170                 175

Glu Ala Asp Ala Val Ser Ser Ile Val Lys Asn Thr Val Cys Thr Phe
            180                 185                 190

Leu Pro Asp Ala Leu Val Thr Ile Thr Gly Gly Phe Arg Arg Gly Lys
        195                 200                 205

Lys Ile Gly His Asp Ile Asp Phe Leu Ile Thr Ser Pro Gly Gln Arg
    210                 215                 220
```

-continued

Glu Asp Asp Glu Leu Leu His Lys Gly Leu Leu Tyr Cys Asp Ile
225                 230                 235                 240

Ile Glu Ser Thr Phe Val Lys Glu Gln Ile Pro Ser Arg His Val Asp
            245                 250                 255

Ala Met Asp His Phe Gln Lys Cys Phe Ala Ile Leu Lys Leu Tyr Gln
        260                 265                 270

Pro Arg Val Asp Asn Ser Ser Tyr Asn Met Ser Lys Lys Cys Asp Met
    275                 280                 285

Ala Glu Val Lys Asp Trp Lys Ala Ile Arg Val Asp Leu Val Ile Thr
290                 295                 300

Pro Phe Glu Gln Tyr Ala Tyr Ala Leu Leu Gly Trp Thr Gly Ser Arg
305                 310                 315                 320

Gln Phe Gly Arg Asp Leu Arg Arg Tyr Ala Thr His Glu Arg Lys Met
            325                 330                 335

Met Leu Asp Asn His Ala Leu Tyr Asp Lys Arg Lys Arg Val Phe Leu
        340                 345                 350

Lys Ala Gly Ser Glu Glu Ile Phe Ala His Leu Gly Leu Asp Tyr
    355                 360                 365

Val Glu Pro Trp Glu Arg Asn Ala
370                 375

<210> SEQ ID NO 16
<211> LENGTH: 518
<212> TYPE: PRT
<213> ORGANISM: Monodelphis domestica

<400> SEQUENCE: 16

Met His Arg Ile Arg Thr Ile Asp Ser Asp Phe Gly Lys Lys Arg Gln
1               5                   10                  15

Lys Lys Met Asp Asn His Ile Ser Ser Met Ile Tyr Glu Ile Lys Phe
            20                  25                  30

His Glu Phe Val Leu Phe Ile Leu Glu Lys Lys Met Gly Ala Thr Arg
        35                  40                  45

Arg Thr Phe Leu Thr Asp Leu Ala Arg Lys Lys Gly Phe Arg Val Glu
    50                  55                  60

Asn Glu Leu Ser Asn Ser Val Thr His Ile Val Ala Glu Asn Asn Ser
65                  70                  75                  80

Gly Ser Asp Val Leu Ala Trp Leu Lys Thr His Lys Met Glu Lys Thr
                85                  90                  95

Thr Gln Phe Glu Leu Leu Asp Ile Ser Trp Leu Ile Glu Cys Met Lys
            100                 105                 110

Val Gly Lys Pro Val Asp Thr Lys Gly Lys Tyr Gln Leu Met Glu Ser
        115                 120                 125

Arg Val Asp Ser Ala Asn Pro Asp Pro Thr Ala Gly Thr Leu Asn Ile
    130                 135                 140

Leu Pro Pro Thr Thr Lys Thr Ile Ser Gln Tyr Ala Cys Gln Arg Arg
145                 150                 155                 160

Thr Thr Ile Asn Asn His Asn Gln Arg Phe Thr Asp Ala Phe Glu Ile
                165                 170                 175

Leu Ala Lys Asn Tyr Glu Phe Lys Glu Asn Asp Asp Thr Cys Leu Thr
            180                 185                 190

Phe Met Arg Ala Ile Ser Val Leu Lys Cys Leu Pro Phe Glu Val Val
        195                 200                 205

Ser Leu Lys Asp Thr Glu Gly Leu Pro Trp Ile Gly Asp Glu Val Lys
    210                 215                 220

Gly Ile Met Glu Glu Ile Ile Glu Asp Gly Glu Ser Leu Glu Val Gln
225                 230                 235                 240

Ala Val Leu Asn Asp Glu Arg Tyr Gln Ser Phe Lys Leu Phe Thr Ser
            245                 250                 255

Val Phe Gly Val Gly Leu Lys Thr Ala Asp Lys Trp Tyr Arg Met Gly
        260                 265                 270

Phe Arg Thr Leu Asn Lys Ile Arg Ser Asp Lys Thr Leu Lys Leu Thr
    275                 280                 285

Lys Met Gln Lys Ala Gly Leu Cys Tyr Tyr Glu Asp Leu Ile Asp Cys
290                 295                 300

Val Ser Lys Ala Glu Ala Asp Ala Val Ser Leu Val Gln Asp Ala
305                 310                 315                 320

Val Trp Thr Phe Leu Pro Asp Ala Leu Val Thr Ile Thr Gly Gly Phe
            325                 330                 335

Arg Arg Gly Lys Glu Phe Gly His Asp Val Asp Phe Leu Ile Thr Ser
        340                 345                 350

Pro Gly Ala Glu Lys Glu Gln Glu Asp Gln Leu Leu Gln Lys Val Thr
    355                 360                 365

Asn Leu Trp Lys Lys Gln Gly Leu Leu Leu Tyr Cys Asp Leu Ile Glu
370                 375                 380

Ser Thr Phe Glu Asp Leu Lys Leu Pro Ser Arg Lys Ile Asp Ala Leu
385                 390                 395                 400

Asp His Phe Gln Lys Cys Phe Leu Ile Leu Lys Leu Tyr His His Lys
            405                 410                 415

Glu Asp Lys Arg Lys Trp Glu Met Pro Thr Gly Ser Asn Glu Ser Glu
        420                 425                 430

Ala Lys Ser Trp Lys Ala Ile Arg Val Asp Leu Val Val Cys Pro Tyr
    435                 440                 445

Asp Arg Tyr Ala Phe Ala Leu Leu Gly Trp Ser Gly Ser Arg Gln Phe
450                 455                 460

Glu Arg Asp Leu Arg Arg Tyr Ala Thr His Glu Lys Lys Met Met Leu
465                 470                 475                 480

Asp Asn His Ala Leu Tyr Asp Lys Thr Lys Ile Phe Leu Lys Ala
            485                 490                 495

Lys Ser Glu Glu Glu Ile Phe Ala His Leu Gly Leu Glu Tyr Ile Gln
        500                 505                 510

Pro Ser Glu Arg Asn Ala
    515

<210> SEQ ID NO 17
<211> LENGTH: 387
<212> TYPE: PRT
<213> ORGANISM: Monodelphis domestica

<400> SEQUENCE: 17

Ser Ala Asn Pro Asp Pro Thr Ala Gly Thr Leu Asn Ile Leu Pro Pro
1               5                   10                  15

Thr Thr Lys Thr Ile Ser Gln Tyr Ala Cys Gln Arg Arg Thr Thr Ile
            20                  25                  30

Asn Asn His Asn Gln Arg Phe Thr Asp Ala Phe Glu Ile Leu Ala Lys
        35                  40                  45

Asn Tyr Glu Phe Lys Glu Asn Asp Asp Thr Cys Leu Thr Phe Met Arg
    50                  55                  60

Ala Ile Ser Val Leu Lys Cys Leu Pro Phe Glu Val Val Ser Leu Lys

```
            65                  70                  75                  80
Asp Thr Glu Gly Leu Pro Trp Ile Gly Asp Glu Val Lys Gly Ile Met
                85                  90                  95

Glu Glu Ile Ile Glu Asp Gly Glu Ser Leu Glu Val Gln Ala Val Leu
                    100                 105                 110

Asn Asp Glu Arg Tyr Gln Ser Phe Lys Leu Phe Thr Ser Val Phe Gly
                115                 120                 125

Val Gly Leu Lys Thr Ala Asp Lys Trp Tyr Arg Met Gly Phe Arg Thr
    130                 135                 140

Leu Asn Lys Ile Arg Ser Asp Lys Thr Leu Lys Leu Thr Lys Met Gln
145                 150                 155                 160

Lys Ala Gly Leu Cys Tyr Tyr Glu Asp Leu Ile Asp Cys Val Ser Lys
                    165                 170                 175

Ala Glu Ala Asp Ala Val Ser Leu Leu Val Gln Asp Ala Val Trp Thr
                180                 185                 190

Phe Leu Pro Asp Ala Leu Val Thr Ile Thr Gly Gly Phe Arg Arg Gly
            195                 200                 205

Lys Glu Phe Gly His Asp Val Asp Phe Leu Ile Thr Ser Pro Gly Ala
210                 215                 220

Glu Lys Glu Gln Glu Asp Gln Leu Leu Gln Lys Val Thr Asn Leu Trp
225                 230                 235                 240

Lys Lys Gln Gly Leu Leu Leu Tyr Cys Asp Leu Ile Glu Ser Thr Phe
                245                 250                 255

Glu Asp Leu Lys Leu Pro Ser Arg Lys Ile Asp Ala Leu Asp His Phe
            260                 265                 270

Gln Lys Cys Phe Leu Ile Leu Lys Leu Tyr His His Lys Glu Asp Lys
        275                 280                 285

Arg Lys Trp Glu Met Pro Thr Gly Ser Asn Glu Ser Glu Ala Lys Ser
    290                 295                 300

Trp Lys Ala Ile Arg Val Asp Leu Val Val Cys Pro Tyr Asp Arg Tyr
305                 310                 315                 320

Ala Phe Ala Leu Leu Gly Trp Ser Gly Ser Arg Gln Phe Glu Arg Asp
                325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Lys Ala Lys Ser Glu
        355                 360                 365

Glu Glu Ile Phe Ala His Leu Gly Leu Glu Tyr Ile Gln Pro Ser Glu
    370                 375                 380

Arg Asn Ala
385

<210> SEQ ID NO 18
<211> LENGTH: 512
<212> TYPE: PRT
<213> ORGANISM: Elephantulus edwardii

<400> SEQUENCE: 18

Met Asp Pro Leu Gln Met Ala Cys Thr Gly Pro Arg Lys Lys Arg Ala
1               5                   10                  15

Arg Gln Met Asp Thr Ser Met Gly Ser Thr Gln Asp Ile Lys Phe Gln
                20                  25                  30

Asp Leu Val Leu Phe Ile Leu Glu Lys Lys Met Gly Thr Thr Arg Arg
            35                  40                  45
```

```
Ala Phe Leu Met Glu Leu Ala Arg Arg Lys Gly Phe Arg Val Glu Asn
 50                  55                  60
Glu Leu Ser Asp Ser Val Thr His Ile Val Ala Glu Asn Asn Ser Gly
 65                  70                  75                  80
Ser Asp Val Leu Glu Trp Leu Gln Val Gln Lys Ile Lys Ala Ser Ser
                 85                  90                  95
Gln Leu Glu Leu Leu Asp Val Ser Trp Leu Ile Glu Cys Met Gly Ala
                100                 105                 110
Gly Lys Leu Val Glu Ile Thr Gly Lys His Gln Leu Val Ser Ile Met
            115                 120                 125
Val Arg Gly Asp Cys Pro Ala Ser His Asp Ser Ser Pro Gln Lys Thr
130                 135                 140
Glu Ser Ala Ala Val Gln Lys Ile Ser Gln Tyr Ala Cys Gln Arg Arg
145                 150                 155                 160
Thr Thr Leu Asn Asn His Asn His Ile Phe Thr Asp Ala Phe Glu Ile
                165                 170                 175
Leu Ala Glu Asn Cys Glu Phe Arg Glu Asn Gly Ser Tyr Val Thr
                180                 185                 190
Tyr Met Arg Ala Ala Ser Val Leu Lys Ser Leu Pro Phe Ser Ile Ile
            195                 200                 205
Ser Met Lys Asp Thr Glu Gly Ile Pro Cys Leu Ala Asp Lys Val Lys
210                 215                 220
Cys Val Ile Glu Glu Ile Ile Glu Asp Gly Glu Ser Ser Glu Val Lys
225                 230                 235                 240
Ala Val Leu Asn Asp Glu Arg Tyr Lys Ser Phe Lys Leu Phe Thr Ser
                245                 250                 255
Val Phe Gly Val Gly Leu Lys Thr Ala Glu Lys Trp Phe Arg Leu Gly
            260                 265                 270
Phe Arg Thr Leu Ser Gly Ile Met Asn Asp Lys Thr Leu Lys Leu Thr
            275                 280                 285
His Met Gln Lys Ala Gly Phe Leu Tyr Tyr Glu Asp Leu Val Ser Cys
            290                 295                 300
Val Thr Arg Ala Glu Ala Glu Ala Val Gly Val Leu Val Lys Glu Ala
305                 310                 315                 320
Val Trp Ala Phe Leu Pro Asp Ala Ile Val Thr Met Thr Gly Gly Phe
                325                 330                 335
Arg Arg Gly Lys Lys Val Gly His Asp Val Asp Phe Leu Ile Thr Ser
            340                 345                 350
Pro Glu Ala Thr Glu Glu Gln Glu Gln Gln Leu Leu His Lys Val Ile
            355                 360                 365
Thr Phe Trp Glu Lys Glu Gly Leu Leu Leu Tyr Cys Asp Leu Tyr Glu
            370                 375                 380
Ser Thr Phe Glu Lys Leu Lys Met Pro Ser Arg Lys Val Asp Ala Leu
385                 390                 395                 400
Asp His Phe Gln Lys Cys Phe Leu Ile Leu Lys Leu His Arg Glu Cys
                405                 410                 415
Val Asp Asp Gly Thr Ser Ser Gln Leu Gln Gly Lys Thr Trp Lys Ala
            420                 425                 430
Ile Arg Val Asp Leu Val Cys Pro Tyr Glu Cys Arg Ala Phe Ala
            435                 440                 445
Leu Leu Gly Trp Thr Gly Ser Pro Gln Phe Glu Arg Asp Leu Arg Arg
450                 455                 460
Tyr Ala Thr His Glu Arg Lys Met Met Leu Asp Asn His Ala Leu Tyr
```

```
                        465                 470                 475                 480
Asp Lys Thr Lys Arg Lys Phe Leu Ser Ala Asp Ser Glu Glu Asp Ile
                    485                 490                 495

Phe Ala His Leu Gly Leu Asp Tyr Ile Glu Pro Trp Glu Arg Asn Ala
            500                 505                 510

<210> SEQ ID NO 19
<211> LENGTH: 381
<212> TYPE: PRT
<213> ORGANISM: Elephantulus edwardii

<400> SEQUENCE: 19

Asp Cys Pro Ala Ser His Asp Ser Pro Gln Lys Thr Glu Ser Ala
1               5                   10                  15

Ala Val Gln Lys Ile Ser Gln Tyr Ala Cys Gln Arg Arg Thr Thr Leu
                20                  25                  30

Asn Asn His Asn His Ile Phe Thr Asp Ala Phe Glu Ile Leu Ala Glu
            35                  40                  45

Asn Cys Glu Phe Arg Glu Asn Glu Gly Ser Tyr Val Thr Tyr Met Arg
        50                  55                  60

Ala Ala Ser Val Leu Lys Ser Leu Pro Phe Ser Ile Ile Ser Met Lys
65                  70                  75                  80

Asp Thr Glu Gly Ile Pro Cys Leu Ala Asp Lys Val Lys Cys Val Ile
                85                  90                  95

Glu Glu Ile Ile Glu Asp Gly Glu Ser Ser Glu Val Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Leu Gly Phe Arg Thr
130                 135                 140

Leu Ser Gly Ile Met Asn Asp Lys Thr Leu Lys Leu Thr His Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Trp Ala
            180                 185                 190

Phe Leu Pro Asp Ala Ile Val Thr Met Thr Gly Gly Phe Arg Arg Gly
        195                 200                 205

Lys Lys Val Gly His Asp Val Asp Phe Leu Ile Thr Ser Pro Glu Ala
210                 215                 220

Thr Glu Glu Gln Glu Gln Gln Leu Leu His Lys Val Ile Thr Phe Trp
225                 230                 235                 240

Glu Lys Glu Gly Leu Leu Leu Tyr Cys Asp Leu Tyr Glu Ser Thr Phe
                245                 250                 255

Glu Lys Leu Lys Met Pro Ser Arg Lys Val Asp Ala Leu Asp His Phe
            260                 265                 270

Gln Lys Cys Phe Leu Ile Leu Lys Leu His Arg Glu Cys Val Asp Asp
        275                 280                 285

Gly Thr Ser Ser Gln Leu Gln Gly Lys Thr Trp Lys Ala Ile Arg Val
290                 295                 300

Asp Leu Val Val Cys Pro Tyr Glu Cys Arg Ala Phe Ala Leu Leu Gly
305                 310                 315                 320

Trp Thr Gly Ser Pro Gln Phe Glu Arg Asp Leu Arg Arg Tyr Ala Thr
                325                 330                 335
```

-continued

His Glu Arg Lys Met Met Leu Asp Asn His Ala Leu Tyr Asp Lys Thr
                340                 345                 350

Lys Arg Lys Phe Leu Ser Ala Asp Ser Glu Glu Asp Ile Phe Ala His
            355                 360                 365

Leu Gly Leu Asp Tyr Ile Glu Pro Trp Glu Arg Asn Ala
        370                 375                 380

<210> SEQ ID NO 20
<211> LENGTH: 506
<212> TYPE: PRT
<213> ORGANISM: Artificial Sequence
<220> FEATURE:
<223> OTHER INFORMATION: Python bivittatus

<400> SEQUENCE: 20

Met Asn Lys Met Lys Thr Ser Asp Phe Ser Pro Met Arg Lys Arg Gln
1               5                   10                  15

Lys Arg Met Gln Ile Ala Ala Pro Leu Ser Ser Tyr Lys Ile Glu Phe
            20                  25                  30

Lys Asp Ile Ile Ile Phe Ile Val Glu Arg Lys Met Gly Met Thr Arg
        35                  40                  45

Arg Met Phe Leu Met Asp Leu Ala Arg Arg Lys Gly Phe Arg Val Glu
    50                  55                  60

Asn Glu Leu Ser Asp Leu Val Thr His Val Val Ala Glu Asn Asn Ser
65                  70                  75                  80

Cys Ser Glu Ile Leu Lys Trp Leu Gln Lys His Asn Val Glu Asp Ser
                85                  90                  95

Ser Arg Phe Arg Ile Leu Asp Ile Arg Trp Leu Thr Ala Cys Met Glu
            100                 105                 110

Val Gly Arg Pro Val Asp Ser Glu Lys Tyr Gln Leu Pro Glu Asp Glu
        115                 120                 125

Asp Arg Ser Val Thr Ser Asp Leu Asp Arg Asp Ser Ile Ser Glu Tyr
    130                 135                 140

Ala Cys Gln Arg Arg Thr Thr Leu Lys Asn Tyr Asn Gln Lys Phe Thr
145                 150                 155                 160

Asp Ala Phe Glu Ile Leu Ala Glu Asn Tyr Glu Phe Asn Glu Asn Lys
                165                 170                 175

Gly Phe Cys Thr Ala Phe Arg Arg Ala Ala Ser Val Leu Lys Cys Leu
            180                 185                 190

Pro Phe Thr Ile Val Gln Val His Asp Ile Glu Gly Val Pro Trp Met
        195                 200                 205

Gly Lys Gln Val Lys Gly Ile Ile Glu Asp Ile Glu Glu Gly Glu
    210                 215                 220

Ser Ser Lys Val Lys Ala Val Leu Asp Asn Glu Asn Tyr Arg Ser Val
225                 230                 235                 240

Lys Leu Phe Thr Ser Val Phe Gly Val Gly Leu Lys Thr Ser Asp Lys
                245                 250                 255

Trp Tyr Arg Met Gly Leu Arg Thr Leu Glu Glu Val Lys Arg Asp Lys
            260                 265                 270

Asn Leu Lys Leu Thr Arg Met Gln Lys Ala Gly Phe Leu His Tyr Asp
        275                 280                 285

Asp Leu Thr Ser Cys Val Ser Lys Ala Glu Ala Asp Ala Ala Ser Leu
    290                 295                 300

Ile Val Gln Asp Val Val Trp Lys Ile Val Pro Asn Ala Ile Val Thr
305                 310                 315                 320

```
Ile Ala Gly Gly Phe Arg Arg Gly Lys Gln Thr Gly His Asp Val Asp
                325                 330                 335

Phe Leu Ile Thr Val Pro Gly Ser Lys Gln Glu Glu Glu Leu Leu
        340                 345                 350

His Thr Val Ile Asp Ile Trp Lys Lys Gln Glu Leu Leu Leu Tyr Tyr
            355                 360                 365

Asp Leu Ile Glu Ser Thr Phe Glu Asp Thr Lys Leu Pro Ser Arg Lys
    370                 375                 380

Val Asp Ala Leu Asp His Phe Gln Lys Cys Phe Ala Ile Leu Lys Val
385                 390                 395                 400

His Lys Glu Arg Glu Asp Lys Gly Asn Ser Ile Arg Ser Lys Ala Phe
                405                 410                 415

Ser Glu Glu Glu Ile Lys Asp Trp Lys Ala Ile Arg Val Asp Leu Val
                420                 425                 430

Val Val Pro Phe Glu Gln Tyr Ala Phe Ala Leu Leu Gly Trp Thr Gly
            435                 440                 445

Ser Thr Gln Phe Glu Arg Asp Leu Arg Arg Tyr Ala Thr His Glu Lys
    450                 455                 460

Lys Met Met Leu Asp Asn His Ala Leu Tyr Asp Lys Thr Lys Lys Ile
465                 470                 475                 480

Phe Leu Asn Ala Ala Ser Glu Glu Glu Ile Phe Ala His Leu Gly Leu
                485                 490                 495

Asp Tyr Leu Glu Pro Trp Glu Arg Asn Ala
                500                 505

<210> SEQ ID NO 21
<211> LENGTH: 387
<212> TYPE: PRT
<213> ORGANISM: Artificial Sequence
<220> FEATURE:
<223> OTHER INFORMATION: Python bivittatus

<400> SEQUENCE: 21

Glu Lys Tyr Gln Leu Pro Glu Asp Glu Asp Arg Ser Val Thr Ser Asp
1               5                   10                  15

Leu Asp Arg Asp Ser Ile Ser Glu Tyr Ala Cys Gln Arg Thr Thr
            20                  25                  30

Leu Lys Asn Tyr Asn Gln Lys Phe Thr Asp Ala Phe Glu Ile Leu Ala
        35                  40                  45

Glu Asn Tyr Glu Phe Asn Glu Asn Lys Gly Phe Cys Thr Ala Phe Arg
    50                  55                  60

Arg Ala Ala Ser Val Leu Lys Cys Leu Pro Phe Thr Ile Val Gln Val
65                  70                  75                  80

His Asp Ile Glu Gly Val Pro Trp Met Gly Lys Gln Val Lys Gly Ile
                85                  90                  95

Ile Glu Asp Ile Ile Glu Glu Gly Ser Ser Lys Val Lys Ala Val
                100                 105                 110

Leu Asp Asn Glu Asn Tyr Arg Ser Val Lys Leu Phe Thr Ser Val Phe
            115                 120                 125

Gly Val Gly Leu Lys Thr Ser Asp Lys Trp Tyr Arg Met Gly Leu Arg
    130                 135                 140

Thr Leu Glu Glu Val Lys Arg Asp Lys Asn Leu Lys Leu Thr Arg Met
145                 150                 155                 160

Gln Lys Ala Gly Phe Leu His Tyr Asp Asp Leu Thr Ser Cys Val Ser
                165                 170                 175
```

Lys Ala Glu Ala Asp Ala Ala Ser Leu Ile Val Gln Asp Val Val Trp
            180                 185                 190
Lys Ile Val Pro Asn Ala Ile Val Thr Ile Ala Gly Gly Phe Arg Arg
        195                 200                 205
Gly Lys Gln Thr Gly His Asp Val Asp Phe Leu Ile Thr Val Pro Gly
    210                 215                 220
Ser Lys Gln Glu Glu Glu Leu Leu His Thr Val Ile Asp Ile Trp
225                 230                 235                 240
Lys Lys Gln Glu Leu Leu Tyr Tyr Asp Leu Ile Glu Ser Thr Phe
            245                 250                 255
Glu Asp Thr Lys Leu Pro Ser Arg Lys Val Asp Ala Leu Asp His Phe
        260                 265                 270
Gln Lys Cys Phe Ala Ile Leu Lys Val His Lys Glu Arg Glu Asp Lys
    275                 280                 285
Gly Asn Ser Ile Arg Ser Lys Ala Phe Ser Glu Glu Ile Lys Asp
            290                 295                 300
Trp Lys Ala Ile Arg Val Asp Leu Val Val Pro Phe Glu Gln Tyr
305                 310                 315                 320
Ala Phe Ala Leu Leu Gly Trp Thr Gly Ser Thr Gln Phe Glu Arg Asp
            325                 330                 335
Leu Arg Arg Tyr Ala Thr His Glu Lys Lys Met Met Leu Asp Asn His
        340                 345                 350
Ala Leu Tyr Asp Lys Thr Lys Lys Ile Phe Leu Asn Ala Ala Ser Glu
    355                 360                 365
Glu Glu Ile Phe Ala His Leu Gly Leu Asp Tyr Leu Glu Pro Trp Glu
            370                 375                 380
Arg Asn Ala
385

<210> SEQ ID NO 22
<211> LENGTH: 490
<212> TYPE: PRT
<213> ORGANISM: Canis lupus

<400> SEQUENCE: 22

Met Gly Ala Glu Ala Gly Thr Trp Arg Asp Thr Gly Gly Lys Phe Leu
1               5                   10                  15
Leu Leu Ala Thr Glu Pro Glu Arg Lys Phe Arg Ala Ser Asp Ala Cys
            20                  25                  30
Cys Gln Gly Pro Ser Pro Ala Gly Gln Ala Leu Glu Glu Thr Gly Ala
        35                  40                  45
Cys Asp Ser Ile Thr His Ile Val Ala Glu Asn Asn Ser Gly Ser Asp
    50                  55                  60
Val Leu Glu Trp Leu Gln Val Gln Asn Ile Lys Ala Ser Ser Gln Leu
65                  70                  75                  80
Glu Leu Leu Asp Ile Ser Trp Leu Ile Glu Ser Met Gly Ala Gly Lys
            85                  90                  95
Pro Val Glu Met Thr Gly Lys His Gln Leu Met Arg Arg Asp Tyr Thr
        100                 105                 110
Ala Ser Pro Asn Pro Glu Leu Gln Lys Thr Leu Pro Val Ala Val Lys
    115                 120                 125
Lys Ile Ser Gln Tyr Ala Cys Gln Arg Arg Thr Thr Leu Asn Asn Tyr
            130                 135                 140
Asn Asn Val Phe Thr Asp Ala Phe Glu Val Leu Ala Glu Asn Tyr Glu
145                 150                 155                 160

Phe Arg Glu Asn Glu Val Phe Ser Leu Thr Phe Met Arg Ala Ala Ser
            165                 170                 175

Val Leu Lys Ser Leu Pro Phe Thr Ile Ile Ser Met Lys Asp Thr Glu
        180                 185                 190

Gly Ile Pro Cys Leu Gly Asp Gln Val Lys Cys Ile Ile Glu Glu Ile
    195                 200                 205

Ile Glu Asp Gly Glu Ser Ser Glu Val Lys Ala Val Leu Asn Asp Glu
210                 215                 220

Arg Tyr Gln Ser Phe Lys Leu Phe Thr Ser Val Phe Gly Val Gly Leu
225                 230                 235                 240

Lys Thr Ser Glu Lys Trp Phe Arg Met Gly Phe Arg Thr Leu Ser Lys
                245                 250                 255

Ile Lys Ser Asp Lys Ser Leu Lys Phe Thr Pro Met Gln Lys Ala Gly
            260                 265                 270

Phe Leu Tyr Tyr Glu Asp Leu Val Ser Cys Val Thr Arg Ala Glu Ala
        275                 280                 285

Glu Ala Val Gly Val Leu Val Lys Glu Ala Val Gly Ala Phe Leu Pro
    290                 295                 300

Asp Ala Phe Val Thr Met Thr Gly Gly Phe Arg Arg Gly Lys Lys Met
305                 310                 315                 320

Gly His Asp Val Asp Phe Leu Ile Thr Ser Pro Gly Ser Thr Asp Glu
                325                 330                 335

Asp Glu Glu Gln Leu Leu Pro Lys Val Ile Asn Leu Trp Glu Arg Lys
            340                 345                 350

Gly Leu Leu Leu Tyr Cys Asp Leu Val Glu Ser Thr Phe Glu Lys Leu
        355                 360                 365

Lys Leu Pro Ser Arg Lys Val Asp Ala Leu Asp His Phe Gln Lys Cys
    370                 375                 380

Phe Leu Ile Leu Lys Leu His His Gln Arg Val Asp Gly Gly Lys Cys
385                 390                 395                 400

Ser Gln Gln Glu Gly Lys Thr Trp Lys Ala Ile Arg Val Asp Leu Val
                405                 410                 415

Met Cys Pro Tyr Glu Arg Arg Ala Phe Ala Leu Leu Gly Trp Thr Gly
            420                 425                 430

Ser Arg Gln Phe Glu Arg Asp Leu Arg Arg Tyr Ala Ser His Glu Arg
        435                 440                 445

Lys Met Ile Leu Asp Asn His Ala Leu Tyr Asp Lys Thr Lys Lys Ile
    450                 455                 460

Phe Leu Lys Ala Glu Ser Glu Glu Ile Phe Ala His Leu Gly Leu
465                 470                 475                 480

Asp Tyr Ile Glu Pro Trp Glu Arg Asn Ala
            485                 490

<210> SEQ ID NO 23
<211> LENGTH: 381
<212> TYPE: PRT
<213> ORGANISM: Canis lupus

<400> SEQUENCE: 23

Asp Tyr Thr Ala Ser Pro Asn Pro Glu Leu Gln Lys Thr Leu Pro Val
1               5                   10                  15

Ala Val Lys Lys Ile Ser Gln Tyr Ala Cys Gln Arg Arg Thr Thr Leu
            20                  25                  30

Asn Asn Tyr Asn Asn Val Phe Thr Asp Ala Phe Glu Val Leu Ala Glu

```
                35                    40                    45
Asn Tyr Glu Phe Arg Glu Asn Glu Val Phe Ser Leu Thr Phe Met Arg
 50                    55                    60

Ala Ala Ser Val Leu Lys Ser Leu Pro Phe Thr Ile Ile Ser Met Lys
65                     70                    75                    80

Asp Thr Glu Gly Ile Pro Cys Leu Gly Asp Gln Val Lys Cys Ile Ile
                 85                    90                    95

Glu Glu Ile Ile Glu Asp Gly Ser Ser Glu Val Lys Ala Val Leu
                100                   105                   110

Asn Asp Glu Arg Tyr Gln Ser Phe Lys Leu Phe Thr Ser Val Phe Gly
            115                   120                   125

Val Gly Leu Lys Thr Ser Glu Lys Trp Phe Arg Met Gly Phe Arg Thr
        130                   135                   140

Leu Ser Lys Ile Lys Ser Asp Lys Ser Leu Lys Phe Thr Pro Met Gln
145                   150                   155                   160

Lys Ala Gly Phe Leu Tyr Tyr Glu Asp Leu Val Ser Cys Val Thr Arg
                165                   170                   175

Ala Glu Ala Glu Ala Val Gly Val Leu Val Lys Glu Ala Val Gly Ala
            180                   185                   190

Phe Leu Pro Asp Ala Phe Val Thr Met Thr Gly Gly Phe Arg Arg Gly
        195                   200                   205

Lys Lys Met Gly His Asp Val Asp Phe Leu Ile Thr Ser Pro Gly Ser
210                   215                   220

Thr Asp Glu Asp Glu Glu Gln Leu Leu Pro Lys Val Ile Asn Leu Trp
225                   230                   235                   240

Glu Arg Lys Gly Leu Leu Leu Tyr Cys Asp Leu Val Glu Ser Thr Phe
                245                   250                   255

Glu Lys Leu Lys Leu Pro Ser Arg Lys Val Asp Ala Leu Asp His Phe
            260                   265                   270

Gln Lys Cys Phe Leu Ile Leu Lys Leu His His Gln Arg Val Asp Gly
        275                   280                   285

Gly Lys Cys Ser Gln Gln Glu Gly Lys Thr Trp Lys Ala Ile Arg Val
    290                   295                   300

Asp Leu Val Met Cys Pro Tyr Glu Arg Arg Ala Phe Ala Leu Leu Gly
305                   310                   315                   320

Trp Thr Gly Ser Arg Gln Phe Glu Arg Asp Leu Arg Arg Tyr Ala Ser
                325                   330                   335

His Glu Arg Lys Met Ile Leu Asp Asn His Ala Leu Tyr Asp Lys Thr
            340                   345                   350

Lys Lys Ile Phe Leu Lys Ala Glu Ser Glu Glu Ile Phe Ala His
        355                   360                   365

Leu Gly Leu Asp Tyr Ile Glu Pro Trp Glu Arg Asn Ala
    370                   375                   380

<210> SEQ ID NO 24
<211> LENGTH: 512
<212> TYPE: PRT
<213> ORGANISM: Artificial Sequence
<220> FEATURE:
<223> OTHER INFORMATION: Condylura cristata

<400> SEQUENCE: 24

Met Asp Pro Leu Gln Met Ala Cys Thr Gly Pro Arg Lys Lys Arg Ala
1               5                   10                  15

Arg Gln Met Asp Thr Ser Met Gly Ser Thr Gln Asp Ile Lys Phe Gln
```

```
            20                  25                  30
Asp Leu Val Leu Phe Ile Leu Glu Lys Lys Met Gly Thr Thr Arg Arg
             35                  40                  45

Ala Phe Leu Met Glu Leu Ala Arg Arg Lys Gly Phe Arg Val Glu Asn
 50                  55                  60

Glu Leu Ser Asp Ser Val Thr His Ile Val Ala Glu Asn Asn Ser Gly
 65                  70                  75                  80

Ser Asp Val Leu Glu Trp Leu Gln Val Gln Lys Ile Lys Ala Ser Ser
             85                  90                  95

Gln Leu Glu Leu Leu Asp Val Ser Trp Leu Ile Glu Cys Met Gly Ala
             100                 105                 110

Gly Lys Leu Val Glu Ile Thr Gly Lys His Gln Leu Val Ser Ile Met
             115                 120                 125

Val Arg Gly Asp Cys Pro Ala Ser His Asp Ser Pro Gln Lys Thr
             130                 135                 140

Glu Ser Ala Ala Val Gln Lys Ile Ser Gln Tyr Ala Cys Gln Arg Arg
145                 150                 155                 160

Thr Thr Leu Asn Asn His Asn His Ile Phe Thr Asp Ala Phe Glu Ile
             165                 170                 175

Leu Ala Glu Asn Cys Glu Phe Arg Glu Asn Glu Gly Ser Tyr Val Thr
             180                 185                 190

Tyr Met Arg Ala Ala Ser Val Leu Lys Ser Leu Pro Phe Ser Ile Ile
             195                 200                 205

Ser Met Lys Asp Thr Glu Gly Ile Pro Cys Leu Ala Asp Lys Val Lys
             210                 215                 220

Cys Val Ile Glu Glu Ile Ile Glu Asp Gly Glu Ser Ser Glu Val Lys
225                 230                 235                 240

Ala Val Leu Asn Asp Glu Arg Tyr Lys Ser Phe Lys Leu Phe Thr Ser
             245                 250                 255

Val Phe Gly Val Gly Leu Lys Thr Ala Glu Lys Trp Phe Arg Leu Gly
             260                 265                 270

Phe Arg Thr Leu Ser Gly Ile Met Asn Asp Lys Thr Leu Lys Leu Thr
             275                 280                 285

His Met Gln Lys Ala Gly Phe Leu Tyr Tyr Glu Asp Leu Val Ser Cys
             290                 295                 300

Val Thr Arg Ala Glu Ala Glu Ala Val Gly Val Leu Val Lys Glu Ala
305                 310                 315                 320

Val Trp Ala Phe Leu Pro Asp Ala Ile Val Thr Met Thr Gly Gly Phe
             325                 330                 335

Arg Arg Gly Lys Lys Val Gly His Asp Val Asp Phe Leu Ile Thr Ser
             340                 345                 350

Pro Glu Ala Thr Glu Glu Gln Gln Leu Leu His Lys Val Ile
             355                 360                 365

Thr Phe Trp Glu Lys Glu Gly Leu Leu Leu Tyr Cys Asp Leu Tyr Glu
             370                 375                 380

Ser Thr Phe Glu Lys Leu Lys Met Pro Ser Arg Lys Val Asp Ala Leu
385                 390                 395                 400

Asp His Phe Gln Lys Cys Phe Leu Ile Leu Lys Leu His Arg Glu Cys
             405                 410                 415

Val Asp Asp Gly Thr Ser Ser Gln Leu Gln Gly Lys Thr Trp Lys Ala
             420                 425                 430

Ile Arg Val Asp Leu Val Val Cys Pro Tyr Glu Cys Arg Ala Phe Ala
             435                 440                 445
```

-continued

```
Leu Leu Gly Trp Thr Gly Ser Pro Gln Phe Glu Arg Asp Leu Arg Arg
    450                 455                 460
Tyr Ala Thr His Glu Arg Lys Met Met Leu Asp Asn His Ala Leu Tyr
465                 470                 475                 480
Asp Lys Thr Lys Arg Lys Phe Leu Ser Ala Asp Ser Glu Glu Asp Ile
                485                 490                 495
Phe Ala His Leu Gly Leu Asp Tyr Ile Glu Pro Trp Glu Arg Asn Ala
                500                 505                 510

<210> SEQ ID NO 25
<211> LENGTH: 382
<212> TYPE: PRT
<213> ORGANISM: Artificial Sequence
<220> FEATURE:
<223> OTHER INFORMATION: Condylura cristata

<400> SEQUENCE: 25

Gly Asp Cys Pro Ala Ser His Asp Ser Ser Pro Gln Lys Thr Glu Ser
1               5                   10                  15
Ala Ala Val Gln Lys Ile Ser Gln Tyr Ala Cys Gln Arg Arg Thr Thr
                20                  25                  30
Leu Asn His Asn His Ile Phe Thr Asp Ala Phe Glu Ile Leu Ala
            35                  40                  45
Glu Asn Cys Glu Phe Arg Glu Asn Glu Gly Ser Tyr Val Thr Tyr Met
    50                  55                  60
Arg Ala Ala Ser Val Leu Lys Ser Leu Pro Phe Ser Ile Ile Ser Met
65                  70                  75                  80
Lys Asp Thr Glu Gly Ile Pro Cys Leu Ala Asp Lys Val Lys Cys Val
                85                  90                  95
Ile Glu Glu Ile Ile Glu Asp Gly Glu Ser Ser Glu Val Lys Ala Val
                100                 105                 110
Leu Asn Asp Glu Arg Tyr Lys Ser Phe Lys Leu Phe Thr Ser Val Phe
            115                 120                 125
Gly Val Gly Leu Lys Thr Ala Glu Lys Trp Phe Arg Leu Gly Phe Arg
    130                 135                 140
Thr Leu Ser Gly Ile Met Asn Asp Lys Thr Leu Lys Leu Thr His Met
145                 150                 155                 160
Gln Lys Ala Gly Phe Leu Tyr Tyr Glu Asp Leu Val Ser Cys Val Thr
                165                 170                 175
Arg Ala Glu Ala Glu Ala Val Gly Val Leu Val Lys Glu Ala Val Trp
                180                 185                 190
Ala Phe Leu Pro Asp Ala Ile Val Thr Met Thr Gly Gly Phe Arg Arg
            195                 200                 205
Gly Lys Lys Val Gly His Asp Val Asp Phe Leu Ile Thr Ser Pro Glu
    210                 215                 220
Ala Thr Glu Glu Gln Glu Gln Gln Leu Leu His Lys Val Ile Thr Phe
225                 230                 235                 240
Trp Glu Lys Glu Gly Leu Leu Leu Tyr Cys Asp Leu Tyr Glu Ser Thr
                245                 250                 255
Phe Glu Lys Leu Lys Met Pro Ser Arg Lys Val Asp Ala Leu Asp His
                260                 265                 270
Phe Gln Lys Cys Phe Leu Ile Leu Lys Leu His Arg Glu Cys Val Asp
            275                 280                 285
Asp Gly Thr Ser Ser Gln Leu Gln Gly Lys Thr Trp Lys Ala Ile Arg
    290                 295                 300
```

```
Val Asp Leu Val Val Cys Pro Tyr Glu Cys Arg Ala Phe Ala Leu Leu
305                 310                 315                 320

Gly Trp Thr Gly Ser Pro Gln Phe Glu Arg Asp Leu Arg Arg Tyr Ala
                325                 330                 335

Thr His Glu Arg Lys Met Met Leu Asp Asn His Ala Leu Tyr Asp Lys
            340                 345                 350

Thr Lys Arg Lys Phe Leu Ser Ala Asp Ser Glu Glu Asp Ile Phe Ala
        355                 360                 365

His Leu Gly Leu Asp Tyr Ile Glu Pro Trp Glu Arg Asn Ala
    370                 375                 380
```

<210> SEQ ID NO 26
<211> LENGTH: 508
<212> TYPE: PRT
<213> ORGANISM: Ochotona princeps

<400> SEQUENCE: 26

```
Met Asp Ser Leu Gln Thr Gly His Leu Gly Pro Arg Lys Lys Arg Ser
1               5                   10                  15

Arg Gln Thr Asp Ala Ala Arg Thr Ser Ile Pro Gln Glu Val Lys Phe
            20                  25                  30

Gln Asp Leu Val Leu Phe Ile Leu Glu Lys Lys Met Gly Ser Thr Arg
        35                  40                  45

Arg Ala Phe Leu Met Glu Leu Ala Arg Ser Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Val Gln Lys Leu Lys Asp Ser
                85                  90                  95

Ser Gln Leu Glu Leu Leu Asp Val Ser Trp Leu Ile Glu Cys Met Arg
            100                 105                 110

Ala Gly Lys Pro Val Ala Thr Thr Gly Lys His Gln Leu Val Met Arg
        115                 120                 125

Glu Glu Tyr Ser Ala Asn Pro Ser Pro Gly Pro Gln Ala Thr Pro Ala
    130                 135                 140

Val Tyr Lys Ile Ser Gln Tyr Ala Cys Gln Arg Arg Thr Thr Leu Asn
145                 150                 155                 160

Asn His Asn His Ile Phe Thr Asp Ala Phe Glu Ile Leu Ala Glu Asn
                165                 170                 175

Tyr Glu Phe Lys Glu Asn Glu Gly Cys Tyr Val Thr Tyr Met Arg Ala
            180                 185                 190

Ala Ser Val Leu Lys Ser Leu Pro Phe Thr Ile Val Ser Met Lys Asp
        195                 200                 205

Thr Glu Gly Ile Pro Cys Leu Glu Asp Lys Val Lys Ser Ile Met Glu
    210                 215                 220

Glu Ile Ile Glu Glu Gly Glu Ser Ser Glu Val Lys Ala Val Leu Ser
225                 230                 235                 240

Asp Glu Arg Tyr Gln Cys Phe Lys Leu Phe Thr Ser Val Phe Gly Val
                245                 250                 255

Gly Leu Lys Thr Ser Glu Lys Trp Phe Arg Met Gly Phe Arg Ser Leu
            260                 265                 270

Ser Asn Ile Arg Leu Asp Lys Ser Leu Lys Phe Thr Gln Met Gln Lys
        275                 280                 285

Ala Gly Phe Arg Tyr Tyr Glu Asp Ile Val Ser Cys Val Thr Arg Ala
```

```
                290                 295                 300
Glu Ala Glu Ala Val Asp Val Leu Val Asn Glu Ala Val Arg Ala Phe
305                 310                 315                 320

Leu Pro Asp Ala Phe Ile Thr Met Thr Gly Gly Phe Arg Arg Gly Lys
                325                 330                 335

Lys Ile Gly His Asp Val Asp Phe Leu Ile Thr Ser Pro Glu Leu Thr
                340                 345                 350

Glu Glu Asp Glu Gln Gln Leu Leu His Lys Val Met Asn Leu Trp Glu
                355                 360                 365

Lys Lys Gly Leu Leu Leu Tyr His Asp Leu Val Glu Ser Thr Phe Glu
370                 375                 380

Lys Leu Lys Gln Pro Ser Arg Lys Val Asp Ala Leu Asp His Phe Gln
385                 390                 395                 400

Lys Cys Phe Leu Ile Phe Lys Leu Tyr His Glu Arg Val Gly Gly Asp
                405                 410                 415

Arg Cys Arg Gln Pro Glu Gly Lys Asp Trp Lys Ala Ile Arg Val Asp
                420                 425                 430

Leu Val Met Cys Pro Tyr Glu Cys His Ala Phe Ala Leu Leu Gly Trp
                435                 440                 445

Thr Gly Ser Arg Gln Phe Glu Arg Asp Leu Arg Arg Tyr Ala Ser His
                450                 455                 460

Glu Arg Lys Met Ile Leu Asp Asn His Ala Leu Tyr Asp Lys Thr Lys
465                 470                 475                 480

Arg Val Phe Leu Gln Ala Glu Asn Glu Glu Ile Phe Ala His Leu
                485                 490                 495

Gly Leu Asp Tyr Ile Glu Pro Trp Glu Arg Asn Ala
                500                 505

<210> SEQ ID NO 27
<211> LENGTH: 379
<212> TYPE: PRT
<213> ORGANISM: Ochotona princeps

<400> SEQUENCE: 27

Glu Tyr Ser Ala Asn Pro Ser Gly Pro Gln Ala Thr Pro Ala Val
1               5                   10                  15

Tyr Lys Ile Ser Gln Tyr Ala Cys Gln Arg Arg Thr Thr Leu Asn Asn
                20                  25                  30

His Asn His Ile Phe Thr Asp Ala Phe Glu Ile Leu Ala Glu Asn Tyr
                35                  40                  45

Glu Phe Lys Glu Asn Glu Gly Cys Tyr Val Thr Tyr Met Arg Ala Ala
50                  55                  60

Ser Val Leu Lys Ser Leu Pro Phe Thr Ile Val Ser Met Lys Asp Thr
65                  70                  75                  80

Glu Gly Ile Pro Cys Leu Glu Asp Lys Val Lys Ser Ile Met Glu Glu
                85                  90                  95

Ile Ile Glu Glu Gly Glu Ser Ser Glu Val Lys Ala Val Leu Ser Asp
                100                 105                 110

Glu Arg Tyr Gln Cys Phe Lys Leu Phe Thr Ser Val Phe Gly Val Gly
                115                 120                 125

Leu Lys Thr Ser Glu Lys Trp Phe Arg Met Gly Phe Arg Ser Leu Ser
                130                 135                 140

Asn Ile Arg Leu Asp Lys Ser Leu Lys Phe Thr Gln Met Gln Lys Ala
145                 150                 155                 160
```

```
Gly Phe Arg Tyr Tyr Glu Asp Ile Val Ser Cys Val Thr Arg Ala Glu
                165                 170                 175

Ala Glu Ala Val Asp Val Leu Val Asn Glu Ala Val Arg Ala Phe Leu
            180                 185                 190

Pro Asp Ala Phe Ile Thr Met Thr Gly Gly Phe Arg Arg Gly Lys Lys
            195                 200                 205

Ile Gly His Asp Val Asp Phe Leu Ile Thr Ser Pro Glu Leu Thr Glu
        210                 215                 220

Glu Asp Glu Gln Gln Leu Leu His Lys Val Met Asn Leu Trp Glu Lys
225                 230                 235                 240

Lys Gly Leu Leu Leu Tyr His Asp Leu Val Glu Ser Thr Phe Glu Lys
                245                 250                 255

Leu Lys Gln Pro Ser Arg Lys Val Asp Ala Leu Asp His Phe Gln Lys
            260                 265                 270

Cys Phe Leu Ile Phe Lys Leu Tyr His Glu Arg Val Gly Gly Asp Arg
        275                 280                 285

Cys Arg Gln Pro Glu Gly Lys Asp Trp Lys Ala Ile Arg Val Asp Leu
290                 295                 300

Val Met Cys Pro Tyr Glu Cys His Ala Phe Ala Leu Leu Gly Trp Thr
305                 310                 315                 320

Gly Ser Arg Gln Phe Glu Arg Asp Leu Arg Arg Tyr Ala Ser His Glu
                325                 330                 335

Arg Lys Met Ile Leu Asp Asn His Ala Leu Tyr Asp Lys Thr Lys Arg
            340                 345                 350

Val Phe Leu Gln Ala Glu Asn Glu Glu Ile Phe Ala His Leu Gly
        355                 360                 365

Leu Asp Tyr Ile Glu Pro Trp Glu Arg Asn Ala
370                 375

<210> SEQ ID NO 28
<211> LENGTH: 516
<212> TYPE: PRT
<213> ORGANISM: Erinaceus europaeus

<400> SEQUENCE: 28

Met Asp Ala Leu Pro Val Val His Ser Ser Pro Arg Lys Lys Arg Ser
1               5                   10                  15

Arg Leu Met Gly Ala Ser Val Ala Tyr Pro Pro Tyr Asp Ile Lys Phe
            20                  25                  30

His Asn Leu Val Leu Phe Ile Leu Glu Lys Lys Met Gly Ser Ser Arg
        35                  40                  45

Arg Ala Phe Leu Met Glu Leu Ala Arg Arg Lys Gly Phe Arg Val Glu
    50                  55                  60

Asp Glu Leu Ser Asp Ser Ile Thr His Ile Val Ala Glu Asn Asn Thr
65                  70                  75                  80

Gly Ser Glu Val Leu Glu Trp Leu Gln Val Gln Asp Ile Lys Ile Ser
                85                  90                  95

Ser Gln Leu Glu Leu Leu Asp Val Ser Trp Leu Val Glu Cys Met Arg
            100                 105                 110

Ala Gly Asn Pro Val Val Ile Thr Gly Lys His Gln Leu Val Ser Tyr
        115                 120                 125

Thr Val Lys Ser Asp Ala Ser Phe Gly Ser Asn Pro Gly Ser Gln Asn
    130                 135                 140

Thr Pro Pro Leu Ala Ile Lys Lys Ile Ser Gln Tyr Ala Cys Gln Arg
145                 150                 155                 160
```

Arg Thr Ser Leu Asn Asn Cys Asn His Ile Phe Thr Asp Ala Leu Asp
              165                 170                 175

Ile Leu Ala Glu Asn His Glu Phe Arg Glu Asn Glu Val Ser Cys Val
            180                 185                 190

Ala Phe Met Arg Ala Ala Ser Val Leu Lys Ser Leu Pro Phe Thr Ile
        195                 200                 205

Ile Ser Met Lys Asp Thr Lys Gly Ile Pro Cys Leu Gly Asp Lys Ala
    210                 215                 220

Lys Cys Val Ile Glu Glu Ile Ile Glu Asp Gly Ser Ser Glu Val
225                 230                 235                 240

Lys Ala Ile Leu Asn Asp Glu Arg Tyr Gln Ser Phe Lys Leu Phe Thr
                245                 250                 255

Ser Val Phe Gly Val Gly Leu Lys Thr Ser Glu Lys Trp Phe Arg Met
            260                 265                 270

Gly Phe Arg Thr Leu Asn Lys Ile Met Ser Asp Lys Thr Leu Lys Leu
        275                 280                 285

Thr Arg Met Gln Lys Ala Gly Phe Leu Tyr Tyr Glu Asp Leu Val Ser
    290                 295                 300

Cys Val Ala Lys Ala Glu Ala Asp Ala Val Ser Val Leu Val Gln Glu
305                 310                 315                 320

Ala Val Trp Ala Phe Leu Pro Asp Ala Met Val Thr Met Thr Gly Gly
                325                 330                 335

Phe Arg Arg Gly Lys Lys Leu Gly His Asp Val Asp Phe Leu Ile Thr
            340                 345                 350

Ser Pro Gly Ala Thr Glu Glu Glu Gln Gln Leu Leu Pro Lys Val
        355                 360                 365

Ile Asn Phe Trp Glu Arg Lys Gly Leu Leu Tyr His Asp Leu Val
    370                 375                 380

Glu Ser Thr Phe Glu Lys Leu Lys Leu Pro Ser Arg Lys Val Asp Ala
385                 390                 395                 400

Leu Asp His Phe Gln Lys Cys Phe Leu Ile Leu Lys Leu His Leu Gln
                405                 410                 415

His Val Asn Gly Val Gly Asn Ser Lys Thr Gly Gln Gln Glu Gly Lys
            420                 425                 430

Asn Trp Lys Ala Ile Arg Val Asp Leu Val Met Cys Pro Tyr Glu Arg
        435                 440                 445

Arg Ala Phe Ala Leu Leu Gly Trp Thr Gly Ser Arg Gln Phe Glu Arg
    450                 455                 460

Asp Leu Arg Arg Phe Ala Thr His Glu Arg Lys Met Met Leu Asp Asn
465                 470                 475                 480

His Ala Leu Tyr Asp Lys Thr Lys Arg Ile Phe Leu Lys Ala Glu Ser
                485                 490                 495

Glu Glu Glu Ile Phe Ala His Leu Gly Leu Asp Tyr Ile Asp Pro Trp
            500                 505                 510

Glu Arg Asn Ala
        515

<210> SEQ ID NO 29
<211> LENGTH: 384
<212> TYPE: PRT
<213> ORGANISM: Erinaceus europaeus

<400> SEQUENCE: 29

Asp Ala Ser Phe Gly Ser Asn Pro Gly Ser Gln Asn Thr Pro Pro Leu

```
1               5                    10                   15
Ala Ile Lys Lys Ile Ser Gln Tyr Ala Cys Gln Arg Arg Thr Ser Leu
                20                   25                   30

Asn Asn Cys Asn His Ile Phe Thr Asp Ala Leu Asp Ile Leu Ala Glu
                35                   40                   45

Asn His Glu Phe Arg Glu Asn Glu Val Ser Cys Val Ala Phe Met Arg
 50                      55                        60

Ala Ala Ser Val Leu Lys Ser Leu Pro Phe Thr Ile Ile Ser Met Lys
 65                  70                   75                   80

Asp Thr Lys Gly Ile Pro Cys Leu Gly Asp Lys Ala Lys Cys Val Ile
                    85                   90                   95

Glu Glu Ile Ile Glu Asp Gly Glu Ser Ser Glu Val Lys Ala Ile Leu
                    100                  105                  110

Asn Asp Glu Arg Tyr Gln Ser Phe Lys Leu Phe Thr Ser Val Phe Gly
                115                      120                  125

Val Gly Leu Lys Thr Ser Glu Lys Trp Phe Arg Met Gly Phe Arg Thr
 130                     135                      140

Leu Asn Lys Ile Met Ser Asp Lys Thr Leu Lys Leu Thr Arg Met Gln
145                      150                      155              160

Lys Ala Gly Phe Leu Tyr Tyr Glu Asp Leu Val Ser Cys Val Ala Lys
                    165                  170                  175

Ala Glu Ala Asp Ala Val Ser Val Leu Val Gln Glu Ala Val Trp Ala
                180                      185                  190

Phe Leu Pro Asp Ala Met Val Thr Met Thr Gly Gly Phe Arg Arg Gly
                195                      200                  205

Lys Lys Leu Gly His Asp Val Asp Phe Leu Ile Thr Ser Pro Gly Ala
 210                     215                      220

Thr Glu Glu Glu Glu Gln Gln Leu Leu Pro Lys Val Ile Asn Phe Trp
225                      230                      235              240

Glu Arg Lys Gly Leu Leu Leu Tyr His Asp Leu Val Glu Ser Thr Phe
                    245                  250                  255

Glu Lys Leu Lys Leu Pro Ser Arg Lys Val Asp Ala Leu Asp His Phe
                260                      265                  270

Gln Lys Cys Phe Leu Ile Leu Lys Leu His Leu Gln His Val Asn Gly
                275                      280                  285

Val Gly Asn Ser Lys Thr Gly Gln Gln Glu Gly Lys Asn Trp Lys Ala
 290                     295                      300

Ile Arg Val Asp Leu Val Met Cys Pro Tyr Glu Arg Arg Ala Phe Ala
305                      310                      315              320

Leu Leu Gly Trp Thr Gly Ser Arg Gln Phe Glu Arg Asp Leu Arg Arg
                    325                  330                  335

Phe Ala Thr His Glu Arg Lys Met Met Leu Asp Asn His Ala Leu Tyr
                340                      345                  350

Asp Lys Thr Lys Arg Ile Phe Leu Lys Ala Glu Ser Glu Glu Glu Ile
                355                      360                  365

Phe Ala His Leu Gly Leu Asp Tyr Ile Asp Pro Trp Glu Arg Asn Ala
                370                      375                  380
```

<210> SEQ ID NO 30
<211> LENGTH: 510
<212> TYPE: PRT
<213> ORGANISM: Artificial Sequence
<220> FEATURE:
<223> OTHER INFORMATION: Tupaia chinensis
<220> FEATURE:

```
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid

<400> SEQUENCE: 30

Met Asp Leu Leu Arg Met Ala Pro Leu Ser Pro Arg Lys Lys Arg Pro
1               5                   10                  15

Arg Gln Met Gly Ser Ser Met Ala Ser Ala Pro His Asp Ile Lys Phe
            20                  25                  30

Gln Gly Val Val Leu Tyr Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Met Ser Leu Ser His Gln Val Trp Asp Xaa Asn Cys
65                  70                  75                  80

Gly Xaa Asp Val Arg Glu Trp Leu Gln Val Gln Lys Val Lys Ala Ser
                85                  90                  95

Ser Gln Pro Glu Leu Leu Asp Val Ser Trp Leu Val Glu Cys Met Arg
            100                 105                 110

Ala Gly Lys Pro Val Glu Ala Thr Gly Lys His Gln Leu Leu Val Lys
        115                 120                 125

Ser Asp His Ser Thr Ser Pro Ser Pro Gly Pro Gln Lys Thr Pro Ala
    130                 135                 140

Leu Ala Val Gln Lys Ile Ser Gln Tyr Ala Cys Gln Arg Arg Thr Thr
145                 150                 155                 160

Leu Asn Asn Cys Asn Arg Val Phe Thr Asp Ala Phe Glu Thr Leu Ala
                165                 170                 175

Glu Asn Tyr Glu Phe Arg Glu Asn Gly Asp Ser Ser Val Ile Phe Leu
            180                 185                 190

Arg Ala Ala Ser Val Leu Arg Ser Leu Pro Phe Thr Ile Thr Ser Met
        195                 200                 205

Arg Asp Thr Glu Gly Leu Pro Cys Leu Gly Asp Lys Val Lys Cys Val
    210                 215                 220

Ile Glu Glu Ile Ile Glu Asp Gly Glu Ser Ser Glu Val Asn Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Arg Val Arg Ser Asp Lys Ser Leu His Leu Thr Arg Met
        275                 280                 285

Gln Gln Ala Gly Phe Leu Tyr Tyr Glu Asp Leu Ala Ser Cys Val Thr
    290                 295                 300

Arg Ala Glu Ala Glu Ala Val Gly Val Leu Val Lys Glu Ala Val Gly
305                 310                 315                 320

Ala Phe Leu Pro Asp Ala Leu Val Thr Ile Thr Gly Gly Phe Arg Arg
                325                 330                 335

Gly Lys Lys Thr Gly His Asp Val Asp Phe Leu Ile Thr Ser Pro Gly
            340                 345                 350

Ser Thr Glu Glu Lys Glu Glu Leu Leu Gln Lys Val Leu Asn Leu
        355                 360                 365
```

```
Trp Glu Lys Lys Gly Leu Leu Leu Tyr Tyr Asp Leu Val Glu Ser Thr
    370                 375                 380

Phe Glu Lys Leu Lys Thr Pro Ser Arg Lys Val Asp Ala Leu Asp His
385                 390                 395                 400

Phe Pro Lys Cys Phe Leu Ile Leu Lys Leu His His Gln Arg Val Asp
                405                 410                 415

Gly Asp Lys Pro Ser Gln Gln Glu Gly Lys Ser Trp Lys Ala Ile Arg
                420                 425                 430

Val Asp Leu Val Met Cys Pro Tyr Glu Arg His Ala Phe Ala Leu Leu
            435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Lys
465                 470                 475                 480

Thr Lys Arg Val Phe Leu Lys Ala Glu Ser Glu Asp Ile Phe Ala
                485                 490                 495

His Leu Gly Leu Asp Tyr Ile Glu Pro Trp Glu Arg Asn Ala
            500                 505                 510

<210> SEQ ID NO 31
<211> LENGTH: 381
<212> TYPE: PRT
<213> ORGANISM: Artificial Sequence
<220> FEATURE:
<223> OTHER INFORMATION: Tupaia chinensis

<400> SEQUENCE: 31

Asp His Ser Thr Ser Pro Ser Pro Gly Pro Gln Lys Thr Pro Ala Leu
1               5                   10                  15

Ala Val Gln Lys Ile Ser Gln Tyr Ala Cys Gln Arg Arg Thr Thr Leu
                20                  25                  30

Asn Asn Cys Asn Arg Val Phe Thr Asp Ala Phe Glu Thr Leu Ala Glu
            35                  40                  45

Asn Tyr Glu Phe Arg Glu Asn Glu Asp Ser Ser Val Ile Phe Leu Arg
    50                  55                  60

Ala Ala Ser Val Leu Arg Ser Leu Pro Phe Thr Ile Thr Ser Met Arg
65                  70                  75                  80

Asp Thr Glu Gly Leu Pro Cys Leu Gly Asp Lys Val Lys Cys Val Ile
                85                  90                  95

Glu Glu Ile Ile Glu Asp Gly Glu Ser Ser Glu Val Asn Ala Val Leu
                100                 105                 110

Asn Asp Glu Arg Tyr Lys Ser Phe Lys Leu Phe Thr Ser Val Phe Gly
            115                 120                 125

Val Gly Leu Lys Thr Ser Glu Lys Trp Phe Arg Met Gly Phe Arg Thr
    130                 135                 140

Leu Ser Arg Val Arg Ser Asp Lys Ser Leu His Leu Thr Arg Met Gln
145                 150                 155                 160

Gln Ala Gly Phe Leu Tyr Tyr Glu Asp Leu Ala Ser Cys Val Thr Arg
                165                 170                 175

Ala Glu Ala Glu Ala Val Gly Val Leu Val Lys Glu Ala Val Gly Ala
            180                 185                 190

Phe Leu Pro Asp Ala Leu Val Thr Ile Thr Gly Gly Phe Arg Arg Gly
        195                 200                 205

Lys Lys Thr Gly His Asp Val Asp Phe Leu Ile Thr Ser Pro Gly Ser
    210                 215                 220
```

```
Thr Glu Glu Lys Glu Glu Leu Leu Gln Lys Val Leu Asn Leu Trp
225                 230                 235                 240

Glu Lys Lys Gly Leu Leu Leu Tyr Tyr Asp Leu Val Glu Ser Thr Phe
            245                 250                 255

Glu Lys Leu Lys Thr Pro Ser Arg Lys Val Asp Ala Leu Asp His Phe
        260                 265                 270

Pro Lys Cys Phe Leu Ile Leu Lys Leu His His Gln Arg Val Asp Gly
    275                 280                 285

Asp Lys Pro Ser Gln Gln Glu Gly Lys Ser Trp Lys Ala Ile Arg Val
290                 295                 300

Asp Leu Val Met Cys Pro Tyr Glu Arg His Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Lys Thr
            340                 345                 350

Lys Arg Val Phe Leu Lys Ala Glu Ser Glu Asp Ile Phe Ala His
        355                 360                 365

Leu Gly Leu Asp Tyr Ile Glu Pro Trp Glu Arg Asn Ala
    370                 375                 380

<210> SEQ ID NO 32
<211> LENGTH: 525
<212> TYPE: PRT
<213> ORGANISM: Ornithorhynchus anatinus

<400> SEQUENCE: 32

Met Ser Phe Ala Met Phe Pro Ala Lys Lys Glu His Leu Lys Lys Lys
1               5                   10                  15

Arg Arg Arg Met Asn Gly Cys Ile Ser Pro Thr Leu Tyr Glu Ile Lys
            20                  25                  30

Phe Asn Glu Phe Val Leu Phe Ile Leu Glu Lys Lys Met Gly Thr Thr
        35                  40                  45

Arg Arg Ala Phe Leu Met Glu Leu Ala Arg Arg Lys Gly Phe Arg Val
    50                  55                  60

Glu Ser Glu Leu Ser Glu Ser Val Thr His Ile Val Ala Glu Asn Asn
65                  70                  75                  80

Ser Cys Ser Asp Val Leu Glu Trp Leu Ala Val Gln Asn Val Gly Asp
            85                  90                  95

Ser Ser Arg Phe Glu Leu Leu Asp Ile Ser Trp Leu Thr Glu Cys Met
        100                 105                 110

Lys Val Gly Lys Pro Val Glu Ala Ile Gly Lys His Gln Leu Met Arg
    115                 120                 125

Gly Asn Cys Leu Thr Asn Ser Ala Pro Ile Asn Cys Met Thr Glu Thr
130                 135                 140

Pro Ser Leu Ala Thr Lys Gln Val Ser Gln Tyr Ala Cys Glu Arg Arg
145                 150                 155                 160

Thr Thr Leu Asn Asn Cys Asn Gln Lys Phe Thr Asp Ala Phe Glu Ile
            165                 170                 175

Leu Ala Lys Asp Phe Glu Phe Arg Glu Asn Glu Gly Ile Cys Leu Ala
        180                 185                 190

Phe Met Arg Ala Ile Ser Val Leu Lys Cys Leu Pro Phe Thr Ile Val
    195                 200                 205

Arg Met Lys Asp Ile Glu Gly Val Pro Trp Leu Gly Asp Gln Val Lys
210                 215                 220
```

```
Ser Ile Ile Glu Glu Ile Ile Glu Asp Gly Glu Ser Ser Val Lys
225                 230                 235                 240

Ala Val Leu Asn Asp Glu Arg Tyr Arg Ser Phe Gln Leu Phe Asn Ser
            245                 250                 255

Val Phe Glu Val Gly Leu Thr Asp Asn Gly Glu Asn Gly Ile Ala Arg
        260                 265                 270

Gly Phe Gln Thr Leu Asn Glu Val Ile Thr Asp Glu Asn Ile Ser Leu
    275                 280                 285

Thr Lys Thr Thr Leu Ser Thr Ser Leu Trp Asn Tyr Leu Pro Gly Phe
290                 295                 300

Leu Tyr Tyr Glu Asp Leu Val Ser Cys Val Ala Lys Glu Glu Ala Asp
305                 310                 315                 320

Ala Val Tyr Leu Ile Val Lys Glu Ala Val Arg Ala Phe Leu Pro Glu
            325                 330                 335

Ala Leu Val Thr Leu Thr Gly Gly Phe Arg Arg Gly Lys Lys Ile Gly
        340                 345                 350

His Asp Val Asp Phe Leu Ile Ser Asp Pro Glu Ser Gly Gln Asp Glu
    355                 360                 365

Gln Leu Leu Pro Asn Ile Ile Lys Leu Trp Glu Lys Gln Glu Leu Leu
370                 375                 380

Leu Tyr Tyr Asp Leu Val Glu Ser Thr Phe Glu Lys Thr Lys Ile Pro
385                 390                 395                 400

Ser Arg Lys Val Asp Ala Met Asp His Phe Gln Lys Cys Phe Leu Ile
            405                 410                 415

Leu Lys Leu His His Gln Lys Val Asp Ser Gly Arg Tyr Lys Pro Pro
        420                 425                 430

Pro Glu Ser Lys Asn His Glu Ala Lys Asn Trp Lys Ala Ile Arg Val
    435                 440                 445

Asp Leu Val Met Cys Pro Phe Glu Gln Tyr Ala Tyr Ala Leu Leu Gly
450                 455                 460

Trp Thr Gly Ser Arg Gln Phe Glu Arg Asp Leu Arg Arg Tyr Ala Thr
465                 470                 475                 480

His Glu Lys Lys Met Met Leu Asp Asn His Ala Leu Tyr Asp Lys Thr
            485                 490                 495

Lys Lys Ile Phe Leu Lys Ala Glu Ser Glu Glu Asp Ile Phe Thr His
        500                 505                 510

Leu Gly Leu Asp Tyr Ile Glu Pro Trp Glu Arg Asn Ala
    515                 520                 525

<210> SEQ ID NO 33
<211> LENGTH: 394
<212> TYPE: PRT
<213> ORGANISM: Ornithorhynchus anatinus

<400> SEQUENCE: 33

Leu Thr Asn Ser Ala Pro Ile Asn Cys Met Thr Glu Thr Pro Ser Leu
1               5                   10                  15

Ala Thr Lys Gln Val Ser Gln Tyr Ala Cys Glu Arg Arg Thr Thr Leu
            20                  25                  30

Asn Asn Cys Asn Gln Lys Phe Thr Asp Ala Phe Glu Ile Leu Ala Lys
        35                  40                  45

Asp Phe Glu Phe Arg Glu Asn Glu Gly Ile Cys Leu Ala Phe Met Arg
    50                  55                  60

Ala Ile Ser Val Leu Lys Cys Leu Pro Phe Thr Ile Val Arg Met Lys
```

```
               65                  70                  75                  80
    Asp Ile Glu Gly Val Pro Trp Leu Gly Asp Gln Val Lys Ser Ile Ile
                        85                  90                  95

Glu Glu Ile Ile Glu Asp Gly Glu Ser Ser Val Lys Ala Val Leu
                    100                 105                 110

Asn Asp Glu Arg Tyr Arg Ser Phe Gln Leu Phe Asn Ser Val Phe Glu
                    115                 120                 125

Val Gly Leu Thr Asp Asn Gly Glu Asn Gly Ile Ala Arg Gly Phe Gln
                    130                 135                 140

Thr Leu Asn Glu Val Ile Thr Asp Glu Asn Ile Ser Leu Thr Lys Thr
    145                 150                 155                 160

Thr Leu Ser Thr Ser Leu Trp Asn Tyr Leu Pro Gly Phe Leu Tyr Tyr
                    165                 170                 175

Glu Asp Leu Val Ser Cys Val Ala Lys Glu Glu Ala Asp Ala Val Tyr
                    180                 185                 190

Leu Ile Val Lys Glu Ala Val Arg Ala Phe Leu Pro Glu Ala Leu Val
                    195                 200                 205

Thr Leu Thr Gly Gly Phe Arg Arg Gly Lys Lys Ile Gly His Asp Val
                    210                 215                 220

Asp Phe Leu Ile Ser Asp Pro Glu Ser Gly Gln Asp Glu Gln Leu Leu
    225                 230                 235                 240

Pro Asn Ile Ile Lys Leu Trp Glu Lys Gln Glu Leu Leu Leu Tyr Tyr
                    245                 250                 255

Asp Leu Val Glu Ser Thr Phe Glu Lys Thr Lys Ile Pro Ser Arg Lys
                    260                 265                 270

Val Asp Ala Met Asp His Phe Gln Lys Cys Phe Leu Ile Leu Lys Leu
                    275                 280                 285

His His Gln Lys Val Asp Ser Gly Arg Tyr Lys Pro Pro Pro Glu Ser
                    290                 295                 300

Lys Asn His Glu Ala Lys Asn Trp Lys Ala Ile Arg Val Asp Leu Val
    305                 310                 315                 320

Met Cys Pro Phe Glu Gln Tyr Ala Tyr Ala Leu Leu Gly Trp Thr Gly
                    325                 330                 335

Ser Arg Gln Phe Glu Arg Asp Leu Arg Arg Tyr Ala Thr His Glu Lys
                    340                 345                 350

Lys Met Met Leu Asp Asn His Ala Leu Tyr Asp Lys Thr Lys Lys Ile
                    355                 360                 365

Phe Leu Lys Ala Glu Ser Glu Glu Asp Ile Phe Thr His Leu Gly Leu
                    370                 375                 380

Asp Tyr Ile Glu Pro Trp Glu Arg Asn Ala
    385                 390

<210> SEQ ID NO 34
<211> LENGTH: 479
<212> TYPE: PRT
<213> ORGANISM: Jaculus jaculus

<400> SEQUENCE: 34

Met Asp Pro Glu Gln Ala Ala His Trp Ser Pro Arg Lys Lys Arg Pro
    1               5                   10                  15

Arg Gln Arg Ser Ala Ser Val Ala Ser Ala Pro His Asp Ile Arg Phe
                    20                  25                  30

Gln Asp Leu Val Leu Phe Ile Leu Glu Lys Lys Met Gly Ser Thr Arg
                    35                  40                  45
```

Arg Ala Phe Leu Met Glu Leu Ala Arg Arg Lys Gly Phe Arg Val Glu
50              55                  60

Asn Glu Leu Ser Asp Ser Val Thr His Ile Val Ala Glu Asn Asn Ser
65              70                  75                  80

Gly Ser Asp Val Met Lys Trp Leu Gln Gly Gln Asn Ile Gln Ala Ser
                85                  90                  95

Ser Glu Leu Glu Leu Leu Asp Val Ser Trp Leu Ile Glu Cys Met Gly
            100                 105                 110

Ala Gly Lys Pro Val Glu Met Thr Gly Arg His Gln Leu Val Lys Gln
            115                 120                 125

Thr Phe Cys Leu Pro Gly Phe Ile Leu Gln Asp Ala Phe Asp Ile Leu
130                 135                 140

Ala Glu Asn Cys Glu Phe Arg Glu Asn Glu Ala Ser Cys Val Glu Phe
145                 150                 155                 160

Met Arg Ala Ala Ser Val Leu Lys Ser Leu Pro Phe Pro Ile Ile Ser
                165                 170                 175

Val Lys Asp Thr Glu Gly Ile Pro Trp Leu Gly Gly Lys Val Lys Cys
            180                 185                 190

Val Ile Glu Glu Ile Ile Glu Asp Gly Glu Ser Ser Glu Val Lys Ala
            195                 200                 205

Leu Leu Asn Asp Glu Arg Tyr Lys Ser Phe Lys Leu Phe Thr Ser Val
210                 215                 220

Phe Gly Val Gly Leu Lys Thr Ala Glu Arg Trp Phe Arg Met Gly Phe
225                 230                 235                 240

Arg Thr Leu Ser Thr Val Lys Leu Asp Lys Ser Leu Thr Phe Thr Arg
                245                 250                 255

Met Gln Lys Ala Gly Phe Leu His Tyr Glu Asp Leu Val Ser Cys Val
            260                 265                 270

Thr Arg Ala Glu Ala Glu Ala Val Ser Val Leu Val Gln Gln Ala Val
            275                 280                 285

Val Ala Phe Leu Pro Asp Ala Leu Val Ser Met Thr Gly Gly Phe Arg
290                 295                 300

Arg Gly Lys Lys Ile Gly His Asp Val Asp Phe Leu Ile Thr Ser Pro
305                 310                 315                 320

Glu Ala Thr Glu Glu Glu Gln Gln Leu Leu His Lys Val Thr Asn
                325                 330                 335

Phe Trp Glu Gln Lys Gly Leu Leu Leu Tyr Cys Asp His Val Glu Ser
                340                 345                 350

Thr Phe Glu Lys Cys Lys Leu Pro Ser Arg Lys Val Asp Ala Leu Asp
            355                 360                 365

His Phe Gln Lys Cys Phe Leu Ile Leu Lys Leu Tyr Arg Glu Arg Val
            370                 375                 380

Asp Ser Val Lys Ser Ser Gln Gln Glu Gly Lys Gly Trp Lys Ala Ile
385                 390                 395                 400

Arg Val Asp Leu Val Met Cys Pro Tyr Glu Cys Arg Ala Phe Ala Leu
                405                 410                 415

Leu Gly Trp Thr Gly Ser Arg Gln Phe Glu Arg Asp Leu Arg Arg Tyr
            420                 425                 430

Ala Thr His Glu Arg Lys Met Arg Leu Asp Asn His Ala Leu Tyr Asp
            435                 440                 445

Lys Thr Lys Arg Val Phe Leu Lys Ala Glu Ser Glu Glu Ile Phe
450                 455                 460

Ala His Leu Gly Leu Glu Tyr Ile Glu Pro Leu Glu Arg Asn Ala

<210> SEQ ID NO 35
<211> LENGTH: 384
<212> TYPE: PRT
<213> ORGANISM: Jaculus jaculus

<400> SEQUENCE: 35

Ser Ser Glu Leu Glu Leu Leu Asp Val Ser Trp Leu Ile Glu Cys Met
1               5                   10                  15

Gly Ala Gly Lys Pro Val Glu Met Thr Gly Arg His Gln Leu Val Lys
            20                  25                  30

Gln Thr Phe Cys Leu Pro Gly Phe Ile Leu Gln Asp Ala Phe Asp Ile
        35                  40                  45

Leu Ala Glu Asn Cys Glu Phe Arg Glu Asn Glu Ala Ser Cys Val Glu
    50                  55                  60

Phe Met Arg Ala Ala Ser Val Leu Lys Ser Leu Pro Phe Pro Ile Ile
65                  70                  75                  80

Ser Val Lys Asp Thr Glu Gly Ile Pro Trp Leu Gly Gly Lys Val Lys
                85                  90                  95

Cys Val Ile Glu Glu Ile Ile Glu Asp Gly Glu Ser Ser Glu Val Lys
            100                 105                 110

Ala Leu Leu Asn Asp Glu Arg Tyr Lys Ser Phe Lys Leu Phe Thr Ser
        115                 120                 125

Val Phe Gly Val Gly Leu Lys Thr Ala Glu Arg Trp Phe Arg Met Gly
    130                 135                 140

Phe Arg Thr Leu Ser Thr Val Lys Leu Asp Lys Ser Leu Thr Phe Thr
145                 150                 155                 160

Arg Met Gln Lys Ala Gly Phe Leu His Tyr Glu Asp Leu Val Ser Cys
                165                 170                 175

Val Thr Arg Ala Glu Ala Glu Ala Val Ser Val Leu Val Gln Gln Ala
            180                 185                 190

Val Val Ala Phe Leu Pro Asp Ala Leu Val Ser Met Thr Gly Gly Phe
        195                 200                 205

Arg Arg Gly Lys Lys Ile Gly His Asp Val Asp Phe Leu Ile Thr Ser
    210                 215                 220

Pro Glu Ala Thr Glu Glu Glu Gln Gln Leu Leu His Lys Val Thr
225                 230                 235                 240

Asn Phe Trp Glu Gln Lys Gly Leu Leu Leu Tyr Cys Asp His Val Glu
                245                 250                 255

Ser Thr Phe Glu Lys Cys Lys Leu Pro Ser Arg Lys Val Asp Ala Leu
            260                 265                 270

Asp His Phe Gln Lys Cys Phe Leu Ile Leu Lys Leu Tyr Arg Glu Arg
        275                 280                 285

Val Asp Ser Val Lys Ser Ser Gln Gln Glu Gly Lys Gly Trp Lys Ala
    290                 295                 300

Ile Arg Val Asp Leu Val Met Cys Pro Tyr Glu Cys Arg Ala Phe Ala
305                 310                 315                 320

Leu Leu Gly Trp Thr Gly Ser Arg Gln Phe Glu Arg Asp Leu Arg Arg
                325                 330                 335

Tyr Ala Thr His Glu Arg Lys Met Arg Leu Asp Asn His Ala Leu Tyr
            340                 345                 350

```
Asp Lys Thr Lys Arg Val Phe Leu Lys Ala Glu Ser Glu Glu Glu Ile
        355                 360                 365

Phe Ala His Leu Gly Leu Glu Tyr Ile Glu Pro Leu Glu Arg Asn Ala
    370                 375                 380
```